United States Patent
Bannister et al.

(10) Patent No.: US 11,560,389 B2
(45) Date of Patent: *Jan. 24, 2023

(54) HETEROCYCLIC INHIBITORS OF MONOCARBOXYLATE TRANSPORTERS

(71) Applicant: UNIVERSITY OF FLORIDA RESEARCH FOUNDATION, INCORPORATED, Gainesville, FL (US)

(72) Inventors: Thomas D. Bannister, Palm Beach Gardens, FL (US); William R. Roush, Jupiter, FL (US); John L. Cleveland, Land O'Lakes, FL (US); Jun Yong Choi, Jupiter, FL (US); Reji N. Nair, Palm Beach Gardens, FL (US); Andy S. Tsai, Mystic, CT (US); Jitendra K. Mishra, Miami, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 111 days.

This patent is subject to a terminal disclaimer.

(21) Appl. No.: 16/949,983

(22) Filed: Nov. 23, 2020

(65) Prior Publication Data

US 2021/0094969 A1 Apr. 1, 2021

Related U.S. Application Data

(63) Continuation of application No. 16/439,950, filed on Jun. 13, 2019, now Pat. No. 10,851,113, which is a continuation of application No. 15/545,168, filed as application No. PCT/US2016/014461 on Jan. 22, 2016, now Pat. No. 10,329,303.

(60) Provisional application No. 62/106,479, filed on Jan. 22, 2015.

(51) Int. Cl.
| | | |
|---|---|---|
| *C07D 495/04* | (2006.01) | |
| *A61K 31/519* | (2006.01) | |
| *C07D 487/04* | (2006.01) | |
| *A61K 31/155* | (2006.01) | |
| *A61K 31/5025* | (2006.01) | |
| *A61P 35/00* | (2006.01) | |

(52) U.S. Cl.
CPC .......... *C07D 495/04* (2013.01); *A61K 31/155* (2013.01); *A61K 31/5025* (2013.01); *A61K 31/519* (2013.01); *A61P 35/00* (2018.01); *C07D 487/04* (2013.01)

(58) Field of Classification Search
CPC ............................ C07D 495/04; A61K 31/519
USPC ...................................... 544/278; 514/260.1
See application file for complete search history.

(56) References Cited

U.S. PATENT DOCUMENTS

| | | | |
|---|---|---|---|
| 10,329,303 B2* | 6/2019 | Bannister | ............. C07D 495/04 |
| 10,851,113 B2 | 12/2020 | Bannister et al. | |
| 2004/0072746 A1 | 4/2004 | Sullivan et al. | |
| 2006/0052400 A1 | 3/2006 | Guile | |
| 2011/0092499 A1 | 4/2011 | Bourke et al. | |
| 2018/0002343 A1 | 1/2018 | Bannister et al. | |
| 2019/0330228 A1 | 10/2019 | Bannister et al. | |

FOREIGN PATENT DOCUMENTS

| | | |
|---|---|---|
| JP | 2006516974 A | 7/2006 |
| JP | 2018502876 A | 2/2018 |
| JP | 6725519 B2 | 6/2020 |
| WO | WO-2010089580 A1 | 8/2010 |
| WO | WO-2016118825 A1 | 7/2016 |

OTHER PUBLICATIONS

U.S. Appl. No. 62/106,479, filed Jan. 22, 2015, Heterocyclic Inhibitors of Monocarboxylate Transporters.
U.S. Appl. No. 15/545,168 U.S. Pat. No. 10,329,303, filed Jul. 20, 2017, Heterocyclic Inhibitors of Monocarboxylate Transporters.
U.S. Appl. No. 16/439,950, filed Jun. 13, 2019, Heterocyclic Inhibitors of Monocarboxylate Transporters.
"U.S. Appl. No. 15/545,168, Non Final Office Action dated Aug. 23, 2018", 10 pgs.
"U.S. Appl. No. 15/545,168, Notice of Allowance dated Feb. 21, 2019", 9 pgs.
"U.S. Appl. No. 15/545,168, Notice of Allowance dated Apr. 29, 2019", 6 pgs.
"U.S. Appl. No. 15/545,168, Response filed Jan. 15, 2019 to Non Final Office Action dated Aug. 23, 2018", 16 pgs.
"U.S. Appl. No. 15/545,168, Response filed Jun. 19, 2018 to Restriction Requirement dated Jan. 22, 2018", 15 pgs.
"U.S. Appl. No. 15/545,168, Restriction Requirement dated Jan. 22, 2018", 9 pgs.
"U.S. Appl. No. 16/439,950, Final Office Action dated Jul. 6, 2020", 7 pgs.
"U.S. Appl. No. 16/439,950, Non Final Office Action dated Feb. 21, 2020", 10 pgs.
"U.S. Appl. No. 16/439,950, Notice of Allowance dated Jul. 29, 2020", 9 pgs.
"U.S. Appl. No. 16/439,950, Preliminary Amendment filed Jul. 12, 2019", 15 pgs.
"U.S. Appl. No. 16/439,950, Response filed Jun. 16, 2020 to Non Final Office Action dated Feb. 21, 2020", 16 pgs.
"U.S. Appl. No. 16/439,950, Response filed Jul. 9, 2020 to Final Office Action dated Jul. 6, 2020", 14 pgs.
"U.S. Appl. No. 16/439,950, Response filed Dec. 10, 2019 to Restriction Requirement dated Sep. 17, 2019", 13 pgs.

(Continued)

*Primary Examiner* — Jeffrey H Murray
(74) *Attorney, Agent, or Firm* — Wolf, Greenfield & Sacks, P.C.

(57) ABSTRACT

The invention provides compounds of formulae A, B, and C as described herein that inhibit monocarboxylate transporters, such as MCT1 and MCT4. Compounds of the invention can be used for treatment of a condition in a patient, wherein the condition is characterized by the heightened activity or by the high prevalence of MCT1 and/or MCT4, such as cancer or type II diabetes.

5 Claims, 4 Drawing Sheets

(56) References Cited

OTHER PUBLICATIONS

"U.S. Appl. No. 16/439,950, Restriction Requirement dated Sep. 17, 2019", 8 pgs.
"International Application Serial No. PCT/US2016/014461, International Preliminary Report on Patentability dated Aug. 3, 2017", 7 pgs.
"International Application Serial No. PCT/US2016/014461, International Search Report dated Apr. 8, 2016", 2 pgs.
"International Application Serial No. PCT/US2016/014461, Written Opinion dated Apr. 8, 2016", 5 pgs.
"Japanese Application Serial No. 2017-538322, Notification of Reasons for Refusal dated Oct. 8, 2019", 3 pgs.
"Japanese Application Serial No. 2017-538322, Response filed Apr. 7, 2020 to Notification of Reasons for Refusal dated Oct. 8, 2019", w/ English claims, 36 pgs.
Doherty, Joanne R, et al., "Blocking Lactate Export by Inhibiting the Myc Target MCT1 Disables Glycolysis and Glutathione Synthesis", Cancer Research, 74(3), (Feb. 1, 2014), 908-920.
Zhao, Chao, et al., "Expression and Distribution of Lactate/Monocarboxylate Transporter Isoforms in Pancreatic Islets and the Exocrine Pancreas", Diabetes, vol. 50, (Feb. 2001), 361-366.
"European Application Serial No. 16740818.6, Communication Pursuant to Article 94(3) EPC ated Sep. 21, 2020", 7 pgs.
"European Application Serial No. 16740818.6, Response filed Jan. 14, 2021 to Communication Pursuant to Article 94(3) EPC dated Sep. 21, 2020", 148 pgs.

* cited by examiner thieno[2,3-*d*]pyrimidine-2,4(1*H*,3*H*)-dione 2,6-dihydro-1*H*-pyrrolo[3,4-*d*]pyridazin-1-one 1*H*-pyrrolo[3,4-*d*]pyrimidine-2,4(3*H*,6*H*)-dione SR-11105
(the product of Example 9)

SR-13779
(the product of Example 21)

HETEROCYCLIC INHIBITORS OF MONOCARBOXYLATE TRANSPORTERS

CROSS-REFERENCE TO RELATED APPLICATION

This application is a continuation of U.S. patent application Ser. No. 16/439,950 filed on Jun. 13, 2019, which is a continuation of U.S. patent application Ser. No. 15/545,168 filed on Jul. 20, 2017, issued as U.S. Pat. No. 10,329,303 on Jun. 25, 2019, which is a national stage application of International Application No. PCT/US2016/014461 filed on Jan. 22, 2016, which claims the priority of U.S. Provisional Patent Application No. 62/106,479 filed Jan. 22, 2015, the disclosures of which applications are incorporated in their entireties as if fully set forth herein.

STATEMENT OF GOVERNMENT SUPPORT

This invention was made with government support under R01 CA154739 awarded by the National Institutes of Health. The government has certain rights in the invention.

BACKGROUND

In the 1920s the German biochemist Otto Warburg described metabolic differences between cancerous and normal cells, where he noted that tumor cells rely upon a high rate of aerobic glycolysis rather than oxidative phosphorylation to produce energy for maintenance of cellular functions.[1,2] Indeed, cancer cells have up to a 60-fold enhanced rate of glycolysis relative to normal cells, even with sufficient oxygen.[1] This dependence upon glycolysis, and its consequences, is termed "the Warburg effect".[2]

Malignant cells are highly anabolic and require very high levels nutrients, ATP and building blocks to synthesize components needed for their growth and survival. Use of the glycolytic pathway provides ATP but also drives production of lactate, which is produced from pyruvate at the end of the glycolytic pathway. Massive lactate production by the tumor cell requires an efficient means for its consumption or elimination, to prevent intracellular acidification of the cancer cell.

Two mechanisms for handling excess lactate have been described. First, in some rare tumor types lactate is converted to pyruvate for entry into the TCA cycle. More commonly, however, lactate homeostasis is maintained via a family of twelve-membrane pass cell surface proteins known as the monocarboxylate transporters (MCTs; also known as the SLC16a transporter family). Fourteen MCTs are known, but only MCT1, MCT2, MCT3 and MCT4 transport small monocarboxylates such as lactate, pyruvate and ketone bodies (acetoacetate and β-hydroxybutyrate) across plasma membranes in a proton-linked exchange.[3] Expression analyses have established that most aggressive tumor types express markedly elevated levels of MCT1, MCT4 or both.[4] The chaperone protein CD147, which contains immunoglobulin-like domains, is required for MCT1 and MCT4 cell surface expression and is co-localized with the transporters. MCT1, MCT4 and CD147 are now high priority targets for cancer therapeutics.[4]

The expression of MCT1 and MCT4 is regulated by two major oncogenic transcription factors, MYC and hypoxia inducible factor-1α (HIF-1α), respectively,[4,5] that direct marked increases in the production of key proteins that support aerobic glycolysis, including amino acid transporters and enzymes involved in the catabolism of glutamine and glucose.[6] Malignancies having MYC involvement and hypoxic tumors are generally resistant to current frontline therapies, with high rates of treatment failure, relapse and high patient mortality.[7,8] Importantly, inhibition of MCT1 or MCT4 can kill tumor cells ex vivo and provoke tumor regression in vivo,[4,9] and their potency is augmented by agents such as metformin that force a glycolytic phenotype upon the cancer cell.[4]

Many weak MCT inhibitors (i.e., those effective at high micromolar levels) have been described, including α-cyano-4-hydroxycinnamate[10,11] stilbene disulfonates,[12] phloretin[13] and related flavonoids.[14] Coumarin-derived covalent MCT inhibitors have also recently been disclosed,[15,16] as have pteridinones.[17]

The most advanced MCT1 inhibitors are related pyrrolopyrimidine diones, pyrrolopyridazinones, and thienopyrimidine diones,[18-23] including a compound that has advanced into clinical trials for treating some human malignancies.[24,25] These compounds, and to our knowledge all MCT1 inhibitors yet described, are dual MCT1/MCT2 inhibitors. MCT2 has very high sequence homology with MCT1, yet it likely has a lesser role than MCT1 and MCT4 for monocarboxylate transport in human cancers based upon expression studies. However, MCT2 inhibition may play a role in potential off-target effects of current agents that could arise from blocking lactate transport in normal cells.

The first highly potent MCT inhibitor was initially identified via a cell-based assay seeking immunosuppressive agents that inhibit NFAT1-directed IL-2 transcription.[26] MCT1 inhibition as its mechanism of action was described a full decade later.[18] Several subsequently published analogs are also potent MCT1 inhibitors, with low nanomolar Ki values for MCT1 inhibition and low nanomolar $EC_{50}$ values inn MTT assays for growth of MCT1-expressing tumors.

In many human tumors MCT1 and MCT4 are inversely expressed. Small molecule MCT1 inhibitors are now known to disable tumor cell metabolism, proliferation and survival, and impair tumorigenic potential in vivo in tumors expressing high levels of MCT1.[4] MCT4 inhibitors are likely to be similarly effective for tumors expressing elevated levels of MCT4. Antitumor effects of MCT1 inhibitors are augmented by co-administration of the biguanide metformin, which is thought to further augment reliance by tumor cells upon aerobic glycolysis and thus increase the demand to MCT1-mediated efflux of lactate.[4]

In addition to antitumor effects, inhibitors of MCT1 and/or MCT4 may have other important biological effects, such as immune suppression,[18] anti-inflammatory,[26] and anti-diabetic effects.[27-32] MCT1 is normally expressed at very low levels in pancreatic islets and in beta-cells in particular.[27-28] This scenario explains the very slow uptake of lactate in these cells.[29] A hallmark of exercise-induced hyperinsulinism (EIHI) is inappropriate insulin secretion following vigorous physical activity, which leads to hypoglycemia.[30] In a 2012 study, Rutter and co-workers established that EIHI is associated with elevated expression of MCT1 in beta-cells and that transgenic mice engineered to overexpress MCT1 in part displayed many of the hallmarks of EIHI6.[31] While the link between lactate and insulin secretion has been suggested since the late 1980s[32] these more recent studies clarify the central role of MCT1 (and perhaps of the related lactate transporters MCT2 and MCT4).

SUMMARY

The present invention provides, in various embodiments, a compound of formula A, B, or C:

A

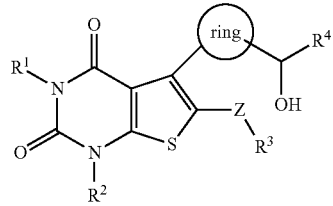

B

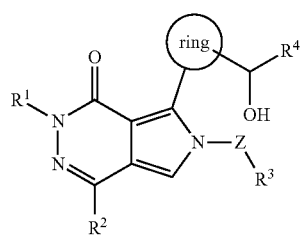

C

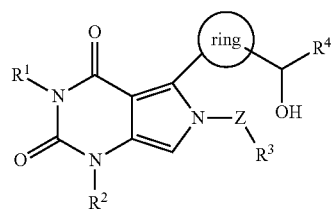

wherein $R^1$ is selected from the group consisting of hydrogen, $(C_1-C_6)$alkyl, $(C_3-C6)$branched alkyl, $(C_3-C_7)$cycloalkyl, and $(C_1-C_6)$fluoroalkyl.

$R^2$ is selected from the group consisting of hydrogen, $(C_1-C_6)$alkyl, $(C_3-C_6)$branched alkyl, $(C_3-C_7)$cycloalkyl, $(C_1-C_6)$fluoroalkyl, a $(C_6-C_{10})$aryl ring system, a 5- to 9-membered heteroaryl ring system, a $(C_1-C_6)$alkyl-$(C_6-C_{10})$aryl ring system, and a $(C_1-C_6)$alkyl-(5- to 9-membered)heteroaryl ring system;

provided that when $R^2$ comprises an aryl or heteroaryl ring system, the ring system bears 0-2 independently selected substituents from the group consisting of fluoro, chloro, trifluoromethyl, $(C_1-C_6)$alkoxy, and $(C_1-C_6)$fluoroalkoxy;

$R^3$ is a monocyclic or bicyclic (C6-C10) aryl or a monocyclic or bicyclic (5- to 10-membered) heteroaryl group, wherein the aryl or heteroaryl can be substituted or unsubstituted;

$R^4$ is hydrogen, $(C_1-C_6)$alkyl, $(C_3-C_6)$branched alkyl, $(C_3-C_7)$cycloalkyl, $(C_5-C_{10})$aryl, (5- to 7-membered)heteroaryl, or (4- to 7-membered) saturated heterocyclyl with 1-2 instances of heteroatoms selected from the group consisting of NH, NMe, O, and S;

for structure A, Z is $CH_2$, $CH((C_1-C_6)$alkyl), $CH((C_3-C_7)$cycloalkyl), O, N, S, S(O), or $SO_2$;

for structures B and C, Z is $CH_2$, $CH((C_1-C_6)$alkyl), $CH((C_3-C_7)$cycloalkyl), or O;

n=1, 2, or 3;

the cyclic group indicated as "ring" is an aryl or heteroaryl group of any one of the following:

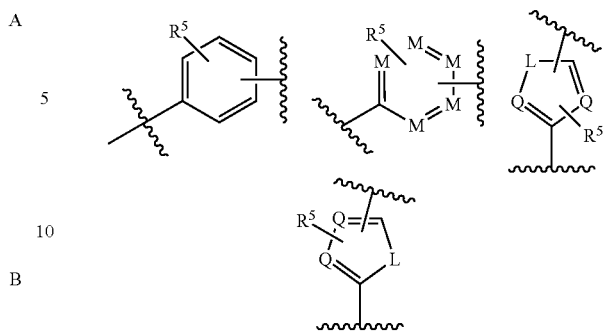

wherein the wavy lines indicate points of bonding, and wherein M is independently selected CH or N, provided that M group can be a nitrogen atom in 0, 1, or 2, instances;

L is S, O, NH, $N(C_1-C_6)$alkyl, or $NCF_3$;

each Q is independently CH or N;

wherein $R^5$ is optionally present, when present, $R^5$ is one to four instances of independently selected F, Cl, Br, $CF_3$, $(C_1-C_6)$alkyl, $OCF_3$, $O(C_1-C_6)$alkyl, or $CO$—$(C_1-C_6)$alkyl; or, the cyclic group indicated as "ring" is a $(C_3-C_7)$cycloalkyl or a saturated (3- to 7-membered)heterocyclyl comprising 1-2 heteroatoms selected from the group consisting of O, NH, N(C1-C6)alkyl, and N(C1-C6)fluoroalkyl; wherein the points of bonding may be cis or trans; wherein $R^5$ is optionally present, when present, $R^5$ is one to four instances of independently selected F, Cl, Br, $CF_3$, $(C_1-C_6)$alkyl, $OCF_3$, $O(C_1-C_6)$alkyl, or $CO$—$(C_1-C_6)$alkyl;

or a pharmaceutically acceptable salt thereof.

The invention further provides a pharmaceutical composition comprising a compound of the invention and a pharmaceutically acceptable excipient.

In various embodiments, the invention provides a method of inhibiting monocarboxylate transporter MCT1, monocarboxylate transporter MCT4, or both, comprising contacting the monocarboxylate transporter with an effective amount or concentration of a compound of the invention.

The invention further provides a method of treatment of a condition in a mammal wherein treatment of the condition with a compound having an inhibitor effect on MCT1, MCT4, or both is medically indicated, comprising administering an effective amount of a compound of the invention. For instance, in various embodiments, a compound of the invention shows an anti-tumor, anti-diabetes, anti-inflammatory, or immunosuppressive pharmacological effect. The inventive compounds can be used for treatment of a condition in a patient wherein the condition is characterized by the heightened activity or by the high prevalence of MCT1 and/or MCT4. For instance, the condition can be cancer or type II diabetes.

DETAILED DESCRIPTION

Figure 1:
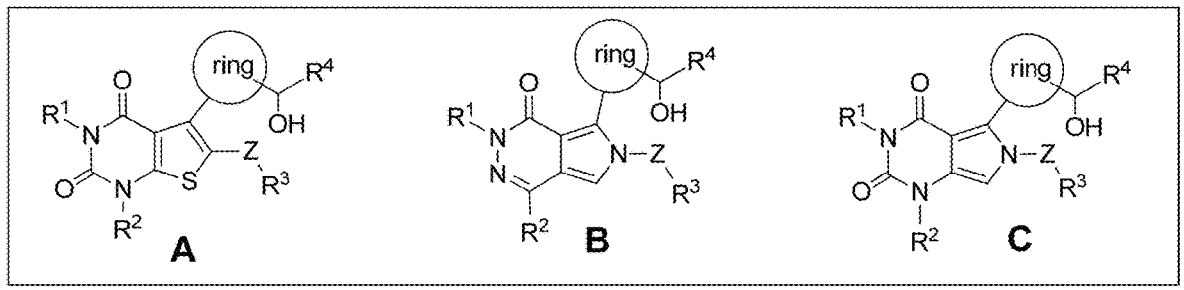
FIG. 1 shows structural scaffolds of compounds of the invention.
Figure 2:
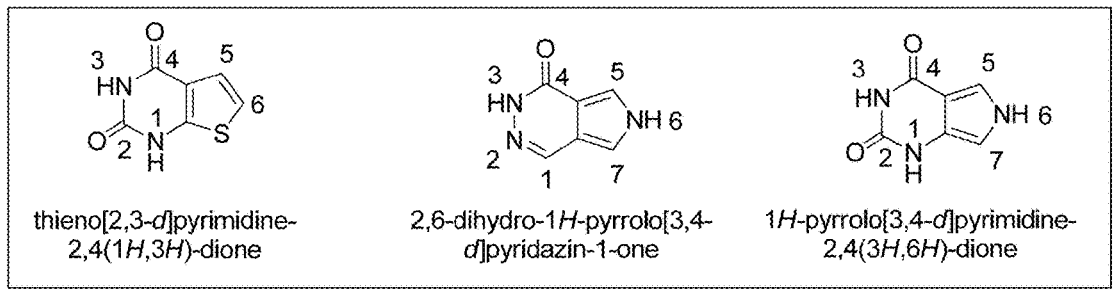
FIG. 2 shows numbering schemes for the scaffolds.

The terms MCT1 and MCT4 refer to monocarboxylate transporter 1 and monocarboxylate transporter 4, respectively.

The term "inhibitor" as used herein refers to a compound that binds to a target and renders it biologically inactive or less active.

The term "heteroatom" as used herein refers to an atom of any element other than carbon or hydrogen. Common heteroatoms include nitrogen, oxygen, phosphorus, sulfur and selenium.

The abbreviation "CNS" as used herein refers to the central nervous system of an organism.

The term "$EC_{50}$" as used herein refers to the dose of a test compound which produces 50% of its maximum response or effect in an assay.

The term "$IC_{50}$" as used herein refers to the dose of a test compound which produces 50% inhibition in a biochemical assay.

The term "alkyl" as used herein throughout the specification, examples, and claims refers to a hydrocarbon group, and includes branched chain variations, or "branched alkyl" groups.

The term "cycloalkyl" as used herein throughout the specification, examples, and claims refers to a cyclic hydrocarbon group, and may include alkyl substituents on the cyclic hydrocarbon group.

The term "substituted alkyl" as used herein refers to alkyl moieties having substituents replacing a hydrogen atom on one or more carbon atoms of the hydrocarbon backbone. Such substituents can include, for example, a halogen, a halogenated alkyl (e.g., $CF_3$), a hydroxyl, a carbonyl, an amino, an amido, an amidine, an imine, an alkoxy, a halogenated alkoxy (e.g., $OCF_3$, $OCHF_2$, etc.) a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic group. It will be understood by those skilled in the art that the moieties substituted on the hydrocarbon chain can themselves be substituted, if appropriate.

The term "aryl" and "heteroaryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls. The terms ortho, meta and para apply to 1,2-, 1,3- and 1,4-disubstituted benzenes, respectively. For example, the names "1,2-dimethylbenzene" and "ortho, meta-dimethylbenzene" are synonymous.

The term "aralkyl" as used herein refers to an alkyl group substituted with an aryl group (e.g., an aromatic or heteroaromatic group). Examples include $CH_2Ph$, $CH_2CH_2Ph$, $CH_2CH_2$— indole, and the like. The aromatic ring can be substituted at one or more ring positions with such substituents, as described above.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

The terms "heterocyclyl" or "heterocyclic group" as used herein refer to 3- to 10-membered ring structures, more preferably 3- to 7-membered rings that include one to four heteroatoms. Heterocycles can also be polycycles. Heterocyclyl groups include, for example, azetidine, azepine, thiophene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultans, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings", Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

As used herein, the term "halogen" designates —F, —Cl, —Br or —I.

As used herein, the term "hydroxyl" means —OH.

As used herein, the term "sulfonyl" means —$SO_2$—.

The terms "amine" and "amino" as used herein are recognized in the art and refer to both unsubstituted and substituted amines, e.g., a moiety that can be represented by the general formulas —NH₂, —NHR, —NRR", where R and R' are alkyl, cycloalkyl, aryl, or heterocyclyl groups, as example.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like.

The term "ether" as used herein refers to two hydrocarbons groups covalently linked by an oxygen atom.

The term "sulfonamido" is art recognized and includes a moiety that can be represented by the general formula —SO₂—N (R)(R') wherein where R, and R' are alkyl, cycloalkyl, aryl, or heterocyclyl groups, as examples.

The term "sulfonyl", as used herein, refers to a moiety that can be represented by the general formula —SO₂R wherein where R is an alkyl, cycloalkyl, aryl, or heterocyclyl group, as examples.

As used herein, the definition of each expression, e.g., alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. The phrase "protecting group" as used herein means temporary substituents which protect a potentially reactive functional group from undesired chemical transformations. Examples of such protecting groups include carbamates of amines, esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, 2nd ed.; Wiley: New York, 1991).

The term "Example" as used herein indicates the procedures followed for the preparation of a claimed compound, In general, the compounds of the present invention may be prepared by the methods illustrated in the general reaction schemes as, for example, described in the examples, or by modifications thereof, using readily available starting materials, reagents and conventional synthesis procedures not mentioned here.

The invention provides, in various embodiments a compound of formula A, B, or C

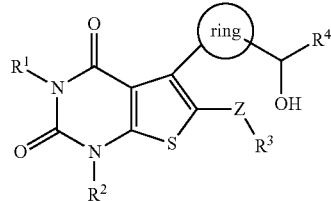

A

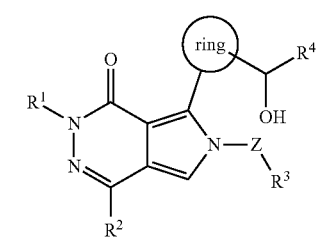

B

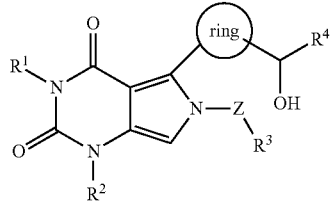

C wherein:

$R^1$ is selected from the group consisting of hydrogen, $(C_1-C_6)$alkyl, $(C_3-C_6)$branched alkyl, $(C_3-C_7)$cycloalkyl, and $(C_1-C_6)$fluoroalkyl;

$R^2$ is selected from the group consisting of hydrogen, $(C_1-C_6)$alkyl, $(C_3-C_6)$branched alkyl, $(C_3-C_7)$cycloalkyl, $(C_1-C_6)$fluoroalkyl, a $(C_6-C_{10})$aryl ring system, a 5- to 9-membered heteroaryl ring system, a $(C_1-C_6)$alkyl-$(C_6-C_{10})$aryl ring system, and a $(C_1-C_6)$alkyl-(5- to 9-membered)heteroaryl ring system;

provided that when $R^2$ comprises an aryl or heteroaryl ring system, the ring system bears 0-2 independently selected substituents from the group consisting of fluoro, chloro, trifluoromethyl, $(C_1-C_6)$alkoxy, and $(C1-C_6)$fluoroalkoxy;

$R^3$ is a monocyclic or bicyclic (C6-C10) aryl or a monocyclic or bicyclic (5- to 10-membered) heteroaryl group, wherein the aryl or heteroaryl can be substituted or unsubstituted;

$R^4$ is hydrogen, $(C_1-C_6)$alkyl, $(C_3-C_6)$branched alkyl, $(C_3-C7)$cycloalkyl, $(C_6-C_{10})$aryl, (5- to 7-membered)heteroaryl, or (4- to 7-membered) saturated heterocyclyl with 1-2 instances of heteroatoms selected from the group consisting of NH, NMe, O, and S;

for structure A, Z is $CH_2$, $CH((C_1-C_6)$alkyl), $CH((C_3-C_7)$ cycloalkyl), O, N, S, S(O), or $SO_2$;

for structures B and C, Z is $CH_2$, $CH((C_1-C_6)$alkyl), $CH((C_3-C_7)$cycloalkyl), or O;

n=1, 2, or 3;

the cyclic group indicated as "ring" is an aryl or heteroaryl group of any one of the following:

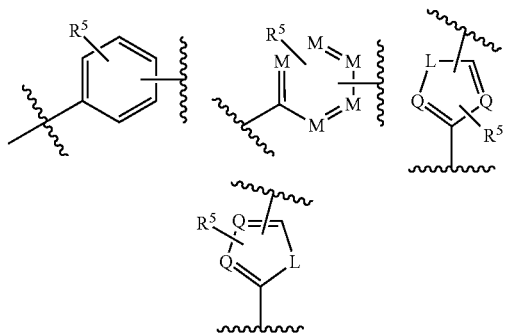

wherein wavy lines indicate points of bonding, and wherein M is independently selected CH or N, provided that M group can be a nitrogen atom in 0, 1, or 2, instances;

L is S, O, NH, $N(C_1-C_6)$alkyl, or $NCF_3$;

each Q is independently CH or N;

wherein $R^5$ is optionally present, when present, $R^5$ is one to four instances of independently selected F, Cl, Br, $CF_3$, $(C_1-C_6)$alkyl, $OCF_3$, $O(C_1-C_6)$alkyl, or CO—$(C_1-C_6)$alkyl;

or, the cyclic group indicated as "ring" is a $(C_3\text{-}C_7)$cycloalkyl or a saturated (3- to 7-membered)heterocyclyl comprising 1-2 heteroatoms selected from the group consisting of O, NH, N(C1-C6)alkyl, and N(C1-C6)fluoroalkyl; wherein the points of bonding may be cis or trans; wherein $R^5$ is optionally present, when present, $R^5$ is one to four instances of independently selected F, Cl, Br, $CF_3$, $(C_1\text{-}C_6)$alkyl, $OCF_3$, $O(C_1\text{-}C_6)$alkyl, or CO—$(C_1\text{-}C_6)$alkyl;

or a pharmaceutically acceptable salt thereof.

For example, in various embodiments, for a compound of the invention, when the $R^3$ group is monocyclic, the core ring system can consist of 5 or 6 atoms in total, with 1-6 carbon atoms, 0-4 nitrogen atoms, 0-2 oxygen atoms, and 0-1 sulfur atoms, A few representative examples are shown below:

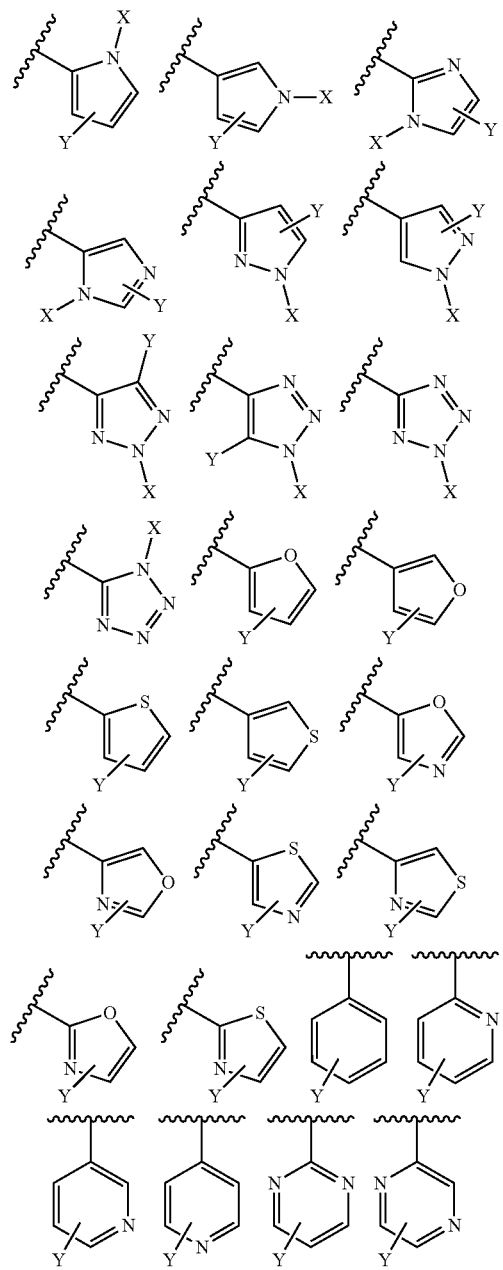

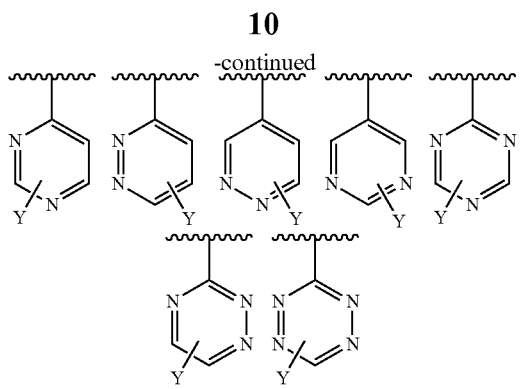

wherein X is H, $(C_1\text{-}C_6)$alkyl, or $CF_3$; and

Y is optionally present and, when Y is present, Y is 1-3 instances of a substituent selected from the group consisting of F, Cl, Br, $CF_3$, $(C_1\text{-}C_6)$alkyl, $O(C_1\text{-}C_6)$alkyl, $NH_2$, $NH(C_1\text{-}C_6)$alkyl, $N((C_1\text{-}C_6)$alkyl$)_2$, NH—$(CH_2)_j$—$CH_2$-Q, and

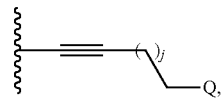

wherein j=2-6 and Q is one of the following groups

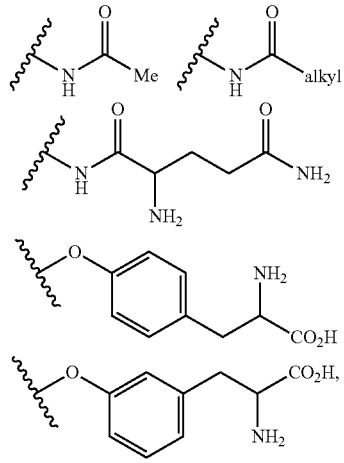

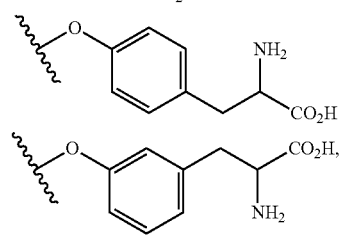

wherein a wavy line indicates a point of bonding.

When the $R^3$ group is bicyclic, the core ring system can consist of 9 or 10 atoms, with 4-10 carbon atoms, 0-6 nitrogen atoms, 0-2 oxygen atoms, and 0-2 sulfur atoms.

Representative examples of 9-atom ring systems are shown below:

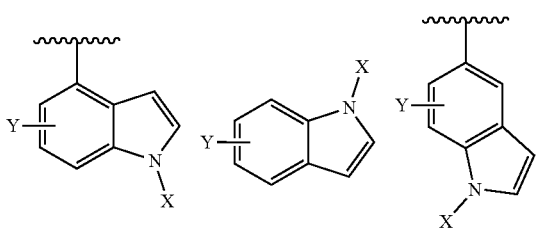

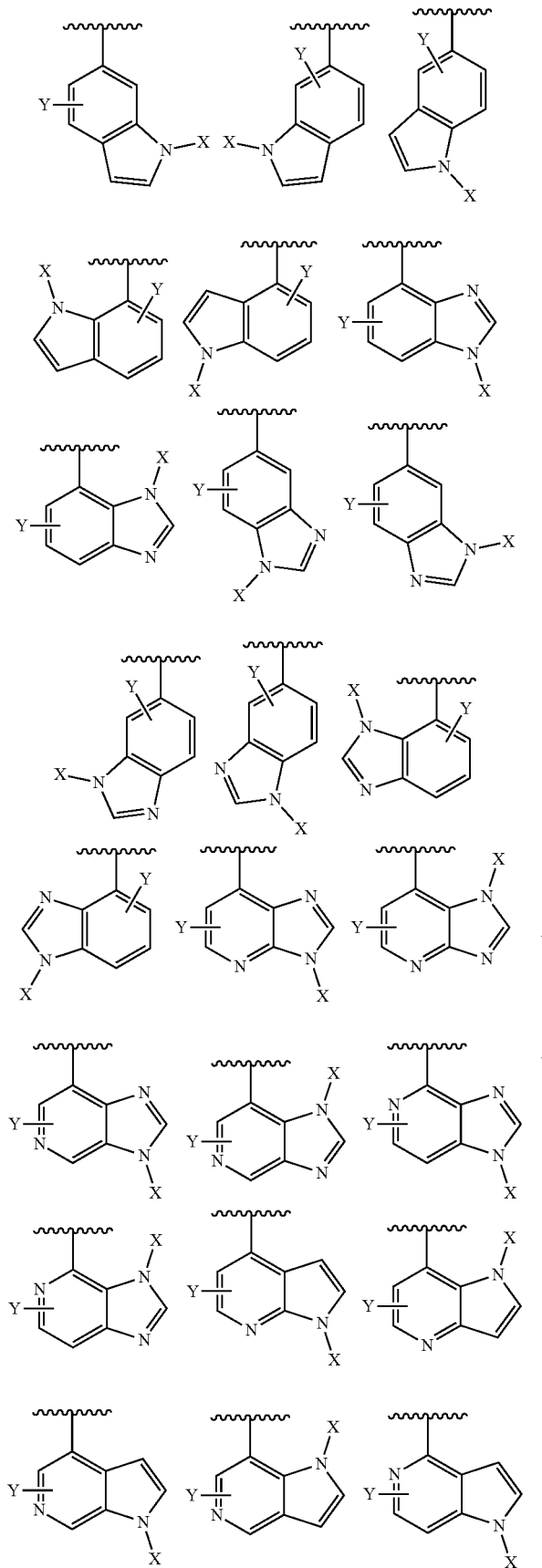
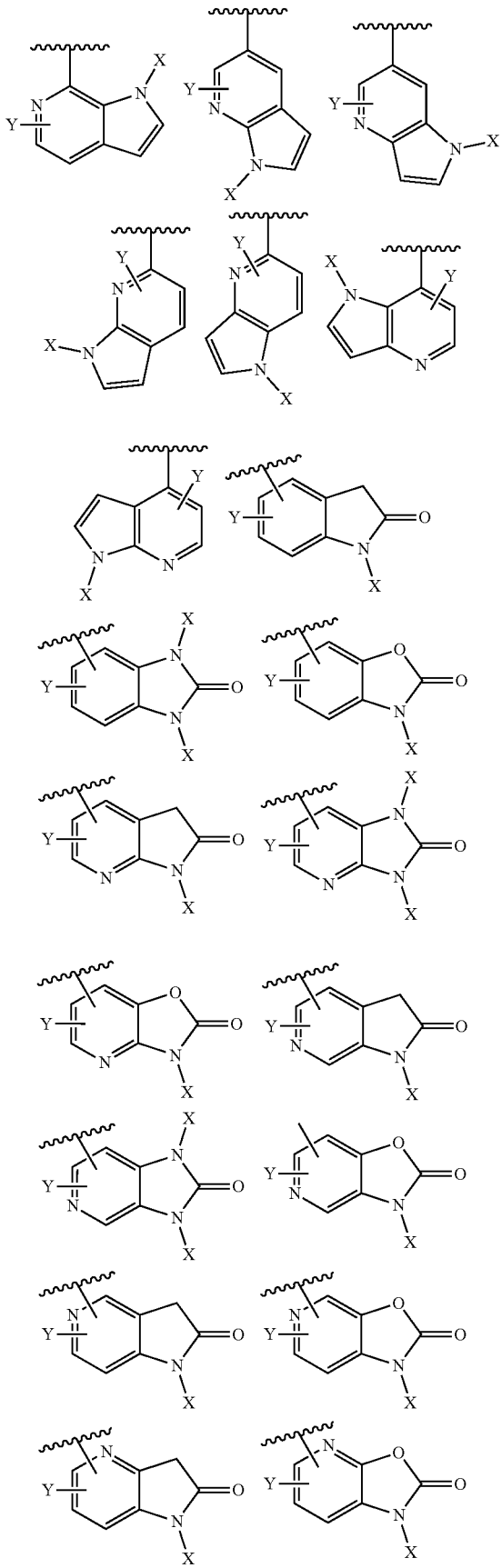

-continued
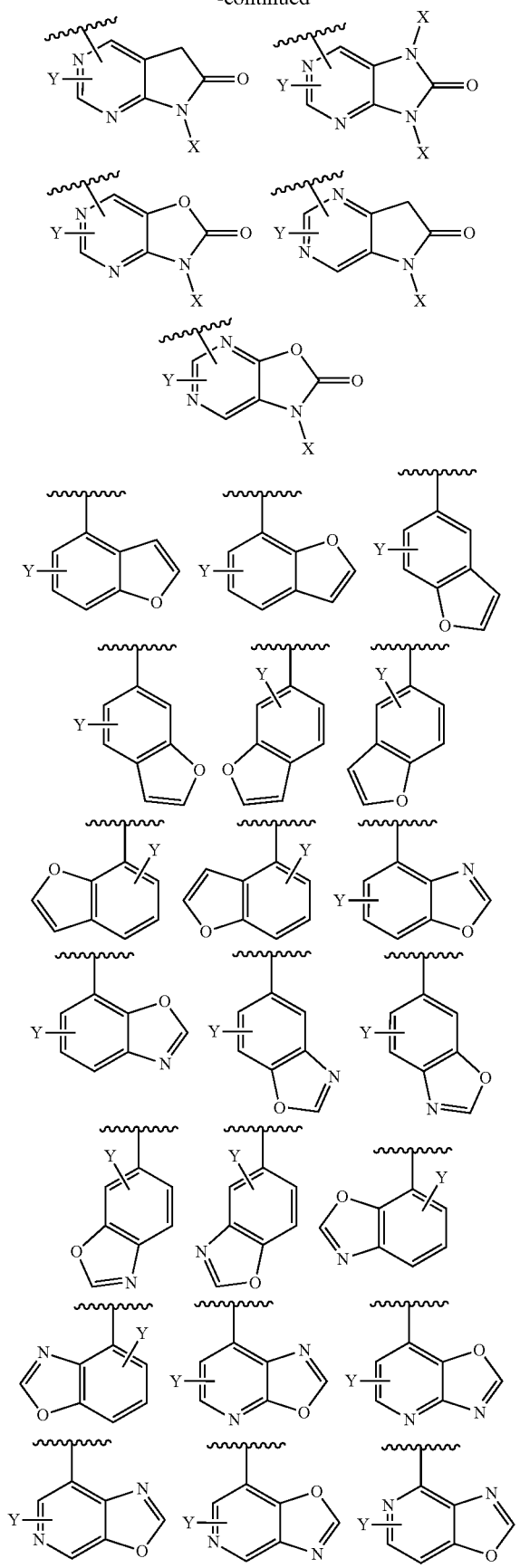
-continued
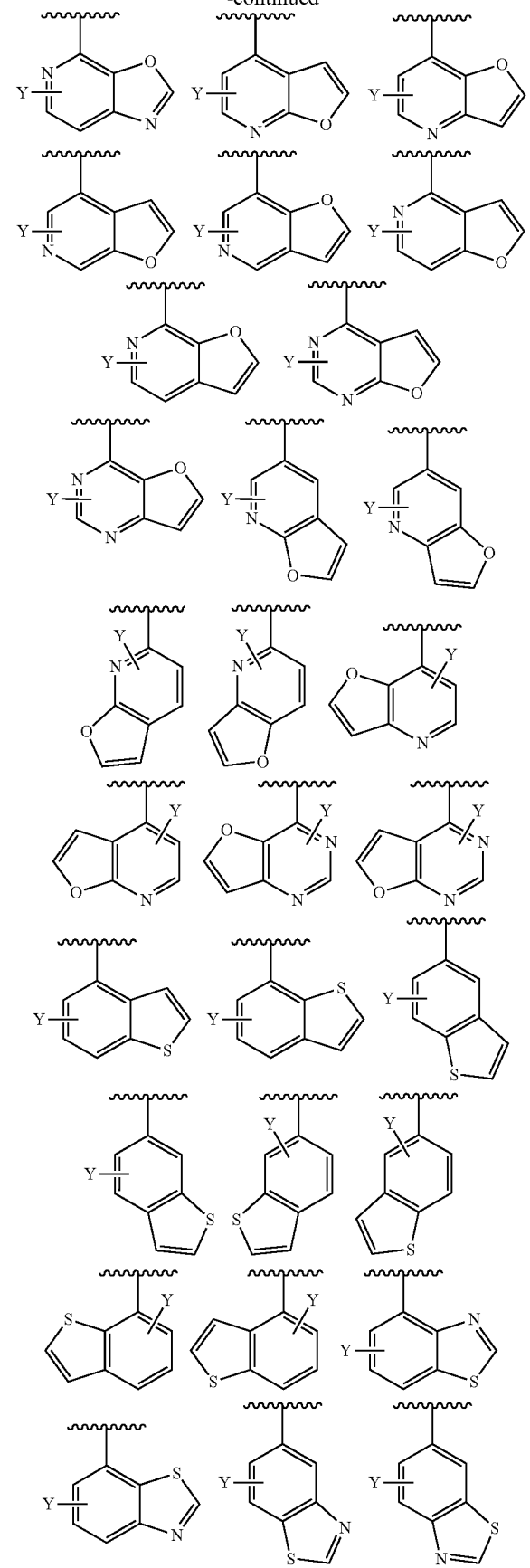

-continued

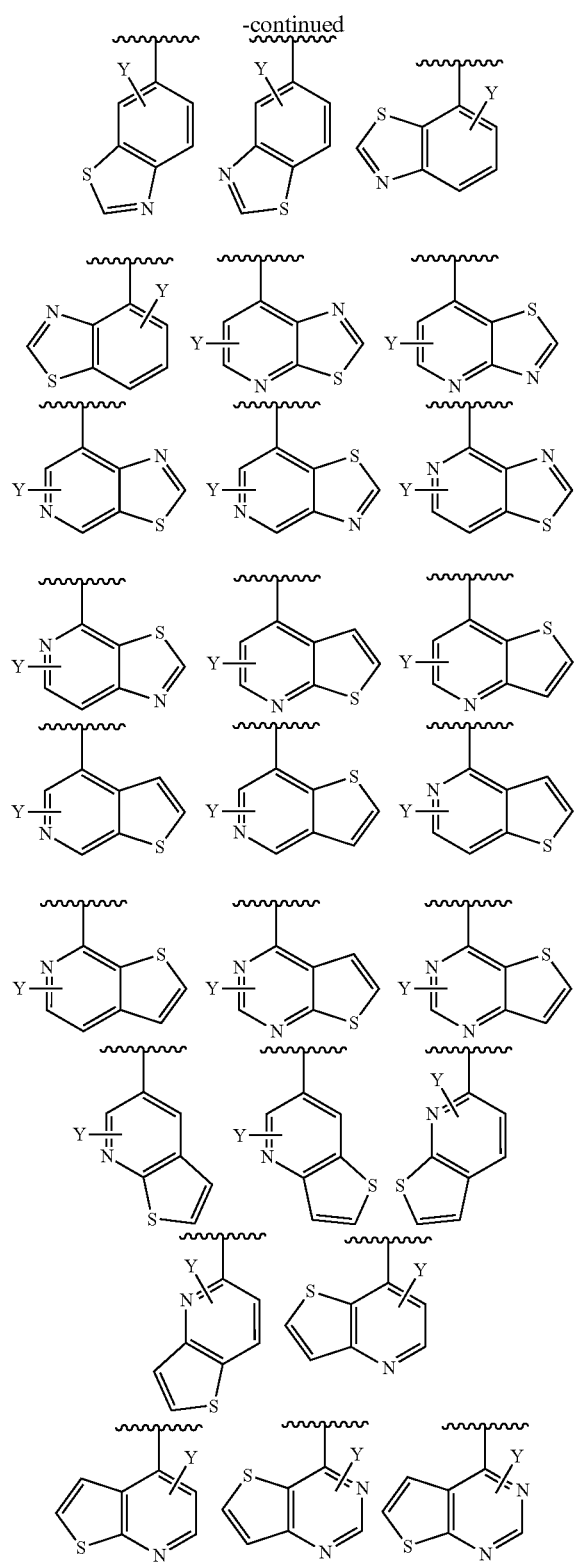

wherein the group X is H, (C₁-C₆)alkyl, or CF₃; and
Y is optionally present and, when Y is present, Y is 1-3 instances of a substituent selected from the group consisting of F, Cl, Br, CF₃, (C₁-C₆)alkyl, O(C₁-C₆)alkyl, NH₂, NH(C₁-C₆)alkyl, N((C₁-C₆)alkyl)₂, NH—(CH₂)$_j$—CH₂-Q, and

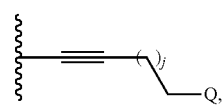

wherein j=2-6 and Q is one of the following groups

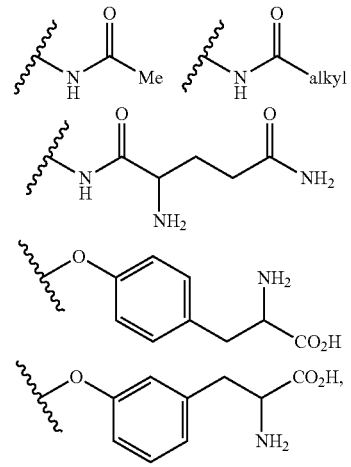

wherein a wavy line indicates a point of bonding, and wherein Y can be disposed on any ring of a multi-ring system.

Representative examples of 10-atom ring systems are shown below:

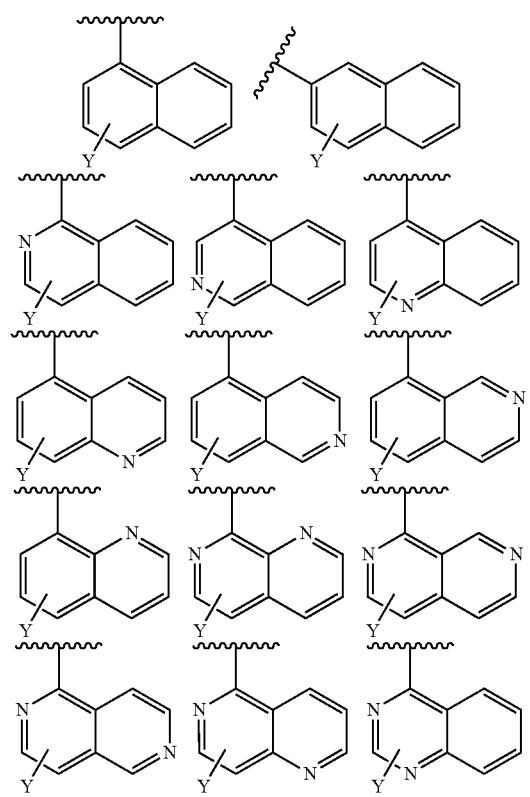

-continued

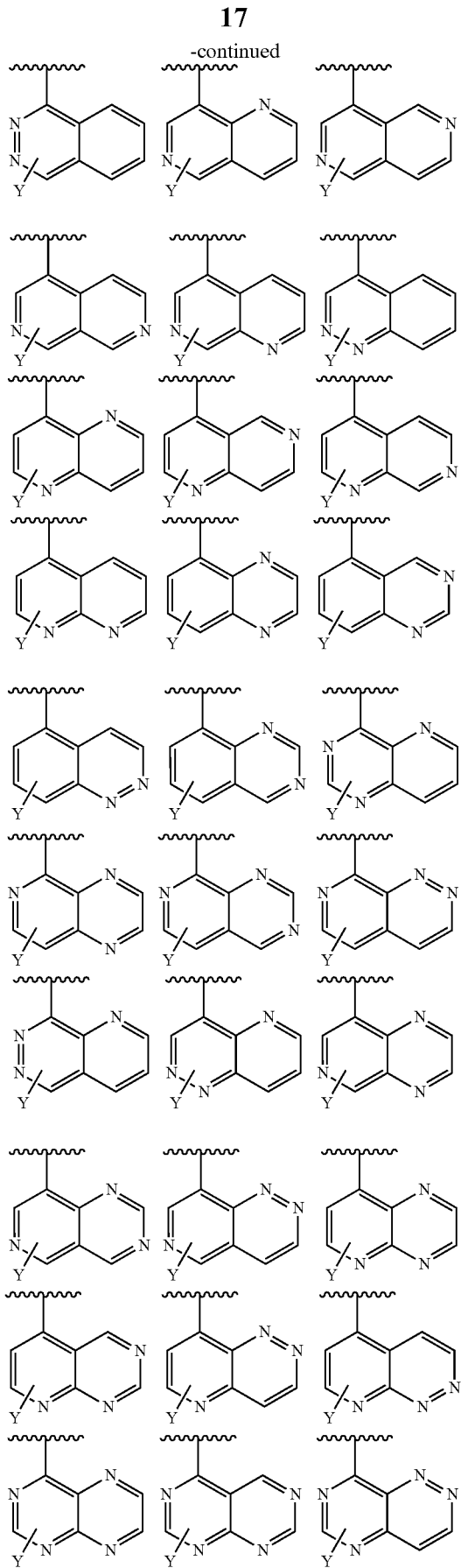

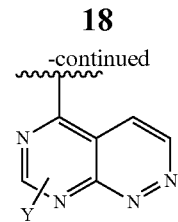

wherein the group X is H, $(C_1-C_6)$alkyl, or $CF_3$; and

Y is optionally present and, when Y is present, Y is 1-3 instances of a substituent selected from the group consisting of F, Cl, Br, $CF_3$, $(C_1-C_6)$alkyl, $O(C_1-C_6)$alkyl, $NH_2$, $NH(C_1-C_6)$alkyl, $N((C_1-C_6)$alkyl$)_2$, $NH-(CH_2)_j-CH_2-Q$, and

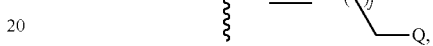

wherein j=2-6 and Q is one of the following groups

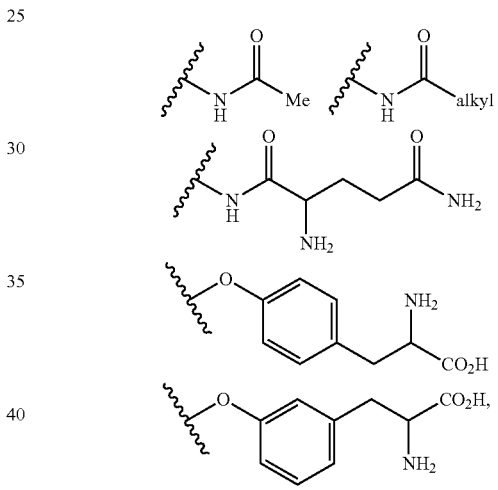

wherein a wavy line indicates a point of bonding, and wherein Y can be disposed on any ring of a multi-ring system.

EXAMPLES

Chemistry Methods

All reactions were performed in flame-dried glassware fitted with rubber septa under positive pressure of nitrogen or argon, unless otherwise noted. Tetrahydrofuran, DMF, acetonitrile, and methylene chloride were purchased from Aldrich and used as received.

Commercially available reagents were used without further purification. Thin layer chromatography (TLC) analyses were performed on pre-coated 250 μM silica 60 F254 glass-backed plates. Flash chromatography was performed on pre-packed columns of silica gel (230-400 mesh, 40-63 μm) by CombiFlash with EA/hexane or MeOH/DCM as eluents. Preparative HPLC was performed on a Shimadzu LC-8A preparative HPLC instrument on SunFire $C_{18}$ OBD 10 μm (30×250 mm) with $CH_3CN$+50% $MeOH/H_2O$+0.1% TFA as eluents to purify the targeted compounds. LC-MS was performed on Agilent Technologies 1200 series analytical HPLC instrument paired with a 6140 quadrupole mass spectrometer or with a Thermo Scientific UltiMate 3000 mass spectrometer. Analytical HPLC was performed on Agilent technologies 1200 series with $CH_3CN$ (Solvent B)/$H_2O$+0.9% $CH_3CN$+0.1% TFA (solvent A) as eluents, and the targeted products were detected by UV in the detection range of 215-310 nm, $^1F1$ and $^{13}C$ NMR spectra were recorded on a Bruker NMR spectrometer at 400 MHz ($^1H$) or 100 MHz ($^{13}C$). Unless otherwise specified, $CDCl_3$ was used as the NMR solvent, Resonances were reported in parts per million downfield from TMS standard, and were referenced to either the residual solvent peak (typically $^1H$: $CHCl_3$ δ 7.27; $^{13}C$: $CDCl_3$ δ 77.23).

Certain abbreviations for common chemicals were used in the Examples and are defined as follows:
EA=ethyl acetate
ESI=Electrospray ionization mass spectroscopy
NMR=nuclear magnetic resonance spectroscopy
DMSO=dimethyl sulfoxide
DMF=N,N-dimethylformamide
Hex=hexanes
LC-MS=liquid chromatography-mass spectroscopy
HPLC=high performance liquid chromatography
NMO=N-methylmorpholine N-oxide
NMP=N-methyl pyrrolidinone
TEA=triethylamine
DIAD=diisopropyl azodicarboxylate
Tf=trifluoromethansulfonyl The following compounds are reported as specific examples:

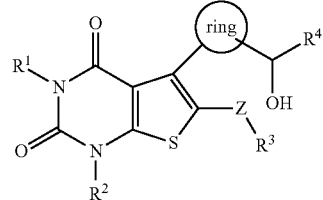 A

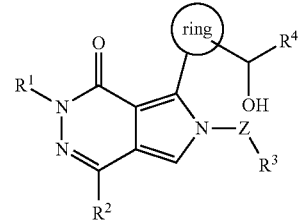 B

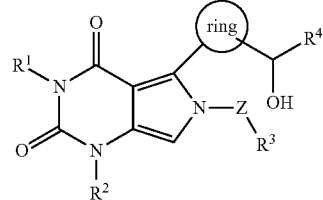 C

TABLE 1

| Example | chemical structure | type | internal ID# | groups present |
|---|---|---|---|---|
| 1 | 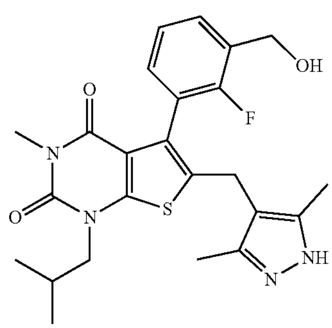 | A | 13219 | $R^1$ = Me, $R^2$ = i-Pr, $R^4$ = H<br><br>$R^3$ = (4-pyrazolyl with each X = Me)<br><br>wherein each X = Me<br>ring = phenyl,<br>$R^5$ = F<br>Z = $CH_2$ |
| 2 | 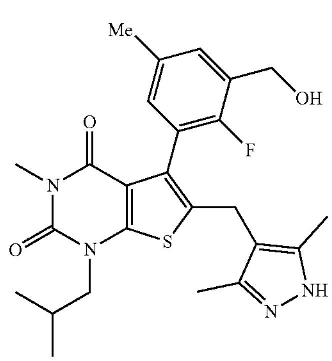 | A | 14280 | $R^1$ = Me, $R^2$ = i-Pr, $R^4$ = H<br><br>$R^3$ = (4-pyrazolyl with each X = Me)<br><br>wherein each X = Me<br>ring = phenyl,<br>$R^5$ = Me, F<br>Z = $CH_2$ |

TABLE 1-continued

| Example | chemical structure | type | internal ID# | groups present |
|---|---|---|---|---|
| 3 | 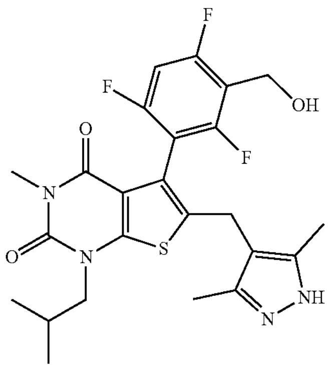 | A | 14018 | $R^1$ = Me, $R^2$ = i-Pr, $R^4$ = H; $R^3$ = pyrazolyl with each X = Me; ring = phenyl, $R^5$ = F, F, F; Z = $CH_2$ |
| 4 | 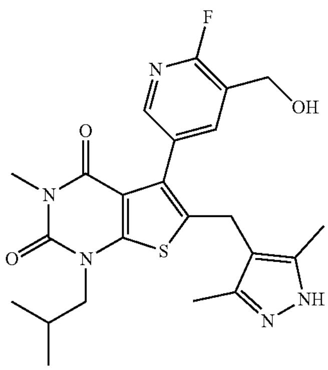 | A | 14020 | $R^1$ = Me, $R^2$ = i-Pr, $R^4$ = H; $R^3$ = pyrazolyl with each X = Me; ring = pyridyl, $R^5$ = F; Z = $CH_2$ |
| 5 | 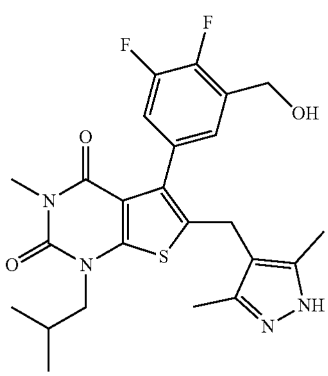 | A | 13939 | $R^1$ = Me, $R^2$ = i-Pr, $R^4$ = H; $R^3$ = pyrazolyl with each X = Me; ring = phenyl, $R^5$ = F, F; Z = $CH_2$ |
| 6 | 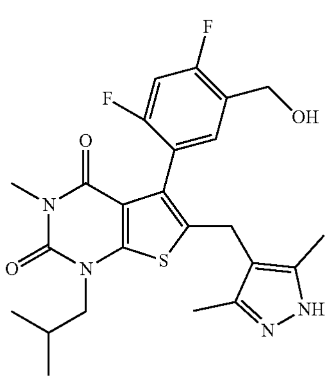 | A | 13778 | $R^1$ = Me, $R^2$ = i-Pr, $R^4$ = H; $R^3$ = pyrazolyl with each X = Me; ring = phenyl, $R^5$ = F, F; Z = $CH_2$ |

TABLE 1-continued

| Example | chemical structure | type | internal ID# | groups present |
|---|---|---|---|---|
| 7 | 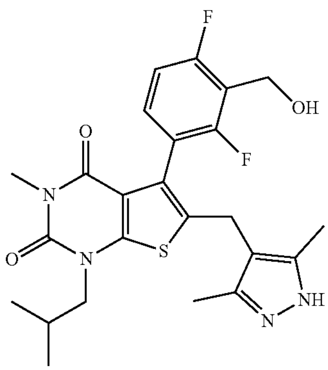 | A | 13218 | $R^1$ = Me, $R^2$ = i-Pr, $R^4$ = H; $R^3$ = 3,5-dimethyl-1H-pyrazol-4-yl (each X = Me); ring = phenyl, $R^5$ = F, F; Z = $CH_2$ |
| 8 | 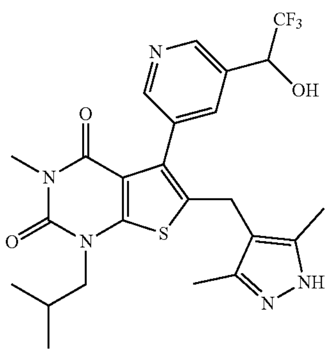 | A | 14162 | $R^1$ = Me, $R^2$ = i-Pr, $R^4$ = $CF_3$; $R^3$ = 3,5-dimethyl-1H-pyrazol-4-yl (each X = Me); ring = 3-pyridyl; Z = $CH_2$ |
| 9 | 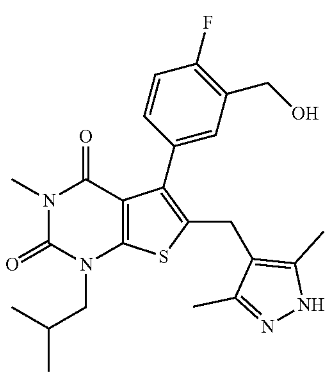 | A | 11105 | $R^1$ = Me, $R^2$ = i-Pr, $R^4$ = H; $R^3$ = 3,5-dimethyl-1H-pyrazol-4-yl (each X = Me); ring = phenyl, $R^5$ = F; Z = $CH_2$ |
| 10 | 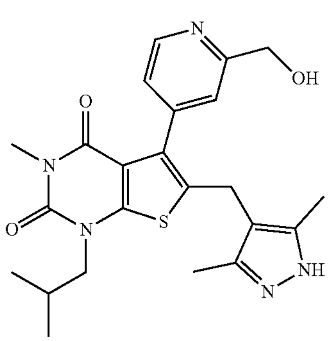 | A | 11057 | $R^1$ = Me, $R^2$ = i-Pr, $R^4$ = H; $R^3$ = 3,5-dimethyl-1H-pyrazol-4-yl (each X = Me); ring = pyridyl, $R^5$ = H; Z = $CH_2$ |

TABLE 1-continued

| Example | chemical structure | type | internal ID# | groups present |
|---|---|---|---|---|
| 11 | (structure) | A | 11104 | $R^1$ = Me, $R^2$ = i-Pr, $R^4$ = H; $R^3$ = (3,5-dimethylpyrazol-4-yl) wherein each X = Me; ring = phenyl, $R^5$ = F; Z = $CH_2$ |
| 12 | (structure) | A | 11058 | $R^1$ = Me, $R^2$ = i-Pr, $R^4$ = H; $R^3$ = (3,5-dimethylpyrazol-4-yl) wherein each X = Me; ring = pyridyl, $R^5$ = H; Z = $CH_2$ |
| 13 | (structure) | A | 10345 | $R^1$ = Me, $R^2$ = i-Pr, $R^4$ = Me; $R^3$ = (3,5-dimethylpyrazol-4-yl) wherein each X = Me; ring = phenyl, Z = $CH_2$ |
| 14 | (structure) | A | 10346 | $R^1$ = Me, $R^2$ = i-Pr, $R^4$ = $CF_3$; $R^3$ = (3,5-dimethylpyrazol-4-yl) wherein each X = Me; ring = phenyl, Z = $CH_2$ |

TABLE 1-continued

| Example | chemical structure | type | internal ID# | groups present |
|---|---|---|---|---|
| 15 | 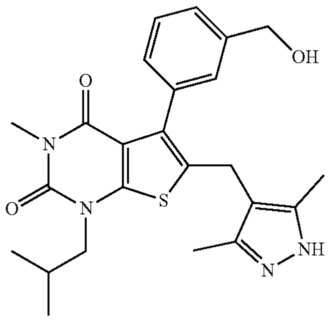 | A | 10267 | $R^1$ = Me, $R^2$ = i-Pr, $R^4$ = H; $R^3$ = pyrazolyl wherein each X = Me, ring = phenyl, Z = $CH_2$ |
| 16 | 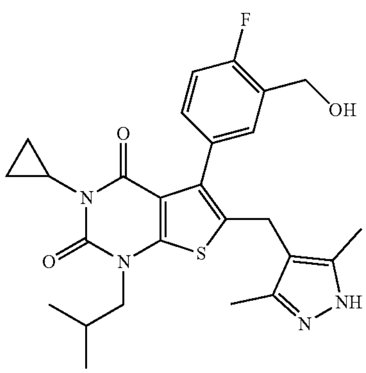 [SMILES: Cc1n[nH]c(C)c1Cc1sc2c(c1-c1ccc(F)c(CO)c1)c(=O)n(C1CC1)c(=O)n2CC(C)C] | A | 14163 | $R^1$ = cyclopropyl, $R^2$ = i-Pr, $R^4$ = H; $R^3$ = pyrazolyl wherein each X = Me, ring = phenyl, $R^5$ = F, Z = $CH_2$ |
| 17 | 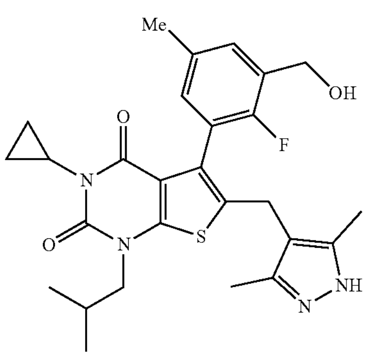 [SMILES: Cc1cc(CO)c(F)c(-c2c(Cc3c(C)n[nH]c3C)sc3c2c(=O)n(C2CC2)c(=O)n3CC(C)C)c1] | A | 14281 | $R^1$ = cyclopropyl, $R^2$ = i-Pr, $R^4$ = H; $R^3$ = pyrazolyl wherein each X = Me, ring = phenyl, $R^5$ = Me, F, Z = $CH_2$ |
| 18 | 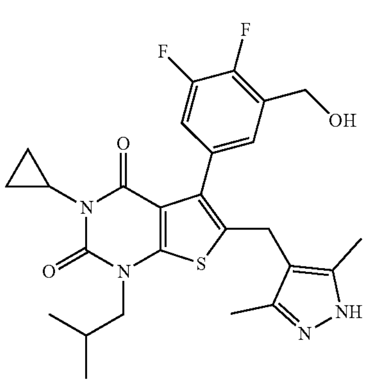 [SMILES: Cc1n[nH]c(C)c1Cc1sc2c(c1-c1cc(F)c(F)c(CO)c1)c(=O)n(C1CC1)c(=O)n2CC(C)C] | A | 14019 | $R^1$ = cyclopropyl, $R^2$ = i-Pr, $R^4$ = H; $R^3$ = pyrazolyl wherein each X = Me, ring = phenyl, $R^5$ = F, F, Z = $CH_2$ |

TABLE 1-continued

| Example | chemical structure | type | internal ID# | groups present |
|---|---|---|---|---|
| 19 | 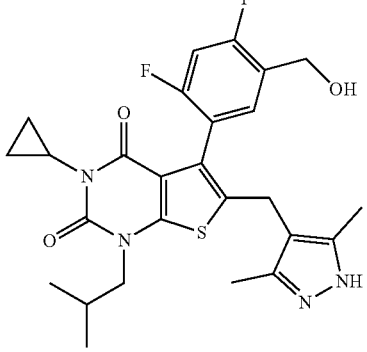 | A | 13938 | $R^1$ = cyclopropyl, $R^2$ = i-Pr, $R^4$ = H<br>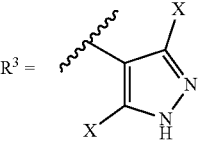<br>wherein each X = Me<br>ring = phenyl,<br>$R^5$ = F, F<br>Z = $CH_2$ |
| 20 | 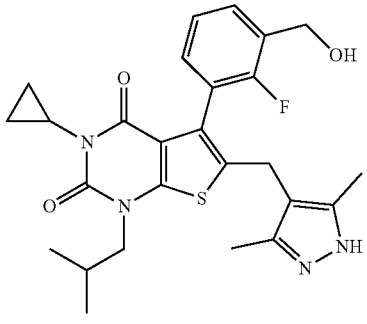 [SMILES: Cc1n[nH]c(C)c1Cc1sc2c(c1-c1cccc(CO)c1F)c(=O)n(C1CC1)c(=O)n2CC(C)C] | A | 13780 | $R^1$ = cyclopropyl, $R^2$ = i-Pr, $R^4$ = H<br>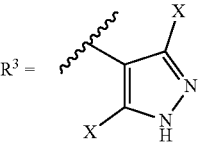<br>wherein each X = Me<br>ring = phenyl,<br>$R^5$ = F<br>Z = $CH_2$ |
| 21 | 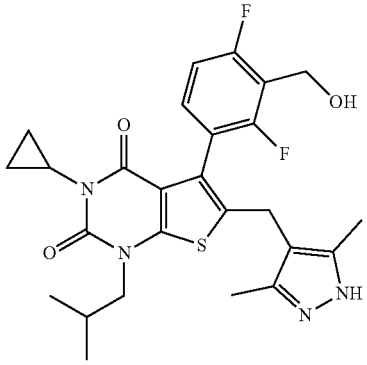 [SMILES: Cc1n[nH]c(C)c1Cc1sc2c(c1-c1ccc(F)c(CO)c1F)c(=O)n(C1CC1)c(=O)n2CC(C)C] | A | 13779 | $R^1$ = cyclopropyl, $R^2$ = i-Pr, $R^4$ = H<br>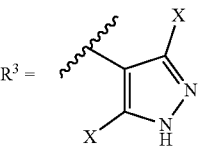<br>wherein each X = Me<br>ring = phenyl,<br>$R^5$ = F, F<br>Z = $CH_2$ |
| 22 | 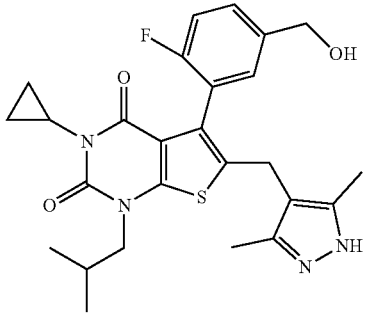 [SMILES: Cc1n[nH]c(C)c1Cc1sc2c(c1-c1cc(CO)ccc1F)c(=O)n(C1CC1)c(=O)n2CC(C)C] | A | 11241 | $R^1$ = cyclopropyl, $R^2$ = i-Pr, $R^4$ = H<br>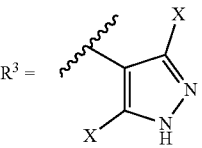<br>wherein each X = Me<br>ring = phenyl,<br>$R^5$ = F<br>Z = $CH_2$ |

TABLE 1-continued

| Example | chemical structure | type | internal ID# | groups present |
|---|---|---|---|---|
| 23 | 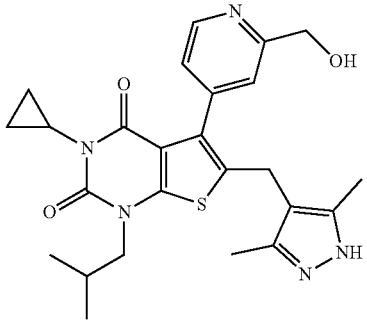 [SMILES: Cc1n[nH]c(C)c1Cc1sc2c(c1-c1ccnc(CO)c1)c(=O)n(C1CC1)c(=O)n2CC(C)C] | A | 11293 | $R^1$ = cyclopropyl, $R^2$ = i-Pr, $R^4$ = H<br>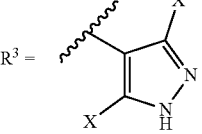<br>wherein each X = Me<br>ring = pyridyl,<br>$R^5$ = H<br>Z = $CH_2$ |
| 24 | 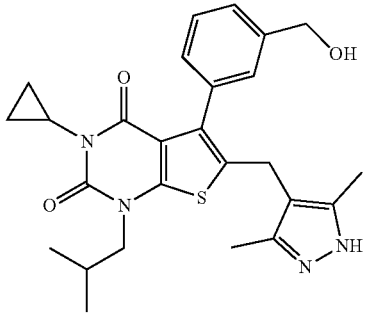 [SMILES: Cc1n[nH]c(C)c1Cc1sc2c(c1-c1cccc(CO)c1)c(=O)n(C1CC1)c(=O)n2CC(C)C] | A | 11213 | $R^1$ = cyclopropyl, $R^2$ = i-Pr, $R^4$ = H<br>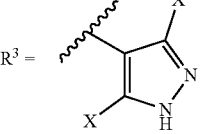<br>wherein each X = Me<br>ring = phenyl,<br>$R^5$ = H<br>Z = $CH_2$ |
| 25 | 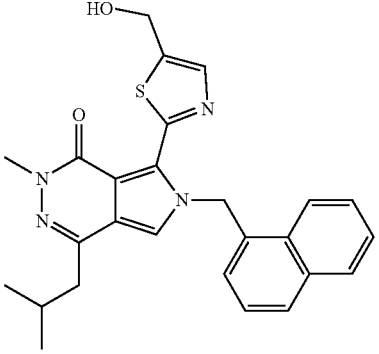 [SMILES: CC(C)Cc1nn(C)c(=O)c2c(-c3ncc(CO)s3)n(Cc3cccc4ccccc34)cc12] | B | 10366 | $R^1$ = Me, $R^2$ = i-Pr, $R^4$ = H<br>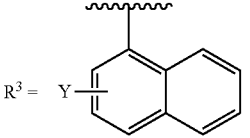<br>wherein Y = H<br>ring = 2-thiazole<br>Z = $CH_2$ |
| 26 | 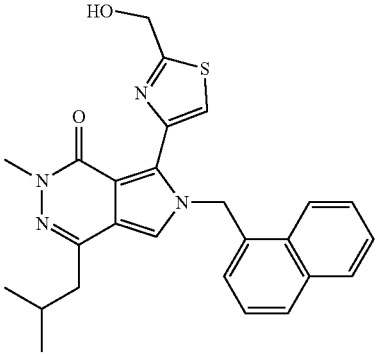 [SMILES: CC(C)Cc1nn(C)c(=O)c2c(-c3csc(CO)n3)n(Cc3cccc4ccccc34)cc12] | B | 10385 | $R^1$ = Me, $R^2$ = i-Pr, $R^4$ = H<br>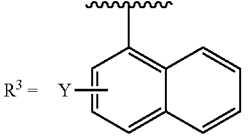<br>wherein Y = H<br>ring = 3-thiazole<br>Z = $CH_2$ |

TABLE 1-continued

| Example | chemical structure | type | internal ID# | groups present |
|---|---|---|---|---|
| 27 | (structure) | B | 10263 | $R^1$ = Me, $R^2$ = i-Pr, $R^4$ = H; $R^3$ = 1-naphthylmethyl (Y = H); ring = phenyl, $R^5$ = F, F; Z = $CH_2$ |
| 28 | (structure) | B | 10154 | $R^1$ = Me, $R^2$ = i-Pr, $R^4$ = H; $R^3$ = 1-naphthylmethyl (Y = H); ring = phenyl, $R^5$ = F; Z = $CH_2$ |
| 29 | (structure) | B | 10155 | $R^1$ = Me, $R^2$ = i-Pr, $R^4$ = H; $R^3$ = 1-naphthylmethyl (Y = H); ring = phenyl, $R^5$ = F; Z = $CH_2$ |
| 30 | (structure) | B | 10156 | $R^1$ = Me, $R^2$ = i-Pr, $R^4$ = H; $R^3$ = 1-naphthylmethyl (Y = H); ring = phenyl, $R^5$ = Cl; Z = $CH_2$ |

TABLE 1-continued

| Example | chemical structure | type | internal ID# | groups present |
|---|---|---|---|---|
| 31 | 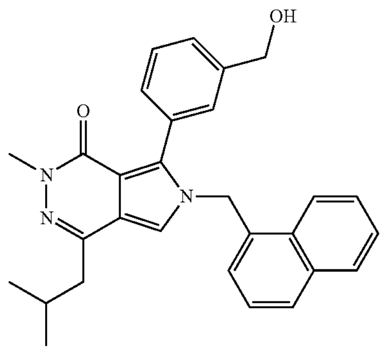 [SMILES: CC(C)Cc1nn(C)c(=O)c2c(-c3cccc(CO)c3)n(Cc3cccc4ccccc34)cc12] | B | 10049 | $R^1$ = Me, $R^2$ = i-Pr, $R^4$ = H<br>$R^3$ = Y—(1-naphthyl)<br>wherein Y = H<br>ring = phenyl, $R^5$ = H<br>Z = $CH_2$ |
| 32 | 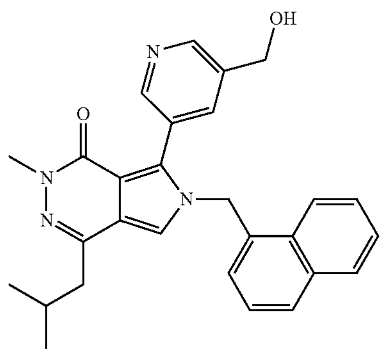 [SMILES: CC(C)Cc1nn(C)c(=O)c2c(-c3cncc(CO)c3)n(Cc3cccc4ccccc34)cc12] | B | 10050 | $R^1$ = Me, $R^2$ = i-Pr, $R^4$ = H<br>$R^3$ = Y—(1-naphthyl)<br>wherein Y = H<br>ring = pyridyl, $R^5$ = H<br>Z = $CH_2$ |
| 33 | 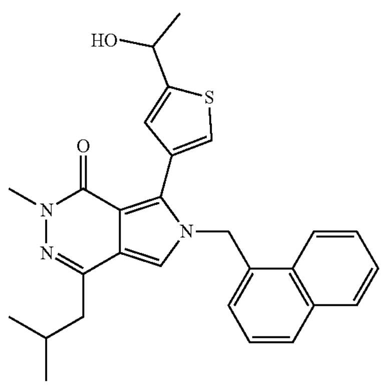 [SMILES: CC(C)Cc1nn(C)c(=O)c2c(-c3csc(C(C)O)c3)n(Cc3cccc4ccccc34)cc12] | B | 10384 | $R^1$ = Me, $R^2$ = i-Pr, $R^4$ = Me<br>$R^3$ = Y—(1-naphthyl)<br>wherein Y = H<br>ring = 3-thiophene<br>Z = $CH_2$ |
| 34 | 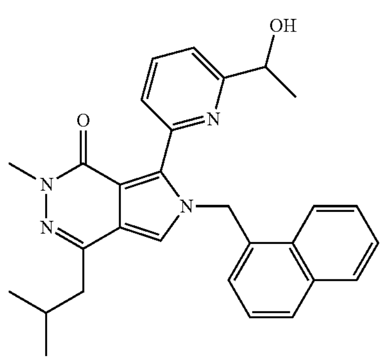 [SMILES: CC(C)Cc1nn(C)c(=O)c2c(-c3cccc(C(C)O)n3)n(Cc3cccc4ccccc34)cc12] | B | 10383 | $R^1$ = Me, $R^2$ = i-Pr, $R^4$ = Me<br>$R^3$ = Y—(1-naphthyl)<br>wherein Y = H<br>ring = pyridyl<br>Z = $CH_2$ |

TABLE 1-continued

| Example | chemical structure | type | internal ID# | groups present |
|---|---|---|---|---|
| 35 | 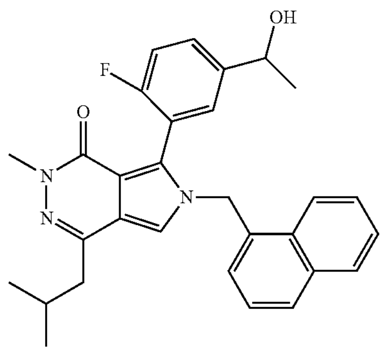 [SMILES: CC(C)Cc1nn(C)c(=O)c2c(-c3cc(C(C)O)ccc3F)n(Cc3cccc4ccccc34)cc12] | B | 10367 | $R^1$ = Me, $R^2$ = i-Pr, $R^4$ = Me<br><br>$R^3$ = naphthalen-1-yl (Y-substituted)<br><br>wherein Y = H<br>ring = phenyl, $R^5$ = F<br>Z = $CH_2$ |
| 36 | 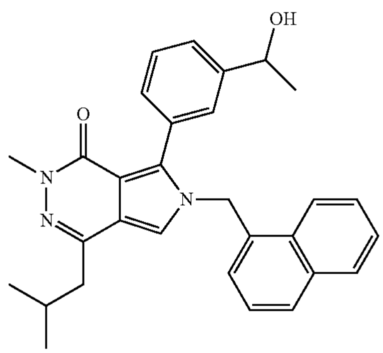 [SMILES: CC(C)Cc1nn(C)c(=O)c2c(-c3cccc(C(C)O)c3)n(Cc3cccc4ccccc34)cc12] | B | 10100 | $R^1$ = Me, $R^2$ = i-Pr, $R^4$ = Me<br><br>$R^3$ = naphthalen-1-yl (Y-substituted)<br><br>wherein Y = H<br>ring = phenyl, $R^5$ = H<br>Z = $CH_2$ |
| 37 | 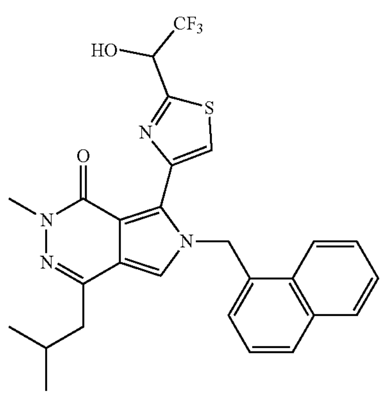 [SMILES: CC(C)Cc1nn(C)c(=O)c2c(-c3csc(C(O)C(F)(F)F)n3)n(Cc3cccc4ccccc34)cc12] | B | 10603 | $R^1$ = Me, $R^2$ = i-Pr, $R^4$ = $CF_3$<br><br>$R^3$ = naphthalen-1-yl (Y-substituted)<br><br>wherein Y = H<br>ring = 3-thiazole<br>Z = $CH_2$ |
| 38 | 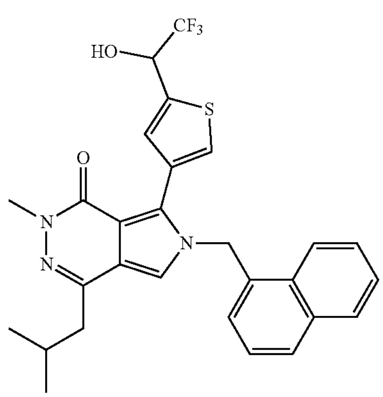 [SMILES: CC(C)Cc1nn(C)c(=O)c2c(-c3csc(C(O)C(F)(F)F)c3)n(Cc3cccc4ccccc34)cc12] | B | 10501 | $R^1$ = Me, $R^2$ = i-Pr, $R^4$ = $CF_3$<br><br>$R^3$ = naphthalen-1-yl (Y-substituted)<br><br>wherein Y = H<br>ring = 3-thiophene<br>Z = $CH_2$ |

TABLE 1-continued

| Example | chemical structure | type | internal ID# | groups present |
|---|---|---|---|---|
| 39 | 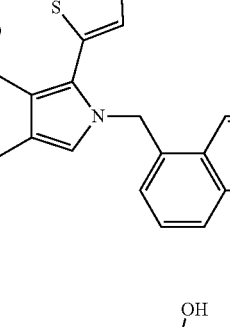 | B | 10426 | $R^1$ = Me, $R^2$ = i-Pr, $R^4$ = $CF_3$<br><br>$R^3$ = Y—[1-naphthyl]<br><br>wherein Y = H<br>ring = 2-thiophene<br>Z = $CH_2$ |
| 40 | 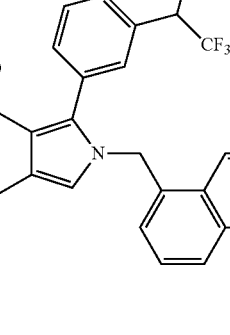 | B | 10344 | $R^1$ = Me, $R^2$ = i-Pr, $R^4$ = $CF_3$<br><br>$R^3$ = Y—[1-naphthyl]<br><br>wherein Y = H<br>ring = phenyl, $R^5$ = H<br>Z = $CH_2$ |
| 41 | 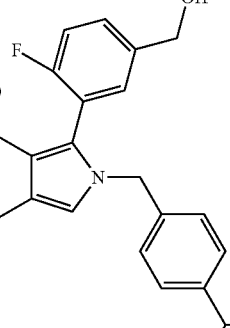 | B | 10264 | $R^1$ = Me, $R^2$ = i-Pr,<br>$R^4$ = H<br><br>$R^3$ = Y—[phenyl]<br><br>wherein Y = p-Ph<br>ring = phenyl, $R^5$ = F<br>Z = $CH_2$ |
| 42 | 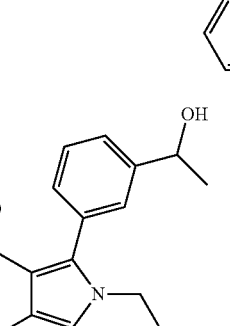 | B | 10265 | $R^1$ = Me, $R^2$ = i-Pr,<br>$R^4$ = Me<br><br>$R^3$ = Y—[phenyl]<br><br>wherein Y = p-Ph<br>ring = phenyl, $R^5$ = H<br>Z = $CH_2$ |

TABLE 1-continued

| Example | chemical structure | type | internal ID# | groups present |
|---|---|---|---|---|
| 43 | 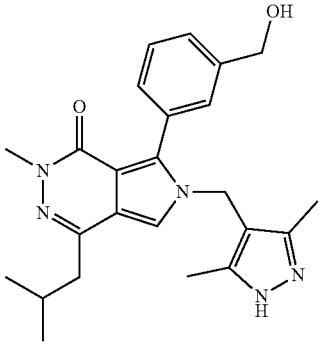 | B | 10318 | $R^1$ = Me,<br>$R^2$ = i-Pr, $R^4$ = H<br>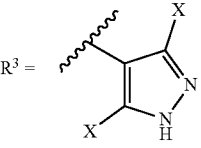<br>wherein X = Me<br>ring = phenyl<br>Z = $CH_2$ |
| 44 | 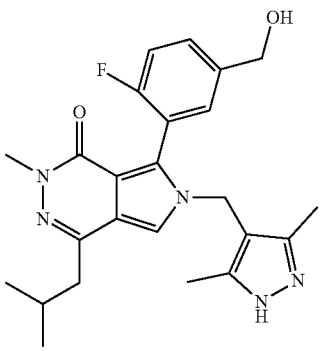 | B | 10317 | $R^1$ = Me,<br>$R^2$ = i-Pr, $R^4$ = H<br>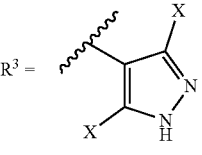<br>wherein X = Me<br>ring = phenyl,<br>$R^5$ = F<br>Z = $CH_2$ |
| 45 | 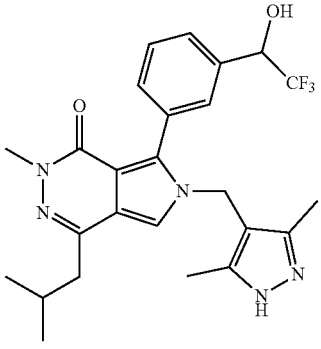 | B | 10430 | $R^1$ = Me,<br>$R^2$ = i-Pr, $R^4$ = $CF_3$<br>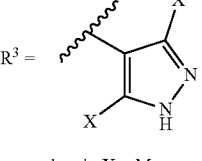<br>wherein X = Me<br>ring = phenyl<br>Z = $CH_2$ |
| 46 | 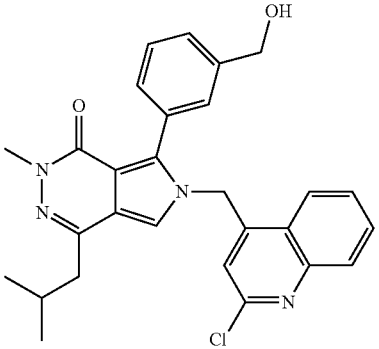 [SMILES: CC(C)Cc1nn(C)c(=O)c2c(-c3cccc(CO)c3)n(Cc3cc(Cl)nc4ccccc34)cc12] | B | 13990 | $R^1$ = Me, $R^2$ = i-Pr, $R^4$ = H<br>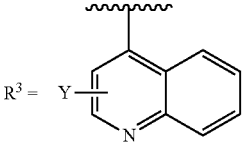<br>wherein Y = Cl<br>ring = phenyl<br>Z = $CH_2$ |

TABLE 1-continued

| Example | chemical structure | type | internal ID# | groups present |
|---|---|---|---|---|
| 47 | 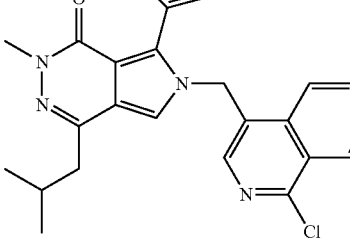 | B | 11718 | $R^1$ = Me, $R^2$ = i-Pr, $R^4$ = H<br><br>$R^3$ = isoquinolin-4-yl<br>wherein Y = Cl<br>ring = phenyl<br>Z = $CH_2$ |
| 48 | 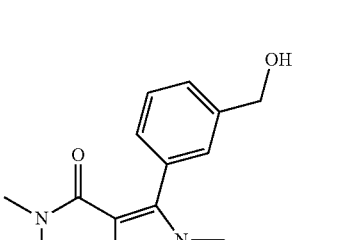 | B | 14078 | $R^1$ = Me, $R^2$ = i-Pr,<br>$R^4$ = H<br><br>$R^3$ = phenyl<br>wherein Y = Cl<br>ring = phenyl<br>Z = $CH_2CH_2O$ |
| 49 | 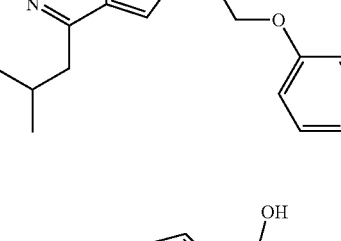 | B | 13991 | $R^1$ = Me, $R^2$ = i-Pr, $R^4$ = H<br><br>$R^3$ = quinolin-4-yl<br>wherein Y = $NH(CH_2)_5NH_2$<br>ring = phenyl<br>Z = $CH_2$ |
| 50 | 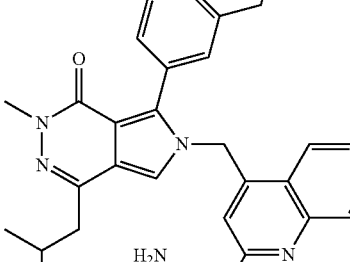 | B | 13459 | $R^1$ = Me, $R^2$ = i-Pr, $R^4$ = H<br><br>$R^3$ = isoquinolin-4-yl<br>wherein Y = $NH(CH_2)_5NH_2$<br>ring = phenyl<br>Z = $CH_2$ |

TABLE 1-continued

| Example | chemical structure | type | internal ID# | groups present |
|---|---|---|---|---|
| 51 | 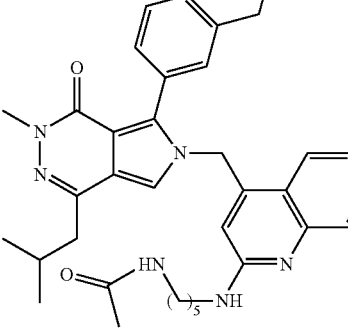 | B | 13718 | $R^1$ = Me, $R^2$ = i-Pr, $R^4$ = H<br><br>$R^3$ = 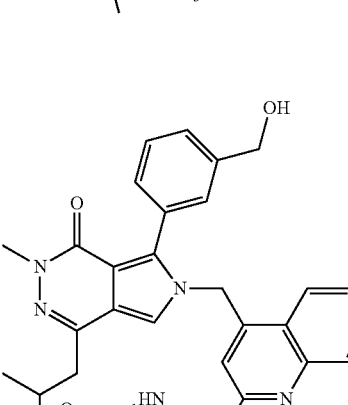<br><br>wherein Y =<br>$NH(CH_2)_5NH_2$—Ac<br>ring = phenyl<br>Z = $CH_2$ |
| 52 | 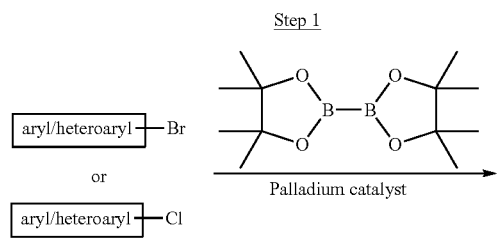 | B | 13758 | $R^1$ = Me, $R^2$ = i-Pr, $R^4$ = H<br><br>$R^3$ = 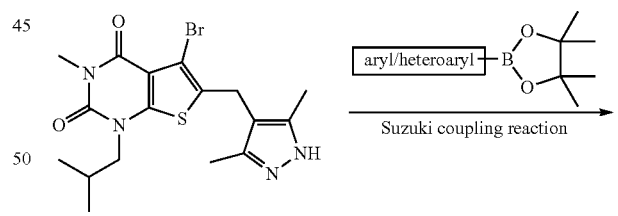<br><br>wherein Y =<br>$NH(CH_2)_5NH_2$-Gln<br>ring = phenyl<br>Z = $CH_2$ |

General Synthesis Scheme for Examples 1-14

Step 1

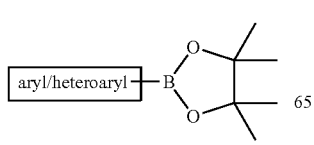

-continued

Step 2

Suzuki coupling reaction

Example 1. 6-((3,5-dimethyl-1H-pyrazol-4-yl)methyl)-5-(2-fluoro-3-(hydroxymethyl)phenyl)-1-isobutyl-3-methylthieno[2,3-d]pyrimidine-2,4(1H,3H)-dione Step 1.

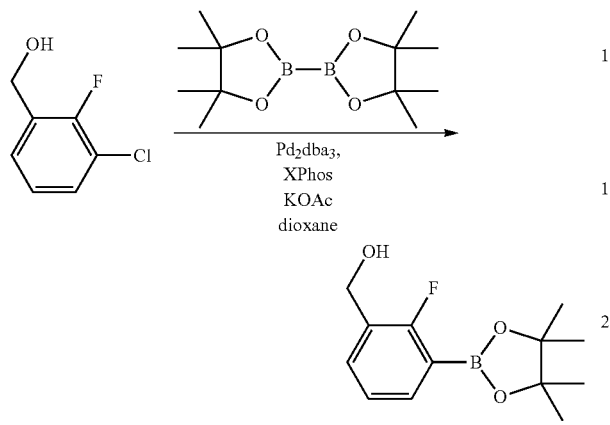

General procedure for the preparation of pinacolbornane reagents: An oven-dried vial filled with argon was charged with Pd$_2$dba$_3$ (2 mol %), X-Phos (4 mol %), bis(pinacolato)diboron (3 equiv.) and KOAc (3 equiv.). 1,4-Dioxane was added, followed by the addition of the aryl chloride or bromide (0.5 M in 1,4-dioxane). The vial was sealed, and the reaction mixture was heated to 110° C. until aryl halide had been completely consumed, as determined by TLC analysis. At this point the reaction mixture was allowed to cool to room temperature. The reaction solution was then filtered through a thin pad of Celite (eluting with ethyl acetate) and the eluent was concentrated under reduced pressure. The crude material so obtained was purified via flash chromatography on silica gel or utilized for Step 2m the Suzuki coupling reaction, directly and without purification.

Step 2.

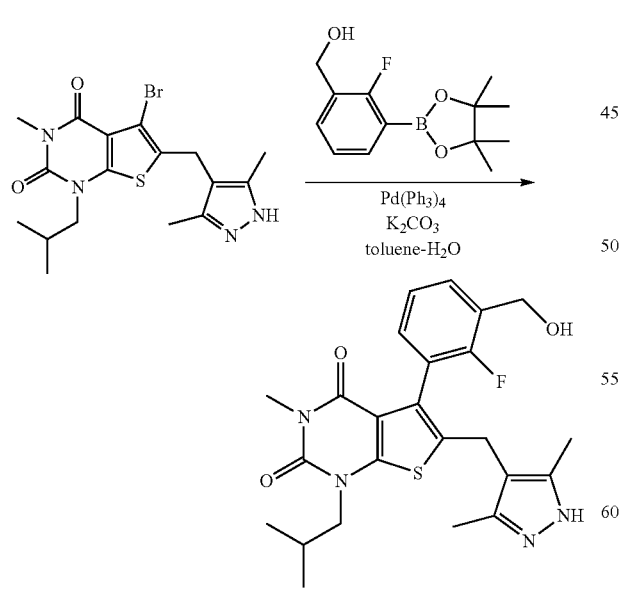

General procedure for the Suzuki reaction: An oven-dried vial filled with argon was charged with a mixture of the bromothiophene starting material (0.05 M in toluene, synthesis is described below), the borane reagent from step 1 (2 equiv.), Pd(PPh$_3$)$_4$ (0.2 equiv.), K$_2$CO$_3$ (3 equiv.), in minimal toluene-H$_2$O (3:1, V/V). The vial was sealed and the reaction mixture was heated to 110° C. overnight. After cooling, water was added and the reaction mixture was extracted three times with ethyl acetate. The combined organic layer was dried over anhydrous Na$_2$SO$_4$, and evaporated under reduced pressure. The crude product was purified by flash chromatography on silica gel to yield the product.

Data for the product of example 1: white solid, yield 36% from the Suzuki reaction, $^1$H NMR (400 MHz, CD$_3$OD) δ 7.53 (m, 1H), 7.24 (m, 2H), 4.72 (s, 2H), 3.76 (m, 2H), 3.69 (s, 2H), 3.26 (s, 3H), 2.27 (m, 1H), 2.06 (s, 6H), 0.96 (d, J=6.56 Hz, 6H). $^{13}$C NMR (101 MHz, CD$_3$OD and CDCl$_3$) δ 160.3, 159.6, 157.8, 153.5, 152.1, 135.8, 131.8, 130.2, 129.8, 129.6, 129.2, 124.6, 123.4, 123.3, 58.8, 56.8, 28.4, 28.1, 22.2, 20.2, 10.5.

Preparation of the bromide starting material 5-bromo-6-((3,5-dimethyl-1H-pyrazol-4-yl)methyl)-1-isobutyl-3-methylthieno[2,3-d]pyrimidine-2,4(1H,3H)-dione:

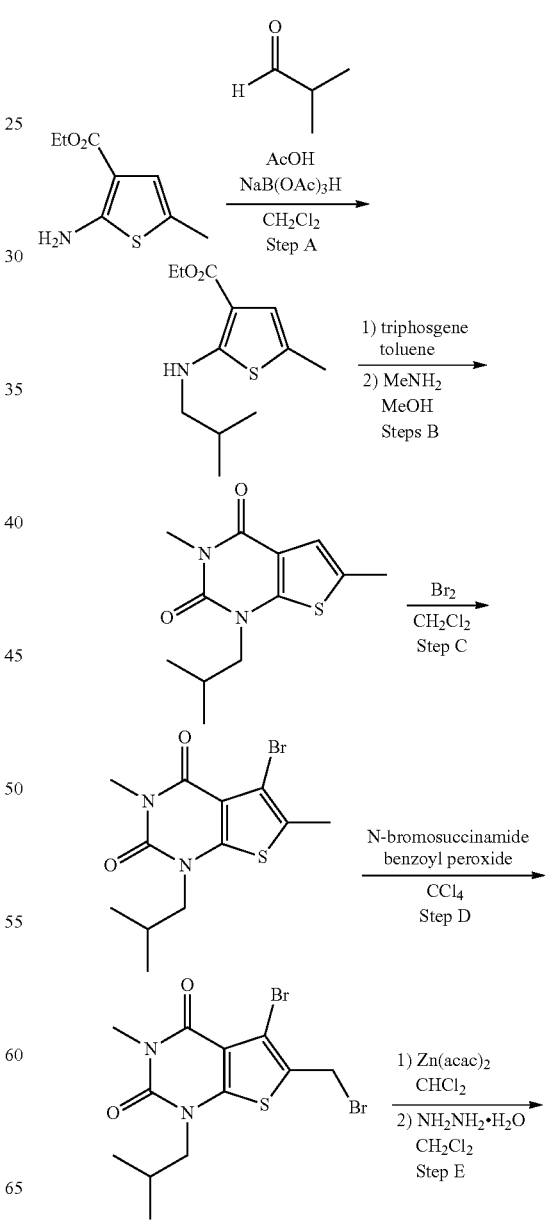

-continued

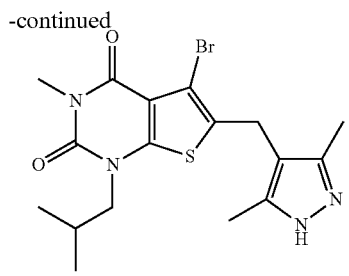

Step A. A flame dried 50-mL round bottom flask purged with argon was charged with ethyl 2-amino-5-methylthiophene-3-carboxylate (5 g, 27 mmol) and sodium triacetoxyborohydride (8.5 g, 41 mmol), $CH_2Cl_2$ (80 mL) was added followed by AcOH (1.5 mL, 27 mmol) and the reaction was cooled to 0° C. in an ice/water bath. Isobutyraldehyde (3 mL, 27 mmol) was added drop-wise then the mixture was allowed to warm to room temperature and stir for ~16 hours. Reaction was quenched with $H_2O$ and extracted with $CH_2Cl_2$. Organic layer was dried over $MgSO_4$, filtered and concentrated under reduced pressure. The crude material was purified via flash chromatography on silica gel to give the title compound as an off white solid (8.3 g, 78%). $^1H$ NMR (400 MHz, Chloroform-d) δ 7.42 (s, 1 H), 6.67-6.62 (m, 1H), 4.23 (q, J=7.1 Hz, 2H), 3.01 (t, J=6.4 Hz, 2H), 2.27 (s, J=1.3 Hz, 3H), 1.96 (dp, J=13.4, 6.7 Hz, 1H), 1.32 (t, J=7.1 Hz, 3H), 0.98 (d, J=6.7 Hz, 6H).

Step B. A flame dried 100-mL 3-neck round bottom flask purged with argon and fitted with a reflux condenser was charged with product from step A (650 mg, 2.7 mmol), triphosgene (269 mg, 0.89 mmol) and toluene (14 mL). Mixture was stirred in a 100° C. oil bath for 3 hours. The mixture was then cooled to room temperature and solvent was removed under reduced pressure. 2M methylamine in MeOH (17 mL) was added to the yellow residue and mixture was stirred for 16 hours at room temperature. Mixture was concentrated under reduced pressure and purified via flash chromatography on silica gel to give the title compound as a white solid (372 mg, 55%). $^1H$ NMR (400 MHz, Chloroform-d) δ 6.98 (q, J=1.3 Hz, 1H), 3.74 (d, J=7.6 Hz, 2H), 3.41 (s, 3H), 2.44 (d, J=1.3 Hz, 3H), 2.39-2.24 (m, 1H), 0.98 (d, J=6.7 Hz, 6H).

Step C. A flame dried 25-mL round bottom flask purged with argon was charged with product from step B (372 mg, 1.47 mmol). $CH_2Cl_2$ is added and the mixture was cooled to 0° C. in an ice/water bath. $Br_2$ (0.122 mL 2.36 mmol) was added drop-wise and mixture was allowed to stir at 0° C. for 1 hour then warmed to room temperature and stirred for an additional 4 hours. $Br_2$ (0.076 mL 1.47 mmol) was added dropwise and mixture was stirred for 5 hours at room temperature. Reaction was quenched by the addition of saturated $Na_2S_2O_3$ aqueous solution, extracted 3 times $CH_2Cl_2$. Combined organic layers were dried over $MgSO_4$, filtered and concentrated under reduced pressure to yield an orange solid. Crude material was purified via flash chromatography on silica gel to yield the title compound as a white solid (346 mg, 70%) $^1H$ NMR (400 MHz, Chloroform-d) δ 3.75 (d, J=7.6 Hz, 3H), 3.41 (s, 4H), 2.38 (s, 4H), 2.34-2.26 (m, 1H), 0.98 (d, J=6.7 Hz, 9H).

Step D. A flame dried 200-mL round bottom flask purged with argon and fitted with a reflux condenser was charged with product from step C (4.3 g, 13 mmol). $CCl_4$ (45 mL) was added followed by N-bromosuccinimide (2.31 g, 13 mmol) and benzoyl peroxide (126 mg, 0.52 mmol). Mixture was stirred in a 90° C. oil bath for 45 minutes then cooled to room temperature. 1M NaOH aqueous solution was added and the layers were partitioned. The organic layer was dried over $MgSO_4$, filtered and concentrated to yield a white solid as the title compound (5 g, 94%). $^1H$ NMR (400 MHz, Chloroform-d) δ 4.68 (s, 2H), 3.79 (d, J=7.7 Hz, 2H), 3.41 (s, 3H), 2.41-2.23 (m, 1H), 1.00 (d, J=6.7 Hz, 6H).

Step E. A flame dried 500-mL round bottom flask purged with argon and fitted with a reflux condenser was charged with the product from step D (5 g, 12.2 mmol) and $CHCl_3$ (120 mL). $Zn(acac)_2$ (3.22 g, 12.2 mmol) was added in one portion and the mixture was heated in a 76° C. oil bath for 15 minutes then cooled to room temperature. Saturated $NaHCO_3$ aqueous solution was added and extracted 2 times with $CH_2Cl_2$. Hydrazine monohydrate (1.19 mL, 24.6 mmol) is added to the combined organic layers and this mixture was stirred for 16 hours at room temperature. $MgSO_4$ was then added and the mixture was filtered and concentrated under reduced pressure. Crude material was purified via flash chromatography on silica gel followed by recrystallization in 5:1 hexanes:$CH_2Cl_2$. Title compound is isolated as a white solid (1.93 g, 37%). $^1H$ NMR (400 MHz, Chloroform-d) δ 3.84 (s, 2H), 3.67 (d, J=7.7 Hz, 2H), 3.40 (s, 3H), 2.27-2.16 (m, 1H), 2.22 (s, 6H), 0.92 (d, J=6.7 Hz, 6H). $^{13}C$ NMR (101 MHz, Chloroform-d) δ 157.58, 152.05, 150.60, 131.65, 112.36, 112.02, 104.59, 104.26, 55.55, 28.39, 27.01, 22.91, 20.05, 12.53, 11.11.

Example 2. 6-((3,5-dimethyl-1H-pyrazol-4-yl)methyl)-5-(2-fluoro-3-(hydroxymethyl)-5-methylphenyl)-1-isobutyl-3-methylthieno[2,3-d]pyrimidine-2,4(1H,3H)-dione Step 1 followed the general procedure from Example 1 step 1, and used (3-bromo-2-fluoro-5-methylphenyl)methanol as the halide reagent to give the pinacol borane (2-fluoro-5-methyl-3-(4,4,5,5-tetramethyl-1,3,2-dioxaborolan-2-yl)phenyl)methanol in 58% yield. $^1H$ NMR (400 MHz, $CDCl_3$) δ 7.44 (d, J=4.96 Hz, 1H), 7.30 (dd, $J_1$=7.08 Hz, $J_2$=1.96 Hz, 1H), 4.69 (s, 2H), 2.30 (s, 3H), 1.35 (s, 12H).

Step 2 followed the general procedure from Example 1 step 2. Purification by flash chromatography gave the title compound as a white solid in 70% yield. $^1H$ NMR (400 MHz, $CD_3OD$) δ 7.31 (dd, $J_1$=6.42 Hz, $J_2$=1.60 Hz, 1H), 7.01 (dd, $J_1$=6.36 Hz, $J_2$=1.84 Hz, 1H), 4.67 (s, 2H), 3.75 (m, 2H), 3.67 (s, 2H), 3.26 (s, 3H), 2.36 (s, 3H), 2.26 (m, 1H), 2.06 (s, 6H), 0.96 (d, J=6.68 Hz, 6H). $^{13}C$ NMR (101 MHz, $CD_3OD$) δ 159.4, 158.2, 155.8, 153.2, 151.9, 143.4, 135.4, 133.9, 131.9, 130.6, 130.5, 129.2, 129.0, 128.8, 122.8, 122.6, 114.7, 113.7, 58.8, 58.7, 56.7, 28.4, 27.9, 22.1, 20.8, 20.3, 10.6.

Example 3. 6-((3,5-dimethyl-1H-pyrazol-4-yl)methyl)-1-isobutyl-3-methyl-5-(2,4,6-trifluoro-3-(hydroxymethyl)phenyl)thieno[2,3-d]pyrimidine-2,4(1H,3H)-dione Step 1 followed the general procedure from Example 1 step 1, though the starting bromide was first prepared from bromination and reduction of 2,4,6-triflurobenzaldehyde:

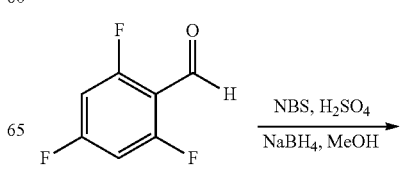

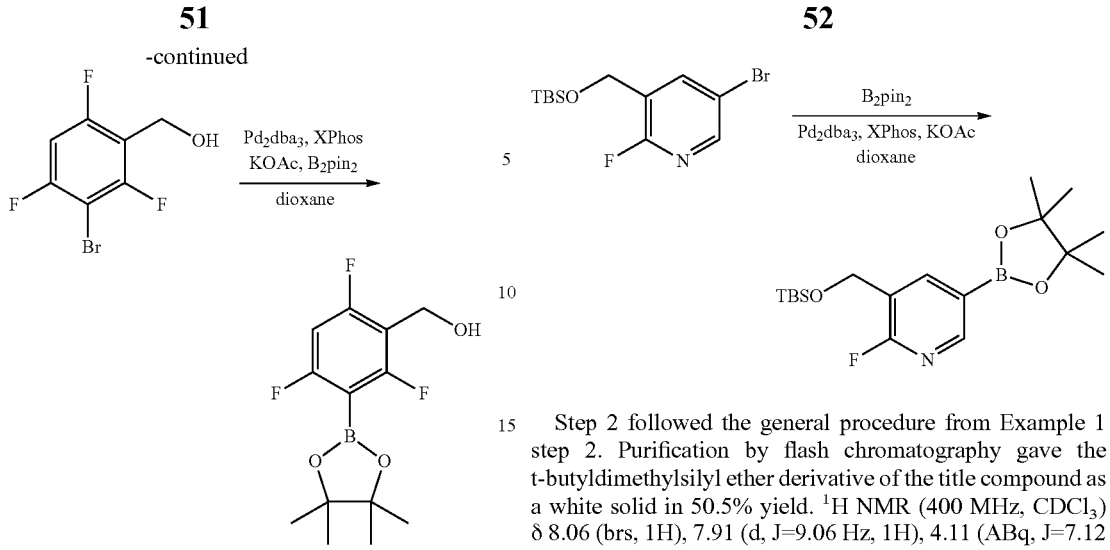

2,4,6-trifluorobenzaldehyde (100 mg, 0.625 mmol) was dissolved in concentrated H₂SO₄ (0.3 mL) and heated to 60° C. To this was added N-bromosuccinimide (134 mg, 0.75 mmol) in three portions over a period of 10 min. After being heated for 3 h under argon, the reaction mixture was poured into ice water. The product was extracted with hexanes, washed with water and brine, and then dried over anhydrous Na2SO4. The organic layer was concentrated under reduced pressure to give 2,4,6-trifluoro-3-bromobenzaldehyde (149 mg, 100% yield). ¹H NMR (400 MHz, CDCl₃) δ 10.25 (s, 1H), 6.89 (dt, J₁=9.12 Hz, J₂=2.04 Hz, 1H), This product was dissolved in 2 mL of methanol and to this stirring solution was added NaBH₄ (29 mg, 0.75 mmol). The reaction was stirred for 1 h at room temperature. Then the reaction was diluted with ethyl acetate, washed with saturated aqueous NH₄Cl, followed by brine. The organic layer was dried over anhydrous Na₂SO₄, and evaporated under reduced pressure yielded 2,4,6-trifluoro-3-1.5 bromobenzyl alcohol as a white solid (136 mg, 90% yield). This material was used for Suzuki coupling reaction without purification. ¹H NMR (400 MHz, CDCl₃) δ 7.78 (dt, J1=9.08 Hz, J2=2.20 Hz, 1H), 4.76 (s, 2H). ¹³C NMR (101 MHz, CDCl₃) δ 161.8, 161.7, 161.6, 160.8, 160.7, 160.6, 160.5, 160.1, 160.0, 159.9, 159.4, 159.3, 159.2, 159.1, 158.3, 158.2, 158.1, 157.6, 157.5, 157.4, 113.9, 113.8, 113.7, 113.6, 113.5, 113.4, 101.3, 101.2, 101.0, 100.7, 93.9, 93.8, 93.6, 93.4, 93.3, 52.6, Step 2 followed the general procedure from Example 1 step 2. Purification by flash chromatography gave the title compound as a white solid in 27.7% yield. ¹H NMR (400 MHz, CD₃OD) δ 7.56 (m, 1H), 4.73 (s, 2H), 3.60 (d, J=7.64 Hz, 2H), 3.26 (s, 2H), 3.01 (s, 3H), 2.22 (m, 1H), 2.01 (s, 6H), 0.87 (d, J=6.68 Hz, 6H).

Example 4. 6-((3,5-dimethyl-1H-pyrazol-4-yl)methyl)-5-(6-fluoro-5-(hydroxymethyl)pyridin-3-yl)-1-isobutyl-3-methylthieno[2,3-d]pyrimidine-2,4(1H,3H)-dione Step 1 followed the general procedure from Example 1 step 1, though in this case the hydroxyl group was protected as the t-butyldimethylsilyl ether. The boronate product was used in Step 2, the Suzuki reaction, without purification or NMR analysis.

Step 2 followed the general procedure from Example 1 step 2. Purification by flash chromatography gave the t-butyldimethylsilyl ether derivative of the title compound as a white solid in 50.5% yield. ¹H NMR (400 MHz, CDCl₃) δ 8.06 (brs, 1H), 7.91 (d, J=9.06 Hz, 1H), 4.11 (ABq, J=7.12 Hz, 2H), 3.73 (d, J=7.64 Hz, 2H), 3.68 (s, 2H), 3.31 (s, 3H), 2.25 (m, 1H), 2.11 (s, 6H), 0.96 (d, J=6.68 Hz, 6H), 0.92 (s, 9H), 0.12 (s, 6H). To a solution of this silyl ether (12 mg, 0.020 mmol) in 0.5 mL of dry THF was added dropwise via syringe tetra-butylammonium fluoride (0.06 ml), The mixture was allowed to stir at room temperature for 1.5 h before addition of saturated Na₂CO₃ (1 mL). The aqueous layer was extracted with ethyl acetate (2 mL×3). The organic layers were combined, dried over Na₂SO₄, filtered and concentrated under reduced pressure. The residue was purified by flash chromatography to give a white solid (2 mg, 21% yield). ¹H NMR (400 MHz, CDCl₃) δ 8.05 (brs, 1H), 7.83 (d, J=9.08 Hz, 1H), 4.77 (s, 2H), 3.75 (d, J=7.68 Hz, 2H), 3.70 (s, 2H), 3.31 (s, 3H), 2.28 (m, 1H), 2.07 (s, 6H), 0.98 (d, J=6.68 Hz, 6H). ¹³C NMR (101 MHz, CDCl₃) δ 161.1, 159.8, 158.5, 152.5, 150.8, 146.2, 146.0, 143.0, 140.8, 133.9, 130.4, 128.9, 122.4, 122.3, 113.5, 110.0, 58.5, 56.1, 29.8, 28.3, 27.1, 20.1, 11.0.

Example 5. 5-(3,4-difluoro-5-(hydroxymethyl)phenyl)-6-((3,5-dimethyl-1H-pyrazol-4-yl)methyl)-1-isobutyl-3-methylthieno[2,3-d]pyrimidine-2,4(1H,3H)-dione Step 1 followed the general procedure from Example 3 step 1. 2,3-difluorobenzaldehyde (200 mg, 1.408 mmol) was dissolved in concentrated H₂SO₄ (0.64 mL) and heated to 60° C. To this was added N-bromosuccinimide (301 mg, 1.690 mmol) in three portions over a period of 20 min, After being heated for 3 h under argon, the reaction mixture was poured into ice water. The product was extracted with hexanes, washed with water and brine, and then dried over anhydrous Na₂SO₄. Purification by flash chromatography yielded an orange liquid as 2,3-difluoro-5-bromobenzaldehyde (155 mg, 50% yield), which was dissolved in 6 mL of methanol. To this stirring solution was added NaBH₄ (32 mg, 0.84 mmol). The reaction was stirred for 1 h at room temperature. Then the reaction was diluted with ethyl acetate, washed with saturated aqueous NH₄Cl, followed by brine. The organic layer was dried over anhydrous Na₂SO₄, and evaporated under reduced pressure yielded 2,3-difluoro-5-bromobenzyl alcohol as a white solid (163 mg, 87% yield). The boronate product was then obtained from 2,3-difluoro-5-bromobenzyl alcohol according to the general procedure of Example 1. The crude material was used for Suzuki coupling reaction without purification.

Step 2 followed the general procedure from Example 1 step 2. Purification by flash chromatography gave the title compound as a white solid in 27.7% yield. ¹H NMR (400 MHz, CD₃OD) δ 7.56 (m, 1H), 4.73 (s, 2H), 3.60 (d, J=7.64 Hz, 2H), 3.26 (s, 2H), 3.01 (s, 3H), 2.22 (m, 1H), 2.01 (s, 6H), 0.87 (d, J=6.68 Hz, 6H).

Example 6. 5-(2,4-difluoro-5-(hydroxymethyl)phenyl)-6-((3,5-dimethyl-1H-pyrazol-4-yl)methyl)-1-isobutyl-3-methylthieno[2,3-d]pyrimidine-2,4(1H,3H)-dione Step 1 followed the general procedure from Example 1 step 1 using 5-chloro-2,4-difluorobenzyl alcohol. Purification by flash chromatography gave the boronate as a white solid in 52% yield. ¹H NMR (400 MHz, CDCl₃) δ 7.78 (dd, J₁=9.04 Hz, J2=6.84 Hz, 1H), 6.87 (t, J=9.44 Hz, 1H), 4.67 (s, 2H), 1.33 (s, 12H). ¹³C NMR (101 MHz, CDCl₃) δ 168.7, 168.6, 166.2, 166.0, 164.6, 164.5, 162.1, 162.0, 138.0, 137.9, 137.8, 123.8, 123.7, 123.6, 104.0, 103.7, 103.4, 84.1, 58.9, 24.9.

Step 2 followed the general procedure from Example 1 step 2. Purification by flash chromatography gave the title compound as a white solid in 46.2% yield. ¹H NMR (400 MHz, CDCl₃) δ 7.31 (t, J=8.08 Hz, 1H), 6.90 (t, J=9.48 Hz, 1H), 4.73 (ABq, J=13.32 Hz, 2H), 3.73 (m, 2H), 3.64 (s, 2H), 3.31 (s, 3H), 2.27 (m, 1H), 2.08 (s, 6H), 0.97 (d, J=6.68 Hz, 6H), ¹³C NMR (101 MHz, CDCl₃) δ 160.7, 159.1, 158.4, 152.1, 150.9, 143.0, 134.1, 132.1, 131.8, 128.7, 127.4, 124.1, 119.0, 113.7, 113.2, 58.7, 56.0, 28.2, 27.1, 21.7, 20.1, 10.8.

Example 7. 5-(2,4-difluoro-3-(hydroxymethyl)phenyl)-6-((3,5-dimethyl-1H-pyrazol-4-yl)methyl)-1-isobutyl-3-methylthieno[2,3-d]pyrimidine-2,4(1H,3H)-dione Step 1 followed the general procedure from Example 1 step 1 using 3-chloro-2,6-difluorobenzyl alcohol according to the general procedure. Purification by flash chromatography gave the title compound as a white solid in 57% yield. ¹H NMR (400 MHz, CDCl₃) δ 7.67 (q, J=7.16 Hz, 1H), 6.87 (1, J=8.60 Hz, 1H), 4.76 (s, 2H), 1.34 (s, 12H). ¹³C NMR (101 MHz, CDCl₃) δ 167.5, 167.4, 165.2, 165.1, 165.0, 164.9, 162.7, 162.6, 137.4, 137.3, 137.2, 116.2, 116.1, 116.0, 115.8, 111.5, 111.3, 111.2, 84.1, 52.9, 24.8.

Step 2 followed the general procedure from Example 1 step 2. Purification by flash chromatography gave the title compound as a white solid in 43% yield. ¹H NMR (400 MHz, CD₃OD) δ 7.32 (q, J=8.08 Hz, 1H), 7.05 (t, J=8.76 Hz, 1H), 4.72 (s, 2H), 3.76 (d, J=7.20 Hz, 2H), 3.71 (d, J=3.36 Hz, 2H), 3.26 (s, 3H), 2.07 (s, 6H), 2.26 (m, 1H), 0.95 (d, J=6.68 Hz, 6H). ¹³H NMR (101 MHz, CD₃OD) δ 164.2, 164.1, 161.7, 161.6, 159.7, 159.1, 159.0, 153.6, 152.2, 143.8, 136.3, 133.1, 133.0, 128.4, 120.0, 119.8, 117.7, 114.6, 113.9, 111.9, 111.7, 56.8, 52.6, 28.4, 28.2, 22.2, 20.2, 10.5.

Example 8. 6-((3,5-dimethyl-1H-pyrazol-4-yl)methyl)-1-isobutyl-3-methyl-5-(5-(2,2,2-trifluoro-1-hydroxyethyl)pyridin-3-yl)thieno[2,3-cl]pyrimidine-2,4(1H,3H)-dione Step 1 followed the general procedure from Example 4 step 1, with a hydroxyl croup protected as the t-butyldimethylsilyl ether. The crude material was then used for the Suzuki coupling reaction without purification.

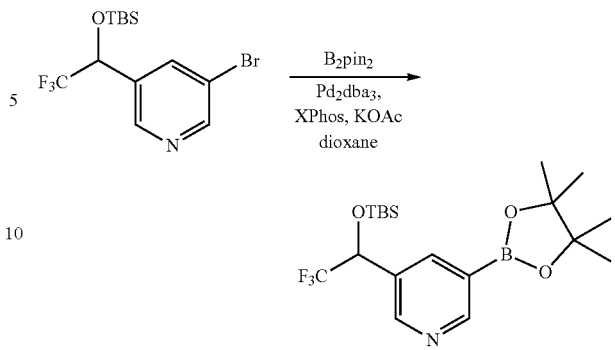

Step 2 followed the general procedure from Example 1 step 2. Purification by flash chromatography gave the t-butyldimethylsilyl ether derivative of the title compound as a white solid in 40% yield. ¹H NMR (400 MHz, CDCl₃) δ 8.66 (s, 1H), 8.62 (d. J=1.72 Hz, 1H), 7.83 (s, 1H), 5.06 (q, J=6.28 Hz, 1H), 3.73 (d, J=7.68 Hz, 2H), 3.68 (s, 2H), 3.31 (s, 3H), 2.27 (m, 1H), 2.16 (s, 6H), 0.96 (d, J=6.60 Hz, 6H), 0.90 (s, 9H), 0.16 (s, 3H), 0.05 (s, 3H). ¹³C NMR (101 MHz, CD₃OD) δ 158.0, 152.5, 151.1, 150.9, 147.9, 142.7, 137.0, 134.4, 130.8, 130.5, 130.4, 125.5, 113.3, 113.2, 56.0, 53.5, 31.0, 28.2, 27.1, 25.6, 20.1, 18.2, 10.9, −4.8, −5.2. To a solution of this material (18 mg, 0.028 mmol) in 0.5 mL of dry THF was added dropwise via syringe tetra-butylammonium fluoride (0.06 ml). The mixture was allowed to stir at room temperature for 1.5 h before addition of saturated Na₂CO₃ (1 mL). The aqueous layer was extracted with ethyl acetate (2 mL×3). The organic layers were combined, dried over Na₂SO₄, filtered and concentrated under reduced pressure. The residue was purified by flash chromatography to give the title compound as a white solid (6 mg, 40% yield). ¹H NMR (400 MHz, CDCl₃) δ 8.66 (brs, 1H), 8.56 (d, J=1.88 Hz, 1H), 7.98 (brs, 1H), 5.27 (m, 1H), 3.79 (d, J=7.64 Hz, 2H), 3.76 (d, J=7.64 Hz, 2H), 3.76 (s, 2H), 3.27 (s, 3H), 2.27 (m, 1H), 2.05 (s, 6H), 0.96 (d, J=6.68 Hz, 6H). ¹³C NMR (101 MHz, CD₃OD) δ 159.8, 154.1, 152.2, 151.5, 148.2, 138.7, 136.4, 132.9, 132.4, 131.4, 130.2, 124.5, 114.2, 114.0, 75.8, 56.9, 28.4, 28.2, 25.0, 22.0, 10.5.

Example 9. 6-((3,5-dimethyl-1H-pyrazol-4-yl)methyl)-5-(4-fluoro-3-(hydroxymethyl)phenyl)-1-isobutyl-3-methylthieno[2,3-d]pyrimidine-2,4(1H,3H)-dione Step 1 followed the general procedure from Example 1 step 1 using 3-chloro-2-fluorobenzyl alcohol according to the general procedure. The crude material was used for Suzuki coupling reaction without purification.

Step 2 followed the general procedure from Example 1 step 2. Purification by flash chromatography gave the title compound as a white solid in 48% yield. LC-MS (ESI): m/z 471.2 [M+1]⁺.

Example 10. 6-((3,5-dimethyl-1H-pyrazol-4-yl)methyl)-5-(2-(hydroxymethyl)pyridin-4-yl)-1-isobutyl-3-methyithieno[2,3-d]pyrimidine-2,4(1H,3H)-dione Step 1 followed the general procedure from Example 4 step 1 the corresponding des-fluoro starting material according to the general procedure. The crude material was used for Suzuki coupling reaction without purification.

Step 2 followed the general procedure from Example 9 step 2. ¹H NMR (400 MHz, Chloroform-d) δ 8.63 (d, J=5.0 Hz, 1H), 7.29-7.24 (m, 3H), 7.19 (dd, J=5.1, 1.6 Hz, 1H), 4.82 (s, 2H), 3.74 (d, J=7.7 Hz, 2H), 3.66 (s, 2H), 3.48 (s, 2H), 3.32 (s, 3H), 2.28 (dt, J=13.8, 6.9 Hz, 1H), 2.09 (s, 6H), 0.97 (d, J=6.7 Hz, 6H); LC-MS (ESI): m/z 454 [M+1]⁺.

Example 11. 6-((3,5-dimethyl-1H-pyrazol-4-yl)methyl)-5-(3-fluoro-5-(hydroxymethyl)phenyl)-1-isobutyl-3-methyithieno[2,3-d]pyrimidine-2,4(1H,3H)-dione Step 1 followed the general procedure from Example 9 step 1 using 3-chloro-5-fluorobenzyl alcohol as the starting material according to the general procedure. The crude material was used for Suzuki coupling reaction without purification.
Step 2 followed the general procedure from Example 9 step 2. LC-MS (ESI): m/z 471 [M−1]⁺.

Example 12. 6-((3,5-dimethyl-1H-pyrazol-4-yl)methyl)-5-(5-(hydroxymethyl)pyridin-3-yl)-1-isobutyl-3-methylthieno[2,3-d]pyrimidine-2,4(1H,3H)-dione Step 1 followed the general procedure from Example 1 step 1 using (5-bromopyridin-3-yl)methanol as the starting material according to the general procedure. The crude material was used for Suzuki coupling reaction without purification.
Step 2 followed the general procedure from Example 9 step 2. LC-MS (ESI): m/z 454 [M+1]⁺.

Example 13. 6-((3,5-dimethyl-1H-pyrazol-4-yl)methyl)-5-(3-(1-hydroxyethyl)phenyl)-1-isobutyl-3-methylthieno[2,3-d]pyrimidine-2,4(1H,3H)-dione Step 1 followed the general procedure from Example 1 step 1. 3-bromoacetophenone was first reduced to the alcohol using NaBH₄. This bromide was the starting material for boronate formation according to the general procedure. The crude material was then used for the Suzuki coupling reaction without purification.
Step 2 followed the general procedure from Example 9 step 2. LC-MS (ESI): m/z 467 [M+1]⁺.

Example 14. 6-((3,5-dimethyl-1H-pyrazol-4-yl)methyl)-1-isobutyl-3-methyl-5-(3-(2,2,2-trifluoro-1-hydroxyethyl)phenyl)thieno[2,3-d]pyrimidine-2,4(1H,3H)-dione Step 1 followed the general procedure from Example 1 step 1. 1-(3-bromophenyl)-2,2,2-trifluoroethanol was the starting material for boronate formation according to the general procedure. The crude material was then used for the Suzuki coupling reaction without purification.
Step 2 followed the general procedure from Example 9 step 2. LC-MS (ESI): m/z 521 [M+1]⁺.

Example 15. 6-((3,5-dimethyl-1H-pyrazol-4-yl)methyl)-5-(3-(hydroxymethyl)phenyl)-1-isobutyl-3-methylthieno[2,3-d]pyrimidine-2,4(1H,3H)-dione Step 1 followed the general procedure from Example 1 step 1 using (3-bromophenyl)methanol as the starting material according to the general procedure. The crude material was used for Suzuki coupling reaction without purification.
Step 2 followed the general procedure from Example 1 step 2. LC-MS (ESI): m/z 453.2 [M+1]⁺.

General Synthesis Scheme for Examples 16-24

Step 1 use commercially available boronic acid, pinacol boronic ester, or make as follows:

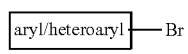
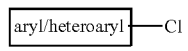
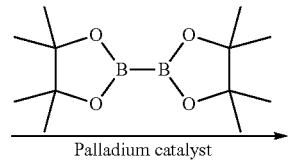

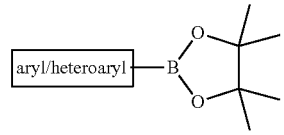

Step 2

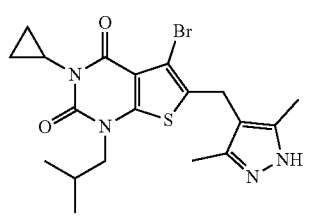

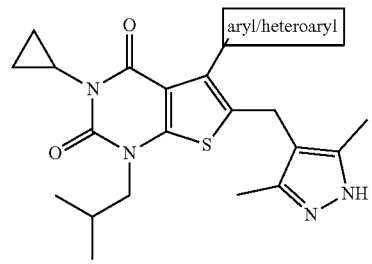

Example 16. 3-cyclopropyl-6-((3,5-dimethyl-1H-pyrazol-4-yl)methyl)-5-(4-fluoro-3-(hydroxymethyl)phenyl)-1-isobutylthieno[2,3-d]pyrimidine-2,4(1H,3H)-dione Step 1: (4-fluoro-3-formylphenyl)boronic acid was commercially available and was used in Step 2.
Step 2 followed the general Suzuki reaction procedure, but using the formylated boronic ester as shown, and followed by reduction:

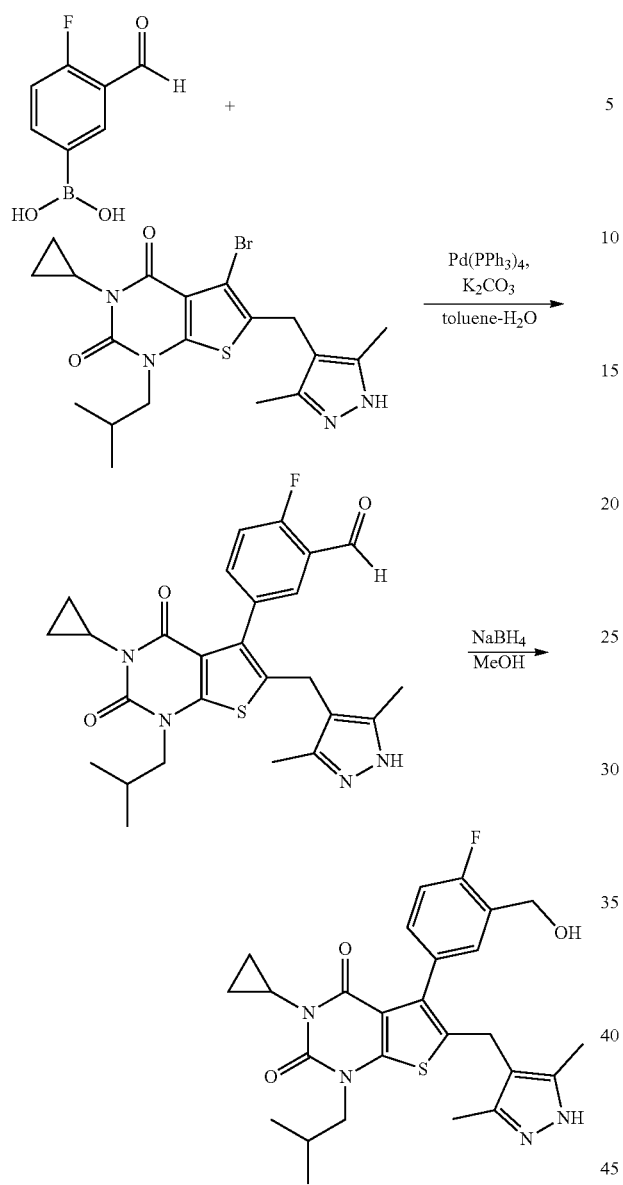

4-fluoro-3-formylphenylboronic acid and the indicated bromothiophene (synthesis shown below) were used in the general procedure for Suzuki coupling, as in Example 1 Step 2. A mixture of the crude product from the Suzuki coupling and NaBH$_4$ (2 equiv.) was stirred in MeOH for 1 h at room temperature. The reaction mixture was diluted with ethyl acetate, washed with saturated aqueous NH$_4$Cl and brine. The organic layer was dried over anhydrous Na$_2$SO$_4$, and evaporated under reduced pressure. The crude product was purified by flash chromatography to yield the title compound as a white solid in 65.7% yield for two steps. $^1$H NMR (400 MHz, CDCl$_3$) δ 7.38 (dd, J$_1$=7.07 Hz, J$_2$=1.64 Hz, 1H), 7.19 (m, 1H), 7.05 (t, J=8.84 Hz, 1H), 4.75 (s, 2H), 370 (d, J=7.60 Hz, 2H), 3.59 (s, 2H), 2.60 (m, 1H), 2.24 (m, 1H), 2.03 (s, 6H), 1.06 Om 2H), 0.95 (d, J=6.68 Hz, 6H), 0.72 (m, 2H). $^{13}$C NMR (101 MHz, CDCl$_3$) δ 161.2, 159.5, 158.7, 152.5, 151.6, 142.6, 134.2, 132.7, 130.7, 130.5, 130.4, 130.3, 128.2, 128.1, 115.0, 114.7, 113.8, 113.2, 58.8, 55.1, 27.1, 25.3, 20.1, 10.9, 9.0.

Preparation of the bromide starting material 5-bromo-6-((3,5-dimethyl-1H-pyrazol-4-yl)methyl)-1-isobutyl-3-methylthieno[2,3-d]pyrimidine-2,4(1H,3H)-dione:

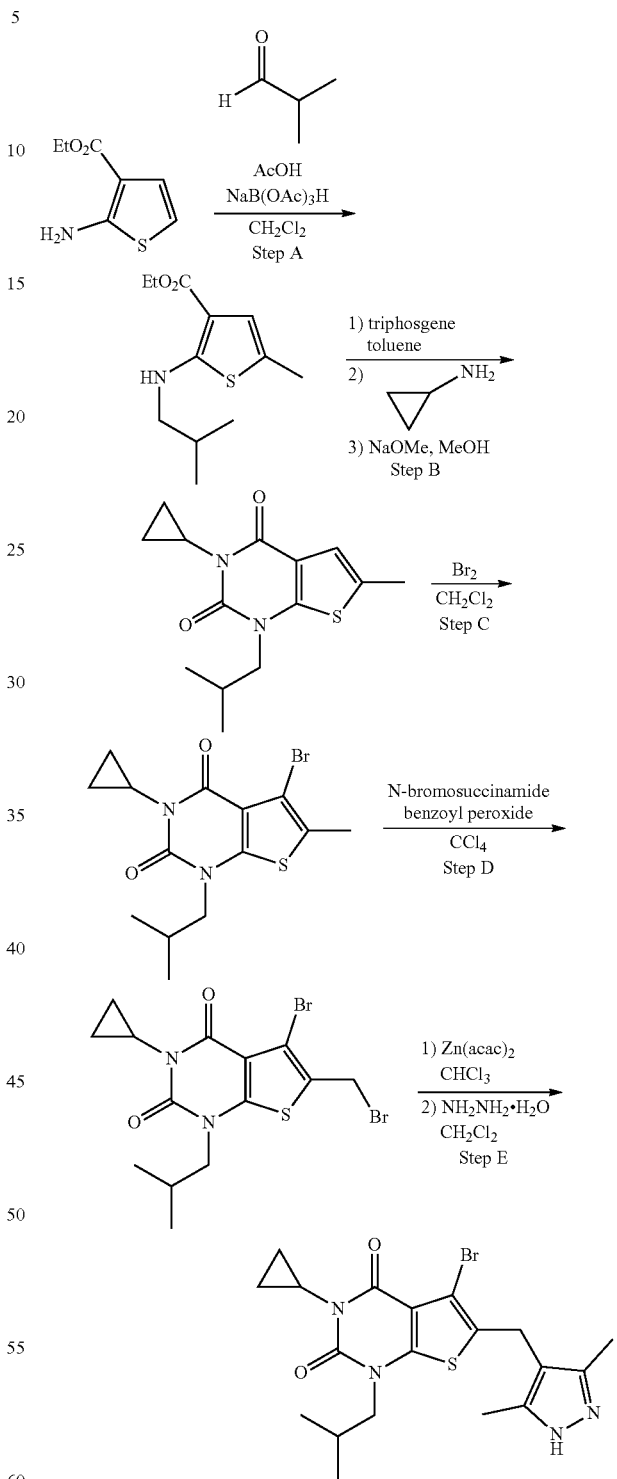

Preparation of this bromide followed the procedure used in Example 1 for the N-Me analog, using cyclopropylamine in place of methylamine in Step B and adding a base treatment step at the end of Step B to promote cyclization. The Step B procedure: A flame dried flask purged with argon and fitted with a reflux condenser was charged with product from step A of Example 1 (100 mg, 0.41 mmol) and toluene (1.6 mL). Triphosgene (62 mg, 0.20 mmol) is added and the mixture was stirred while heating in a 100° C. oil bath for 2.5 hours. Cyclopropyl amine (63 µL, 0.91 mmol) was then added and mixture was stirred at 100° C. for an additional 2.5 hours. Mixture was cooled to room temperature and quenched with water, extracted with ethyl acetate and concentrated under reduced pressure. Crude material was purified via flash chromatography on silica gel to afford the urea compound (76 mg, 57%). $^1$H NMR (400 MHz, Chloroform-d) δ 8.12 (s, 1H), 6.30 (q, J=1.3 Hz, 1H), 5.57 (s, 1H), 2.97 (d, J=6.7 Hz, 2H), 2.27 (d, J=1.2 Hz, 3H), 1.94 (dp, J=13.4, 6.7 Hz, 1H), 0.98 (d, J=6.7 Hz, 6H), 0.85 0.73 (m, 2H), 0.58 0.49 (m, 2H). A flame dried round bottom flask purged with argon was charged with the product above (71 mg, 0.22 mmol), sodium methoxide (47 mg, 0.88 mmol) and methanol (0.8 mL), The mixture was stirred for 3 hours at room temperature then quenched with water, extracted with methoxy ethane, and the combined organics were concentrated under reduced pressure, The crude material was purified via flash chromatography on silica gel to yield the cyclized product (57 mg, 93%). $^1$H NMR (400 MHz, Chloroform-d) δ 6.94 (q, J=1.2 Hz, 1H), 3.71 (d, J=7.6 Hz, 2H), 2.73 (tt, J=7.1, 4.0 Hz, 1H), 2.42 (d, J=1.3 Hz, 3H), 2.37-2.21 (m, 1H), 1.24-1.10 (m, 2H), 0.97 (d, J=6.7 Hz, 6H), 0.85 0.75 (m, 2H).

Step C: A flame dried round bottom flask purged with argon was charged with product from step 2b (200 mg, 0.72 mmol) and $CH_2Cl_2$ (2 mL). Bromine (70 µL, 1.08 mmol) was added at room temperature and the mixture was stirred for 16 hours. Reaction was quenched by the addition of saturated $Na_2S_2O_3$ aqueous solution, extracted 3 times $CH_2Cl_2$. Combined organic layers were dried over $MgSO_4$, filtered and concentrated to yield an orange solid. Crude material was purified via flash chromatography on silica gel to yield the title compound as a white solid (220 mg, 86%). $^1$H NMR (400 MHz, Chloroformed) δ 3.72 (d, J=7.6 Hz, 2H), 2.72 (tt, J=7.1, 4.1 Hz, 1H), 2.36 (s, 3H), 2.27 (p, J=7.0 Hz, 1H), 1.28-1.09 (m, 2H), 0.97 (d, J=6.7 Hz, 6H), 0.89-0.76 (m, 2H).

Step D followed Step D in example 1 for the N-Me compound. Step E followed Step E in example 1 for the N-Me compound, giving the brominated product: $^1$H NMR (400 MHz, Chloroform-d) δ 3.83 (s, 2H), 3.31 (s, 7H), 2.72 (tt, J=7.1, 4.1 Hz, 1H), 2.23 (5, 6H), 2.24-2.11 (m, 1H), 1.27-1.13 (m, 2H), 0.92 (d, J=6.7 Hz, 6H), 0.85 0.72 (m, 2H).

Example 17. 3-cyclopropyl-6-((3,5-dimethyl-1H-pyrazol-4-yl)methyl)-5-(2-fluoro-3-(hydroxymethyl)-5-methylphenyl)-1-isobutylthieno[2,3-d]pyrimidine-2,4(1H,3H)-dione Step 1 was previously shown as Example 2, Step 1.
Step 2 followed the general procedure from Example 1 step 2 using the N-cyclopropyl-containing bromide. Purification by flash chromatography gave the title compound as a white solid in 21.4% yield. $^1$H NMR (400 MHz, $CD_3OD$) δ 7.32 (dd, J, =6.40 Hz, $J_2$=1.60 Hz, 1H), 7.03 ($J_1$=6.40 Hz, $J_2$=1.80 Hz, 1H), 4.87 (d, J=2.24 Hz, 2H), 3.75 (m, 2H), 3.68 (brs, 2H), 2.57 (m, 1H), 2.37 (s, 3H), 2.23 (m, 1H), 2.04 (s, 6H), 1.03 (m, 2H), 0.95 (dd, $J_1$=6.68 Hz, $J_2$=1.60 Hz, 6H), 0.68 (m, 2H). $^{13}$C NMR (101 MHz, $CD_3OD$) δ 160.7, 158.5, 156.1, 153.7, 153.1, 143.5, 135.5, 134.2, 132.2, 130.7, 129.5, 129.3, 129.2, 123.2, 123.0, 115.2, 114.1, 58.9, 56.7, 28.3, 26.1, 22.2, 20.8, 20.2, 10.5, 9.6, 9.5.

Example 18. 3-cyclopropyl-5-(3,4-difluoro-5-(hydroxymethyl)phenyl)-6-((3,5-dimethyl-1H-pyrazol-4-yl)methyl)-1-isobutylthieno[2,3-d]pyrimidine-2,4(1H,3H)-dione Step 1 was previously shown as Example 5, Step 1.
Step 2 followed the general procedure from Example 1 step 2 using the N-cyclopropyl-containing bromide. Purification by flash chromatography gave the title compound as a white solid in 35% yield. $^1$H NMR (400 MHz, $CDCl_3$) δ 7.18 (d, J=5.12 Hz, 1H), 7.02 (m, 1H), 4.75 (s, 2H), 3.70 (d, J=7.64 Hz, 2H), 3.59 (s, 2H), 2.60 (m, 1H), 2.24 (m, 1H), 2.04 (s, 6H), 1.06 (m, 1H), 0.94 (d, J=6.68 Hz, 6H), 0.71 (m, 1H). $^{13}$C NMR (101 MHz, $CD_3OD$ and $CDCl_3$) δ 160.2, 153.3, 152.4, 151.6, 149.6, 149.1, 147.1, 143.3, 134.8, 133.5, 131.6, 131.5, 131.1, 131.0, 125.9, 118.4, 118.2, 114.3, 113.4, 58.2, 56.4, 27.7, 25.7, 22.0, 20.3, 10.7, 9.3, Example 19. 3-cyclopropyl-5-(2,4-difluoro-5-(hydroxymethyl)phenyl)-6-((3,5-dimethyl-1H-pyrazol-4-yl)methyl)-1-isobutylthieno[2,3-d]pyrimidine-2,4(1H,3H)-dione Step 1 was previously shown as Example 6, Step 1.
Step 2 followed the general procedure from Example 1 step 2 using the N-cyclopropyl-containing bromide. Purification by flash chromatography gave the title compound as a white solid in 19% yield. $^1$H NMR (400 MHz, $CDCl_3$) δ 7.31 (t, J=8.16 Hz, 1H), 6.88 (t, J=9.48 Hz, 1H), 4.72 (ABq, J=13.28 Hz, 2H), 3.71 (m, 2H), 3.62 (s, 2H), 2.62 (m, 1H), 2.24 (m, 1H), 2.07 (s, 6H), 1.08 (m, 1H), 0.96 (d, J=6.68 Hz, 6H), 0.72 (m, 2H). $^{13}$C NMR (101 MHz, $CDCl_3$) δ 159.3, 159.1, 158.4, 152.3, 151.7, 142.9, 133.9, 131.7, 127.4, 124.0, 118.5, 114.0, 113.2, 103.9, 103.7, 58.6, 55.8, 27.1, 25.3, 21.7, 20.2, 10.8, 8.0.

Example 20. 3-cyclopropyl-6-((3,5-dimethyl-1H-pyrazol-4-yl)methyl)-5-(2-fluoro-3-(hydroxymethyl)phenyl)-1-isobutylthieno[2,3-d]pyrimidine-2,4(1H, 3H)-dione Step 1 was previously shown as Example 1, Step 1.
Step 2 followed the general procedure from Example 1 step 2 using the N-cyclopropyl-containing bromide. Purification by flash chromatography gave the title compound as a white solid in 33% yield: $^1$H NMR (400 MHz, $CD_3OD$) δ 7.52 (m, 1H), 7.23 (m, 2H), 4.72 (s, 2H), 3.73 (m, 2H), 3.66 (s, 2H), 2.57 (m, 1H), 2.24 (m, 1H), 2.05 (5, 6H), 1.05 (m, 2H), 0.95 (d, J=6.68 Hz, 6H), 0.69 (m, 2H). $^{13}$C NMR (101 MHz, $CD_3OD$ and $CDCl_3$) δ 160.5, 160.1, 157.6, 153.4, 152.9, 135.6, 131.7, 130.0, 129.6, 129.4, 129.1, 124.4, 123.2, 123.1, 115.0, 113.7, 58.8, 58.7, 56.6, 28.0, 25.9, 22.1, 20.3, 10.6, 9.5, 9.4.

Example 21. 3-cyclopropyl-5-(2,4-difluoro-3-(hydroxymethyl)phenyl)-6-((3,5-dimethyl-1H-pyrazol-4-yl)methyl)-1-isobutylthieno[2,3-d]pyrimidine-2,4(1H,3H)-dione Step 1 was previously shown as Example 7, Step 1.
Step 2 followed the general procedure from Example 1 step 2 using the N-cyclopropyl-containing bromide, Purification by flash chromatography gave the title compound as a white solid in 29% yield: LC-MS (ESI): m/z 515.3 [M+1]⁺.

Example 22, 3-cyclopropyl-6-((3,5-dimethyl-1H-pyrazol-4-yl)methyl)-5-(2-fluoro-5-(hydroxymethyl)phenyl)-1-isobutylthieno[2,3-d]pyrimidine-2,4(1H,3H)-dione Step 1 followed the general procedure from Example 1 step 1, and used (3-bromo-4-fluorophenyl)methanol as the halide reagent.
Step 2 followed the general procedure from Example 1 step 2 using the N-cyclopropyl-containing bromide. Purification by flash chromatography gave the title compound as a white solid in 31% yield: LC-MS (ESI): m/z 497.2 [M+1]⁺.

Example 23. 3-cyclopropyl-6-((3,5-dimethyl-1H-pyrazol-4-yl)methyl)-5-(2-(hydroxymethyl)pyridin-4-yl)-1-isobutylthieno[2,3-d]pyrimidine-2,4(1H,3H)-dione Step 1 was previously shown as Example 10, Step 1.
Step 2 followed the general procedure from Example 1 step 2 using the N-cyclopropyl-containing bromide. Purification by flash chromatography gave the title compound as a white solid in 37% yield: ¹H NMR (400 MHz, Chloroform-d) δ 8.61 (dd, J=5.1, 0.8 Hz, 1H), 7.25 (dd, J=1.7, 0.9 Hz, 1H), 7.17 (dd, J=5.1, 1.6 Hz, 1H), 5.29 (s, 1H), 4.81 (s, 2H), 3.71 (d, J=7.6 Hz, 2H), 3.63 (5, 2H), 3.48 (s, 2H), 2.63 (tt, J=7.1, 4.0 Hz, 1H), 2.32 2.17 (m, 1H), 2.08 (s, 6H), 1.15-1.05 (m, 2H), 0.96 (d, J=6.7 Hz, 6H), 0.78 0.68 (m, 2H).

Example 24. 3-cyclopropyl-6-((3,5-dimethyl-1H-pyrazol-4-yl)methyl)-5-(3-(hydroxymethyl)phenyl)-1-isobutylthieno[2,3-d]pyrimidine-2,4(1H,3H)-dione Step 1 was previously shown as Example 15, Step 1.
Step 2 followed the general procedure from Example 1 step 2 using the N-cyclopropyl-containing bromide. Purification by flash chromatography gave the title compound as a white solid in 24% yield: LC-MS (ESI): m/z 479.1 [M+1]⁺.

General Synthesis Scheme for Examples 25-40

Step 1 use commercially available boronic acid, pinacol boronic ester, or make as follows:

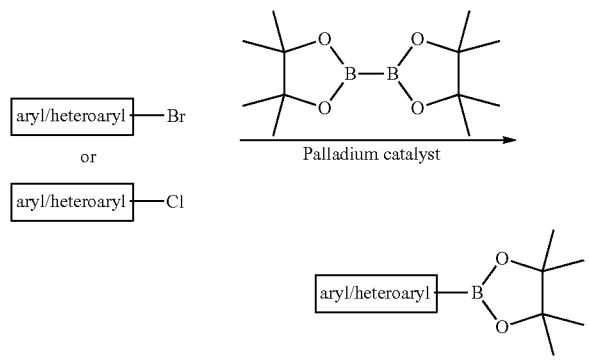

Step 2

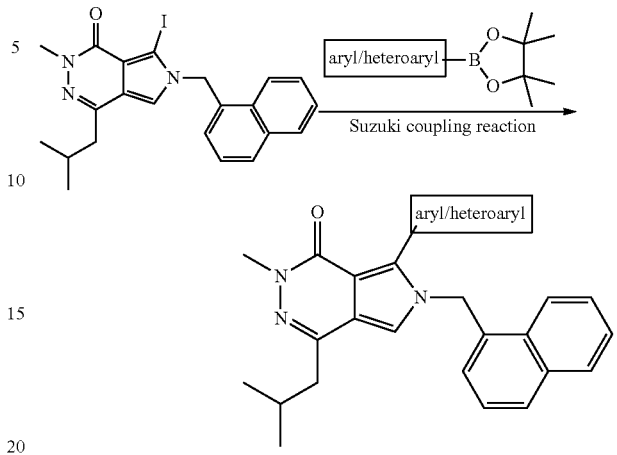

Example 25, 7-(5-(hydroxymethyl)thiazol-2-yl)-4-isobutyl-2-methyl-6-(naphthalen-1-ylmethyl)-2,6-dihydro-1H-pyrrolo[3,4-d]pyridazin-1-one Step 1 followed the general procedure of Example 1 Step 1 using (2-bromothiazol-5-yl)methanol. The boronate was taken to the next step without purification.

Preparation of the Iodine-Containing Starting Material for Step 2

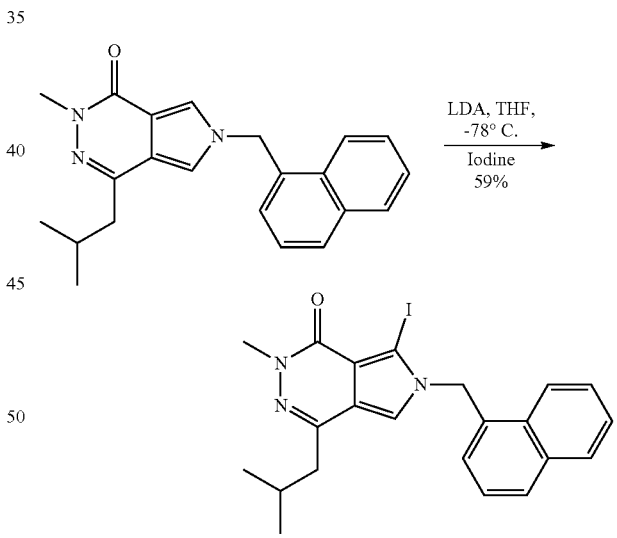

LDA (0.5 M, 0.6 mL, 0.3 mmol), was added to a solution of the previous product (100 mg, 0.29 mmol) in THF at −78° C. The reaction mixture was stirred for 30 min. at the same temperature followed by addition of a solution of iodine (74 mg, 0.29 mmol) solution in THF. The reaction mixture was allowed to stir for additional 20 min at −78° C. then warmed up to room temperature. After 2 h, the reaction was quenched by sat. aq. NH₄Cl solution and diluted with ethyl acetate. The aqueous phase was extracted with ethyl acetate (10 mL×2) and the combined organic layers were washed with brine, dried over. Na₂SO₄, filtered and concentrated.

The crude product was purified by flash chromatography to afford 7-iodo-4-isobutyl-2-methyl-6-(naphthalen-1-ylmethyl)-2,6-dihydro-1H-pyrrolo[3,4-d]pyridazin-1-one (81 mg, 59%) as a off white solid. LCMS 472.2 (M+H)⁺.

Step 2 followed the general procedure from Example 1 step 2. Purification by flash chromatography gave the title compound as a white solid in 43% yield: ¹H NMR (CDCl₃, 400 MHz) 7.94-7.88 (m, 3H), 7.68 (s, 1H), 7.57-7.52 (m, 2H), 7.42-7.39 (m, 1H), 7.02 (s, 1H), 6.98-6.96 (m, 1H), 6.35 (s, 1H), 4.90 (s, 2H), 3.77 (s, 3H), 2.48 (d, 2H, J=7.2), 2.08-1.98 (m, 1H), 0.90 (d, 6H, J=6.4). LCMS 459.2 (M+H)⁺.

Example 26. 7-(2-(hydroxymethyl)thiazol-4-yl)-4-isobutyl-2-methyl-6-(naphthalen-1-ylmethyl)-2,6-dihydro-1H-pyrrolo[3,4-d]pyridazin-1-one Step 1 followed the general procedure of Example 1 Step 1 using (4-bromothiazol-2-yl)methanol. The boronate was taken to the next step without purification.

Step 2 followed the general procedure from Example 1 step 2 using the iodide from Example 25, Purification by flash chromatography gave the title compound as a white solid in 41% yield: LCMS 459.2 (M+H)⁺.

Example 27. 7-(2,4-difluoro-3-(hydroxymethyl)phenyl)-4-isobutyl-2-methyl-6-(naphthalen-1-ylmethyl)-2,6-dihydro-1H-pyrrolo[3,4-d]pyridazin-1-one Step 1: see Example 7.
Step 2 followed the general procedure from Example 1 step 2. Purification by flash chromatography gave the title compound as a white solid in 36% yield: LCMS 488.2 (M+H)⁺.

Example 28. 7-(2-fluoro-5-(hydroxymethyl)phenyl)-4-isobutyl-2-methyl-6-(naphthalen-1-ylmethyl)-2,6-dihydro-1H-pyrrolo[3,4-d]pyridazin-1-one Step 1: see Example 22.
Step 2 followed the general procedure from Example 1 step 2 using the iodide from Example 25. Purification by flash chromatography gave the title compound as a white solid in 46% yield: LCMS 470.2 (M+H)⁺.

Example 29. 7-(2-fluoro-3-(hydroxymethyl)phenyl)-4-isobutyl-2-methyl-6-(naphthalen-1-ylmethyl)-2,6-dihydro-1H-pyrrolo[3,4-d]pyridazin-1-one Step 1: see Example 1.
Step 2 followed the general procedure from Example 1 step 2 using the iodide from Example 25. Purification by flash chromatography gave the title compound as a white solid in 33% yield: LCMS 470.2 (M+H)⁺.

Example 30. 7-(2-chloro-5-(hydroxymethyl)phenyl)-4-isobutyl-2-methyl-6-(naphthalen-1-ylmethyl)-2,6-dihydro-1H-pyrrolo[3,4-d]pyridazin-1-one Step 1: Commercial (2-chloro-5-(methoxycarbonyl)phenyl)boronic acid was obtained and used in the Suzuki reaction.

Step 2 followed the general procedure from Example 1 step 2 using the iodide from Example 25 to give the methyl ester analog of the desired product, methyl 4-chloro-3-(4-isobutyl-2-methyl-6-(naphthalen-1-ylmethyl)-1-oxo-2,6-dihydro-1H-pyrrolo[3,4-d]pyridazin-7-yl)benzoate. This material was dissolved in minimal dry THF at 0° C. and 2.5 equiv. of LiAlH₄ was added. Standard water/base/water work-up and filtration gave the crude product. Purification by flash chromatography gave the title compound as a white solid in 17% yield for the three steps: LCMS 486.2 (M+H)⁺.

Example 31. 7-(3-(hydroxymethyl)phenyl)-4-isobutyl-2-methyl-6-(naphthalen-1-ylmethyl)-2,6-dihydro-1H-pyrrolo[3,4-d]pyridazin-1-one Step 1: Commercial (3-(hydroxymethyl)phenyl)boronic acid was used.
Step 2 followed the general procedure from Example 1 step 2 using the iodide from Example 25. Purification by flash chromatography gave the title compound as a white solid in 29% yield: LCMS 452.2 (M+H)⁺.

Example 32. 7-(5-(hydroxymethyl)pyridin-3-yl)-4-isobutyl-2-methyl-6-(naphthalen-1-ylmethyl)-2,6-dihydro-1H-pyrrolo[3,4-d]pyridazin-1-one Step 1 followed the general procedure of Example 1 Step 1 using (5-bromopyridin-3-yl)methanol. The boronate was taken to the next step without purification.
Step 2 followed the general procedure from Example 1 step 2 using the iodide from Example 25. Purification by flash chromatography gave the title compound as a white solid in 40% yield: LCMS 453.2 (M+H)⁺.

Example 33. 7-(5-(1-hydroxyethyl)thiophen-3-yl)-4-isobutyl-2-methyl-6-(naphthalen-1-ylmethyl)-2,6-dihydro-1H-pyrrolo[3,4-d]pyridazin-1-one Step 1: Commercial 1-(4-bromothiophen-2-yl)ethanone was obtained and used in the Suzuki reaction.
Step 2 followed the general procedure from Example 30 step 2. Purification by flash chromatography gave the title compound as a white solid in 14% yield: ¹H NMR (CDCl₃, 400 MHz) 7.86-7.85 (m, 1H), 7.79-7.77 (m, 1H), 7.67-7.64 (m, 1H), 7.45-7.42 (m, 2H), 7.38-7.30 (m, 1H), 7.16-7.15 (m, 1H), 7.10-7.09 (m, 1H), 6.93 (s, 1H), 6.80-6.78 (m, 1H), 5.67 (s, 2H), 5.02-4.97 (m, 1H), 3.63 (s, 3H), 2.44 (d, 2H, J=7.6), 2.05-2.02 (m, 1H), 1.44 (d, 3H, J=6.4), 0.85 (d, 6H, J=6.8). LCMS 472.1 (M+H)⁺.

Example 34. 7-(6-(1-hydroxyethyl)pyridin-2-yl)-4-isobutyl-2-methyl-6-(naphthalen-1-ylmethyl)-2,6-dihydro-1H-pyrrolo[3,4-d]pyridazin-1-one Step 1: Commercial 1-(6-bromopyridin-2-yl)ethanone was obtained and used in the Suzuki reaction.
Step 2 followed the general procedure from Example 30 step 2. Purification by flash chromatography gave the title compound as a white solid in 11% yield: ¹H NMR (CDCl₃, 400 MHz) 7.85-7.72 (m, 5H), 7.46-7.42 (m, 2H), 7.37-7.33 (m, 1H), 7.30-7.28 (m, 1H), 7.07 (s, 1H), 6.86-6.84 (m, 1H), 6.86 (s, 2H), 4.85-4.78 (m, 2H), 3.68 (s, 3H), 2.47 (d, 2H, J=7.6), 2.06-1.95 (m, 1H), 1.31 (d, 3H, J=6.4), 0.85 (d, 6H, J=6.8). LCMS 467.3 (M+H)⁺.

Example 35. 7-(2-fluoro-5-(1-hydroxyethyl)phenyl)-4-isobutyl-2-methyl-6-(naphthalen-1-ylmethyl)-2,6-dihydro-1H-pyrrolo[3,4-d]pyridazin-1-one Step 1: Commercial 1-(3-bromo-4-fluorophenyl)ethanone was obtained and used in the Suzuki reaction.

Step 2 followed the general procedure from Example 30 step 2. Purification by flash chromatography gave the title compound as a white solid in 16% yield: $^1$H NMR (CDCl$_3$, 400 MHz) 7.90-7.85 (m, 2H), 7.64-7.62 (m, 1H), 7.54-7.41 (m, 5H), 7.20-7.07 (m, 2H), 6.99-6.98 (m, 1H), 5.67-5.60 (m, 2H), 4.88-4.83 (m, 1H), 3.69 (s, 3H), 2.50 (d, 2H, J=7.6), 2.10-2.06 (m, 1H), 1.40 (d, 3H, J=6.4) 0.95-0.91 (m, 6H). LCMS 484.1 (M+H)$^+$.

Example 36. 7-(3-(1-hydroxyethyl)phenyl)-4-isobutyl-2-methyl-6-(naphthalen-1-ylmethyl)-2,6-dihydro-1H-pyrrolo[3,4-d]pyridazin-1-one Step 1: Commercial 1-(3-(4,4,5,5-tetramethyl-1,3,2-dioxaborolan-2-yl)phenyl)ethanone was obtained and used in the Suzuki reaction.

Step 2 followed the general procedure from Example 30 step 2. Purification by flash chromatography gave the title compound as a white solid in 34% yield: LCMS 466.3 (M+H)$^+$.

Example 37. 4-isobutyl-2-methyl-6-(naphthalen-1-ylmethyl)-7-(2-(2,2,2-trifluoro-1-hydroxyethyl)thiazol-4-yl)-2,6-dihydro-1H-pyrrolo[3,4-d]pyridazin-1-one Step 1:

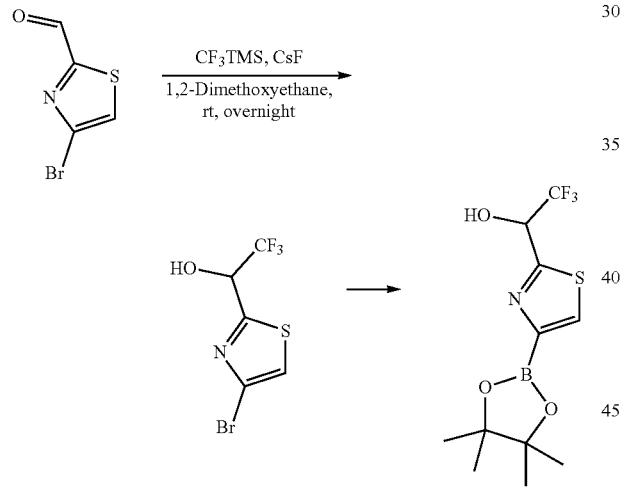

To a stirred solution of commercial 4-bromothiazole-2-carbaldehyde (1 eq), CF$_3$TMS (1.1 eq) in dimethoxyethane was added CsF (10 mol %) under argon atmosphere. The reaction mixture was allowed to stir for overnight. The solvent was removed under vacuum, water was added, and the solution was extracted with ethyl acetate. The combined organic layers were washed with brine, dried over sodium sulphate, concentrated under vacuum, and purified by flash chromatography using 10-20% of ethyl acetate in hexanes, and isolated in 67% yield. This material was then converted to the boronic ester to be used in the Suzuki reaction, following the procedure of Example 1, step 2.

Step 2: The Suzuki reaction followed the general procedure from Example 1 step 2 using the iodide from Example 25 to give the title product, which was purified by flash chromatography and isolated in 45% yield as a white solid: $^1$H NMR (CDCl$_3$, 400 MHz) 8.54 (s, 1H), 7.83-7.73 (m, 3H), 7.47-7.7.42 (m, 2H), 7.30-7.26 (m, 1H), 6.93 (s, 1H), 6.79-6.78 (m, 1H), 6.03 (s, 2H), 4.99-4.95 (m, 1H), 3.66 (s, 3H), 2.43 (d, 2H, J=7.6), 2.04-1.94 (m, 1H), 0.85-0.83 (m, 6H). LCMS 527.1 (M+H)$^+$.

Example 38. 4-isobutyl-2-methyl-6-(naphthalen-1-ylmethyl)-7-(5-(2,2,2-trifluoro-1-hydroxyethyl)thiophen-3-yl)-2,6-dihydro-1H-pyrrolo[3,4-d]pyridazin-1-one Step 1 followed the general procedure of Example 37 Step 1 using 4-bromothiophene-2-carbaldehyde as the starting reagent and followed by conversion to the boronate which was taken to the next step without purification.

Step 2: The Suzuki reaction followed the general procedure from Example 1 step 2 using the iodide from Example 25 to give the title product, which was purified by flash chromatography and isolated in 33% yield as a white solid: LCMS 526.3 (M+H)$^+$.

Example 39. 4-isobutyl-2-methyl-6-(naphthalen-1-ylmethyl)-7-(5-(2,2,2-trifluoro-1-hydroxyethyl)thiophen-2-yl)-2,6-dihydro-1H-pyrrolo[3,4-d]pyridazin-1-one Step 1 followed the general procedure of Example 37 Step 1 using 5-bromothiophene-2-carbaldehyde as the starting reagent and followed by conversion to the boronate which was taken to the next step without purification.

Step 2: The Suzuki reaction followed the general procedure from Example 1 step 2 using the iodide from Example 25 to give the title product, which was purified by flash chromatography and isolated in 36% yield as a white solid: $^1$H NMR (CDCl$_3$, 400 MHz) 7.95-7.94 (m, 1H0, 7.93-7.88 (m, 1H), 7.75-7.72 (m, 1H0, 7.58-7.52 (m, 2H), 7.47-7.43 (m, 1H), 7.12-7.07 (m, 2H0, 7.03 (s, 1H0, 6.97-6.95 (m, 1H), 5.76 (s, 2H), 5.17-5.12 (m, 2H), 3.73 (s, 3H), 2.52 (d, 2H, J=7.6), 2.14-2.02 (m, 1H), 0.94 (d, 6H, J=6.8). LCMS 526.3 (M+H)$^+$.

Example 40. 4-isobutyl-2-methyl-6-(naphthalen-1-ylmethyl)-7-(3-(2,2,2-trifluoro-1-hydroxyethyl)phenyl)-2,6-dihydro-1H-pyrrolo[3,4-d]pyridazin-1-one Step 1 followed the general procedure of Example 37 Step 1 using 3-bromobenzaldehyde as the starting reagent and followed by conversion to the boronate which was taken to the next step without purification.

Step 2: The Suzuki reaction followed the general procedure from Example 1 step 2 using the iodide from Example 25 to give the title product, which was purified by flash chromatography and isolated in 32% yield as a white solid: LCMS 520.3 (M+H)$^+$.

General Synthesis Scheme for Examples 41-42

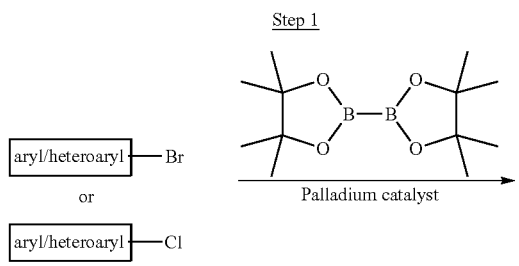

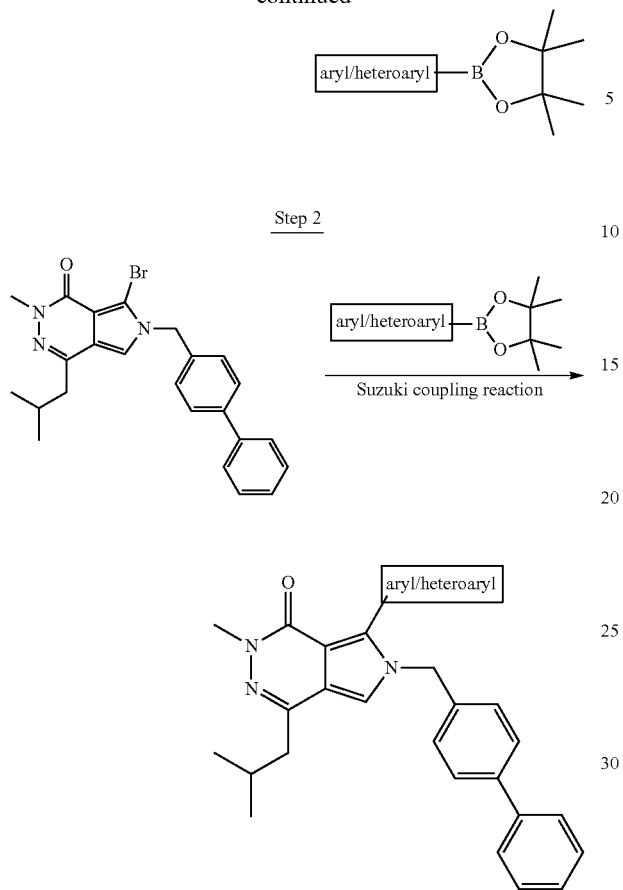

Example 41. 6-([1,1'-biphenyl]-4-ylmethyl)-7-(2-fluoro-5-(hydroxymethyl)phenyl)-4-isobutyl-2-methyl-2,6-dihydro-1H-pyrrolo[3,4-d]pyridazin-1-one Step 1: see Example 23.
Preparation of the iodo starting material for Step 2:

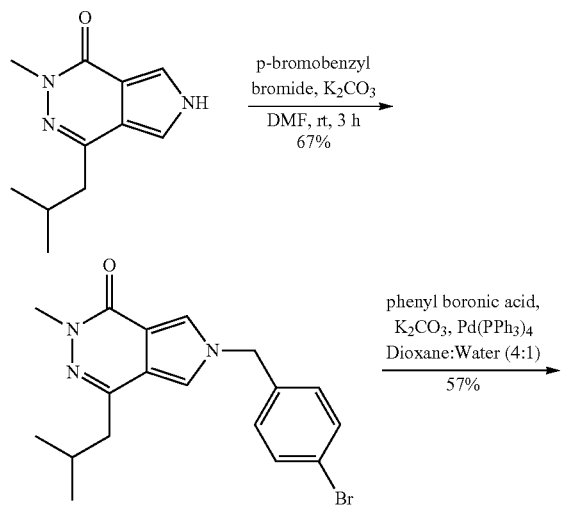

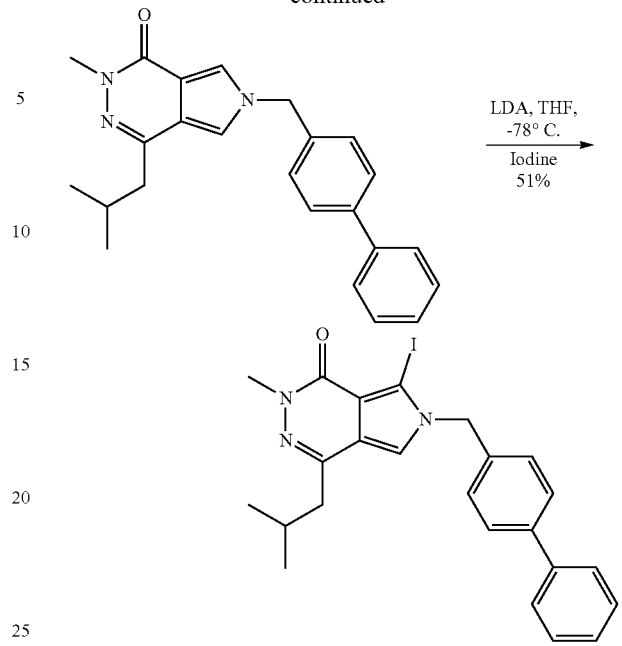

To a solution of 4-isobutyl-2-methyl-2,6-dihydro-1H-pyrrolo[3,4-d]pyridazin-1-one (50 mg, 0.243 mmol) in DMF (10 mL) was added $K_2CO_3$ (67 mg, 0.49 mmol) at room temperature under nitrogen. After 5 min p-bromobenzyl bromide (1.2 eq) was added, The reaction mixture was stirred for an additional 2 h. The solid was filtered off, DMF was removed under vacuum, the residue was dissolved in ethyl acetate and was washed with water (20 mL) and brine (20 mL×2). The combined organic layers were dried over anhydrous sodium sulfate, filtered and concentrated. Purification by flash chromatography (20% EtOAc/Hexanes) afforded the intermediate bromide 6-(4-bromobenzyl)-4-isobutyl-2-methyl-2,6-dihydro-11-1H-pyrrolo[3,4-d]pyridazin-1-one (67%) as a white solid. LCMS m/z 374 & 376, 1:1 (M+H)$^+$. Suzuki reaction with phenyl boronic as in Example 1 Step 2 gave 6-([1,1'-biphenyl]-4-ylmethyl)-4-isobutyl-2-methyl-2,6-dihydro-1H-pyrrolo[3,4-d]pyridazin-1-one in 69% yield after purification by flash chromatography: LCMS 372.2 (M+H)$^+$. LDA (0.5 M, 0.6 mL, 0.3 mmol), was added to a solution of the previous product (108 mg, 0.29 mmol) in THF at −78° C. The reaction mixture was stirred for 30 min. at the same temperature followed by addition of a solution of iodine (74 mg, 0.29 mmol) solution in THF. The reaction mixture was allowed to stir for additional 20 min at −78° C. then warmed up to room temperature. After 2 h, the reaction was quenched by sat. aq. $NH_4Cl$ solution and diluted with ethyl acetate. The aqueous phase was extracted with EtOAc (10 mL×2) and the combined organic layers were washed with brine, dried over $Na_2SO_4$, filtered and concentrated. The crude product was purified by flash chromatography to afford 6-([1,1'-biphenyl]-4-ylmethyl)-7-iodo-4-isobutyl-2-methyl-2,6-dihydro-1H-pyrrolo[3,4-d]pyridazin-1-one (80 mg, 55%) as a off white solid. LCMS 498.2 (M+H)$^+$.

Step 2: The Suzuki reaction followed the general procedure from Example 1 step 2 to give the title product, which was purified by flash chromatography and isolated in 36% yield as a white solid: LCMS 496.2 (M+H)$^+$.

Example 42, 6-([1,1'-biphenyl]-4-ylmethyl)-7-(3-(1-hydroxyethyl)phenyl)-4-isobutyl-2-methyl-2,6-dihydro-1H-pyrrolo[3,4-d]pyridazin-1-one Step 1: see Example 13.
Step 2: The Suzuki reaction followed the general procedure from Example 1 step 2 using the iodide as described in Example 41 to give the title product, which was purified by flash chromatography and isolated in 37% yield as a white solid: LCMS 492.2 (M+H)+.

General Synthesis Scheme for Examples 43-45

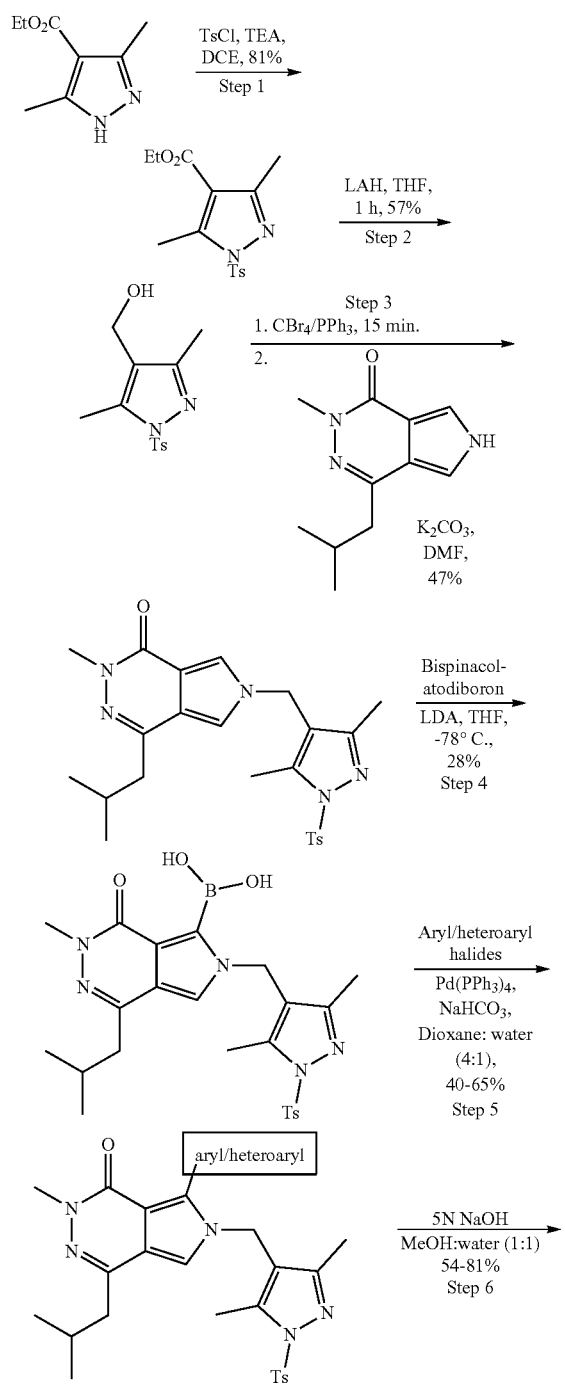

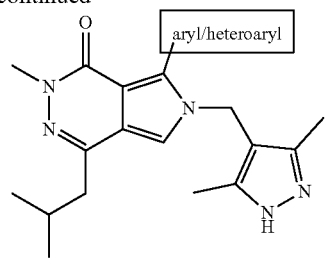

Example 43. 6-((3,5-dimethyl-1H-pyrazol-4-yl)methyl)-7-(3-(hydroxymethyl)phenyl)-4-isobutyl-2-methyl-2,6-dihydro-1H-pyrrolo[3,4-d]pyridazin-1-one Step 1: To a stirred solution of ethyl 3,5-dimethyl-1H-pyrazole-4-carboxylate (500 mg, 3.51 mmol) in dichlormethane (7 mL), was added triethylamine (0.98 mL, 7.02 mmol) and p-tosyl chloride (1.02 g, 5.35 mmol) at room temperature. The reaction was allowed to stir for 1 h and then water (10 mL) was added and the solution was extracted with dichlormethane (30 mL×2). The combined organic extracts were washed with brine dried over $Na_2SO_4$, concentrated under vacuum and the residue was purified by flash chromatography on silica gel using 12% of ethyl acetate in hexanes to afford the desired compound ethyl 3,5-dimethyl-1-tosyl-1H-pyrazole-4-carboxylate (620 mg, 55%). MS (ES) m/z: 323.1 (M+H)+. This compound was noted to be sensitive to decomposition upon storage and was used immediately in the next step.

Step 2: To a stirred solution of ethyl 3,5-dimethyl-1-tosyl-1H-pyrazole-4-carboxylate (500 mg, 1.55 mmol) in dry THF was added a solution of $LiAlH_4$ in THF (2.3 mL, 2.32 mmol) at 0° C. The reaction mixture was allowed to stir for 30 min and then quenched by dropwise addition of ethyl acetate followed by water. The reaction mixture was partitioned between ethyl acetate and water. The combined organic extracts were washed with water and brine and dried over $Na_2SO_4$. Removal of solvents under vacuum afforded the desired compound (3,5-dimethyl-1-tosyl-1H-pyrazol-4-yl)methanol (400 mg, 92%). $^1$H NMR ($CDCl_3$, 400 MHz) 7.88-7.85 (m, 2H), 7.34-7.32 (m, 2H), 4.45 (s, 2H), 2.53 (s, 3H), 2.44 (s, 3H), 2.29 (s, 3H).

Step 3: To a stirred solution of (3,5-dimethyl-1-tosyl-1H-pyrazol-4-yl)methanol (76 mg, 0.27 mmol), 4-isobutyl-2-methyl-2,6-dihydro-1H-pyrrolo[3,4-d]pyridazin-1-one (50 mg, 0.24 mmol), and triphenylphosphine (71 mg, 0.27 mmol) in 1,2 dichloroethane (4 mL) under argon was added carbon tetrabromide (89 mg, 0.27 mmol) at room temperature. The reaction was allowed to stir overnight. The reaction was quenched by the addition of water (10 mL). Extraction with ethyl acetate (20 mL×2), washing with water and brine, drying with $Na_2SO_4$, and concentration under vacuum gave a crude residue that was purified by flash chromatography on silica gel using 70% ethyl acetate in hexanes to afford the desired compound 6-((3,5-dimethyl-1-tosyl-1H-pyrazol-4-yl)methyl)-4-isobutyl-2-methyl-2,6-dihydro-1H-pyrrolo[3,4-d]pyridazin-1-one (75 mg, 66%). MS (ES) m/z: 468.1 (M+H)+.

Step 4: LDA (0.5 M, 0.3 mL, 0.15 mmol), was added to a solution of 6-((3,5-dimethyl-1-tosyl-1H-pyrazol-4-yl)methyl)-4-isobutyl-2-methyl-2,6-dihydro-1H-pyrrolo[3,4-d]pyridazin-1-one (68 mg, 0.145 mmol) in THF at −78° C. The reaction mixture was stirred for 30 min. at the same temperature followed by addition of a solution of bispinacolatodiboron (51 mg, 0.2 mmol) solution in THF. The reaction mixture was allowed to stir for additional 20 min at −78° C. then warmed up to room temperature. After 2 h, the reaction was quenched by. aq. NH₄Cl solution. This solution was stirred for 1 h and then diluted with ethyl acetate. The aqueous phase was extracted with ethyl acetate (10 mL×2) and the combined organic layers were washed with brine, dried over Na₂SO₄, filtered and concentrated. The crude product was purified by flash chromatography to afford 21 mg (28%) of (6-((3,5-dimethyl-1-tosyl-1H-pyrazol-4-yl) methyl)-4-isobutyl-2-methyl-1-oxo-2,6-dihydro-1H-pyrrolo [3,4-d]pyridazin-7-yl)boronic acid: MS (ES) m/z: 512.2 (M+H)⁺.

Step 5 followed the general Suzuki reaction protocol of Example 1 step 2, using (3-(hydroxymethyl)phenyl)boronic acid. 6-((3,5-dimethyl-1-tosyl-1H-pyrazol-4-yl)methyl)-7-(3-(hydroxymethyl)phenyl)-4-isobutyl-2-methyl-2,6-dihydro-1H-pyrrolo[3,4-c]pyridazin-1-one was isolated in 44% yield: MS (ES) m/z: 574.2 (M+H)⁺.

Step 6: To a solution of the N-tosyl product of step 5 (9.2 mg, 0.016 mmol) in 2 mL of methanol was added 2 mL of 5N sodium hydroxide solution at room temperature. After 3 h the solution was diluted with water (10 mL) and extracted with ethyl acetate (3×10 mL), The organic extracts were washed with brine, dried over Na₂SO₄, filtered and concentrated. The crude product was purified by flash chromatography to afford 5.1 mg (76%) of the title compound: MS (ES) m/z: 420.2 (M+H)⁺.

Example 44. 6-((3,5-dimethyl-1H-pyrazol-4-yl) methyl)-7-(2-fluoro-5-(hydroxymethyl)phenyl)-4-isobutyl-2-methyl-2,6-dihydro-1H-pyrrolo[3,4-d] pyridazin-1-one Steps 1-4: see Example 43.

Step 5 followed the general Suzuki reaction protocol of Example 1 step 2, using the boronic ester from Example 23 Step 1. 6-((3,5-dimethyl-1-tosyl-1H-pyrazol-4-yl)methyl)-7-(3-(hydroxymethyl)phenyl)-4-isobutyl-2-methyl-2,6-dihydro-1H-pyrrolo[3,4-d]pyridazin-1-one was isolated in 44% yield: MS (ES) m/z: 574.2 (M+H)⁺.

Step 6 was performed as described in Example 43. The crude product was purified by flash chromatography to give the title compound in 58% yield: MS (ES) m/z: 438.2 (M+H)⁺.

Example 45. 6-((3,5-dimethyl-1H-pyrazol-4-yl) methyl)-4-isobutyl-2-methyl-7-(3-(2,2,2-trifluoro-1-hydroxyethyl)phenyl)-2,6-dihydro-1H-pyrrolo[3,4-d] pyridazin-1-one Steps 1-4 were shown in Example 43.

Step 5 followed the general Suzuki reaction protocol of Example 1 step 2, using the boronic acid prepared in Step 1 of Example 40. 6-((3,5-dimethyl-1-tosyl-1H-pyrazol-4-yl) methyl)-4-isobutyl-2-methyl-7-(3-(2,2,2-trifluoro-1-hydroxyethyl)phenyl)-2,6-dihydro-1H-pyrrolo[3,4-d] pyridazin-1-one was isolated in 33% yield: MS (ES) m/z: 642.2 (M+H)⁺.

Step 6 was performed as shown in Example 43. Data for the final product: ¹H NMR (CDCl₃, 400 MHz) 7.56-7.51 (m, 2H), 7.49-7.43 (m, 3H), 5.26-5.20 (m, 1H), 5.08 (s, 2H), 3.49 (s, 3H), 2.16-2.11 (m, 2H), 2.09-2.06 (m, 1H), 1.77 (s, 6H), 0.93 (d, 6H, J=6.8). LCMS 488.15 (M+H)⁺.

General Synthesis Scheme for Examples 46-48

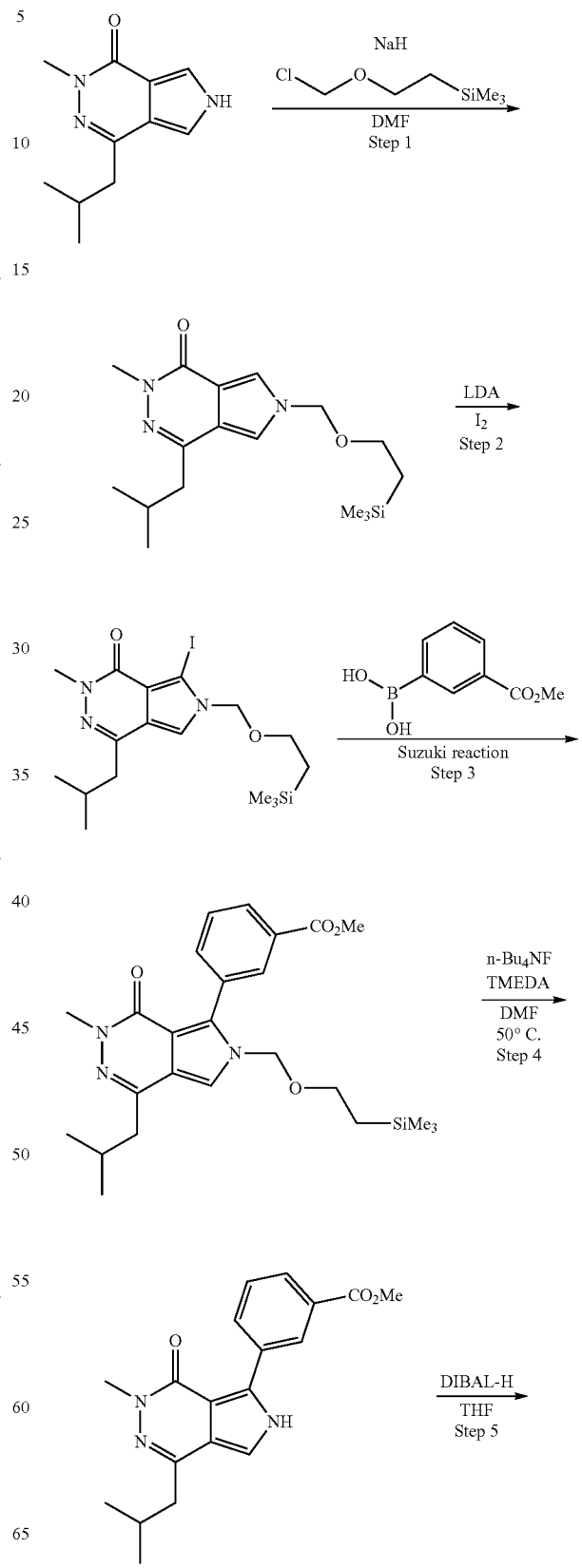

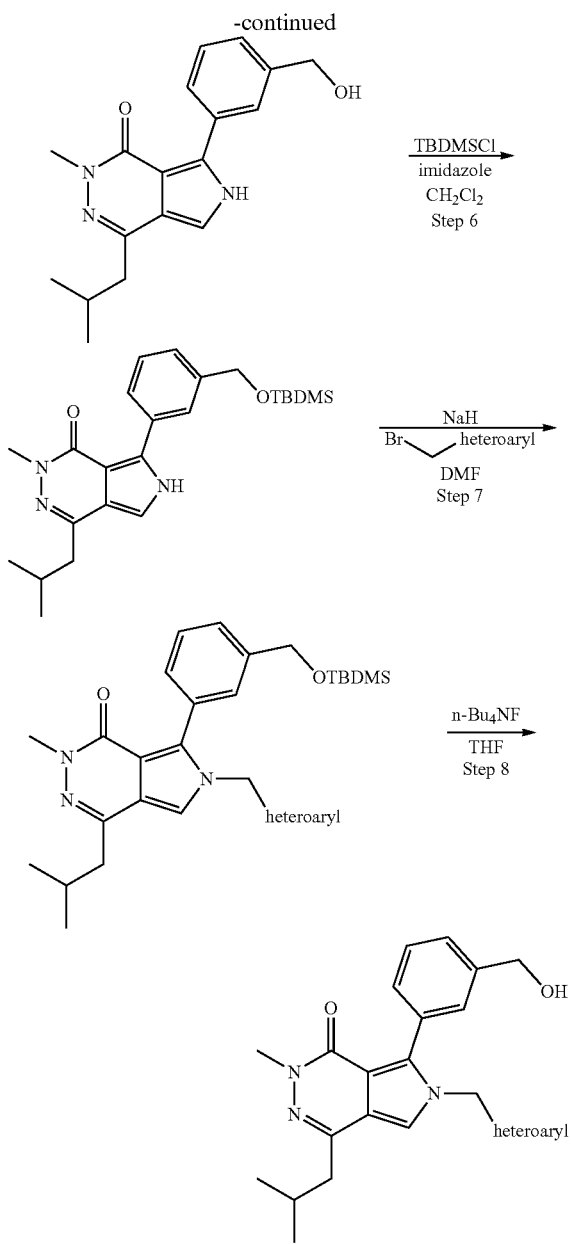

Example 46. 6-((2-chloroquinolin-4-yl)methyl)-7-(3-(hydroxymethyl)phenyl)-4-isobutyl-2-methyl-2,6-dihydro-1H-pyrrolo[3,4-d]pyridazin-1-one Step 1: To a dry 100 mL round bottom flask under argon was added anhydrous DMF (40 mL) and NaH (0.293 g, 60%, 7.31 mmol) then the solution was cooled to 0° C. In a separate flask 4-isobutyl-2-methyl-2,6-dihydro-1H-pyrrolo[3,4-d]pyridazin-1-one (1.021 g, 4.87 mmol) was dissolved in DMF (10 mL) and then this solution was added dropwise by cannula to the NaH/DMF mixture. The reaction mixture was stirred at 0° C. for 2 h and then 2-(trimethylsilyl)ethoxymethyl chloride (1.067 g, 6.33 mmol) was added. After 10 h saturated NH$_4$Cl solution (10 mL) was added and this mixture was extracted with ethyl acetate. The combined organic layers were washed with water (3×25 mL), brine (1×25 mL), dried over Na$_2$SO$_4$ and then concentrated to give a crude solid which was purified using flash chromatography (hexanes:ethyl acetate, 1:1) to give 4-isobutyl-2-methyl-6-((2-(trimethylsilyl)ethoxy)methyl-2,6-dihydro-1H-pyrrolo[3,4-d]pyridazin-1-one as a light brown solid (1.32 g, 82%): $^1$H NMR (CDCl$_3$, 400 MHz) δ 7.58 (d, J=2.0 Hz, 1H), 7.13 (d, J=2.0 Hz, 1H), 5.41 (s, 2H), 3.73 (s, 3H), 3.48 (br t, 2H), 2.58 (d, J=7.0 Hz, 2H), 2.20-2.11 (septet, 1H), 0.97 ppm (d, J=6.6 Hz, 6H), 0.92 (br t, 2H) ppm; $^{13}$C NMR (CDCl$_3$, 100 MHz) δ 159.8, 145.6, 122.6, 120.6, 118.1, 116.3, 81.2, 68.4, 43.8, 39.3, 29.4, 24.1, 19.1, 0.0 ppm; FT-IR (neat, cm$^{-1}$) 3095.9, 2951.7, 2866.8, 1636.4, 1586.7, 1534.7, 1459.8, 1427.8, 1399.8, 1355.7, 1335.8, 1288.9, 1249.6, 1203.7, 1167.8, 1146.7, 1093.4, 1072.6, 1036.8, 1016.8, 997.8, 943.7, 928.7, 943.7, 928.7, 859.5, 833.4, 789.7, 748.6, 710.7, 697.6 cm$^{-1}$; HRMS (ES-TOF) m/z: [M+H]+ Calc'd for C$_{17}$H$_{29}$N$_3$O$_2$Si: 336.2101, Found: 336.2107.

Step 2: To a clean dry flask with stir bar under argon was added the product of Step 1 (1 equiv.) and I$_2$ (2 equiv.) in anhydrous THF. The reaction mixture was cooled to −78° C. and LDA (0.5 M solution in THF, 3 equiv.) was added dropwise over 10 min, The mixture kept at −78° C. for 4 h and then was allowed to warm to room temperature over 15 h. MeOH (10 mL) was added and the mixture was stirred for 30 min. Saturated NH$_4$Cl solution (30 mL) was added and the mixture was extracted with ethyl acetate. The combined organic layers were washed with water (3×25 ML), brine (1×25 mL), dried over Na$_2$SO$_4$ and concentrated to give a crude solid which was purified using flash chromatography to give the desired iodinated product in 68% yield: $^1$H NMR (CDCl$_3$, 400 MHz) δ 7.42 (s, 1H), 5.47 (s, 2H), 3.69 (s, 3H), 3.54 (br t, 2H), 2.53 (d, J=7.0 Hz, 2H), 2.16-2.06 (septet, 1H), 0.97 ppm (d, J=6.6 Hz, 6H), 0.92 (br t, 2H) ppm; $^{13}$C NMR (CDCl$_3$, 100 MHz) δ 159.8, 145.6, 122.6, 1206, 118.1, 116.3, 81.2, 68.4, 43.8, 39.3, 29.4, 24.1, 19.1, 0.0 ppm; FT-IR (neat, cm$^{-1}$) 3095.9, 2951.7, 2866.8, 1636.4, 1586.7, 1534.7, 1459.8, 1427.8, 1399.8, 1355.7, 1335.8, 1288.9, 1249.6, 1203.7, 1167.8, 1146.7, 1093.4, 1072.6, 1036.8, 1016.8, 997.8, 943.7, 928.7, 943.7, 928.7, 859.5, 833.4, 789.7, 748.6, 710.7, 697.6 cm$^{-1}$: HRMS (ES-TOF) m/z: [M+H]+ Calc'd for C$_{17}$H$_{28}$IN$_3$O$_2$Si: 462.1072, Found: 462.1074.

Step 3 followed the general Suzuki reaction protocol of Example 1 step 2, using (3-(methoxycarbonyl)phenyl)boronic acid and the product of Step 2 as coupling partners. methyl 3-(4-isobutyl-2-methyl-1-oxo-6-((2-(trimethylsilyl)ethoxy)methyl)-2,6-dihydro-1H-pyrrolo[3,4-d]pyridazin-7-yl)benzoate was isolated in 67% yield: $^1$H NMR (CDCl$_3$, 400 MHz) δ 8.14 (s, 1H), 8.47 (d, J=7.4 Hz, 1H), 8.30 (d, J=7.7 Hz, 1H) 7.64 (t, J=7.6 Hz, 1H), 5.30 (s, 2H), 3.92 (s, 3H), 3.68 (s, 3H), 3.43 (obscured t, 2H), 2.24-2.16 (septet, 1H), 1.01 (d, J=6.6 Hz, 6H), 0.87 (obscured t, 2H), −0.03 (s, 9H); LCMS (ES) m/z: 470.2 (M+H)+.

Step 4: To a 100 mL round bottom flask was added the product from step 3 (1 equiv) dissolved in DMF. To this was added tetramethyl ethylene diamine (3 equiv) and TBAF (3 equiv). The vessel was fitted with a reflux condenser and heated at 45° C. for 20 h. After confirming the completion of the reaction by LCMS (m/z 340), the reaction mixture was allowed to cool to room temperature and to it was added sat. solution of NH$_4$Cl. The contents were transferred to a separatory funnel containing water, Extraction was done using ethyl acetate and the combined organic layer was washed with water followed by brine, dried over sodium sulfate, and evaporated to give a crude solid in 98% yield: $^1$H NMR (CDCl$_3$, 400 MHz) δ 9.84 (br s, 1H), 8.14 (s, 1H), 8.40 (d, J=8.0 Hz, 1H), 8.34 (s, 1H), 7.95 (d, J=7.8 Hz, 1H) 7.48 (t, J=7.6 Hz, 1H), 7.15 (d, J=2.7 Hz, 1H), 3.90 (s, 3H), 3.74 (s, 3H), 2.60 (d, J=7.4 Hz, 2H), 2.23-2.12 (septet, 1H), 1.01 (d, J=6.6 Hz, 6H).

Step 5: To the product from step 4 (1 equiv) dissolved in a 1:1 mixture of toluene:THF was added diisobutylaluminum hydride (1.0 M in hexanes; 2 equiv) and the mixture was allowed to stir for 3 h. After confirming the completion of the reaction by LCMS (m/z—312), the reaction was quenched by addition of 1N HCl and filtered to remove the insoluble solids. The contents were transferred to a reparatory funnel and extracted using DCM, washed with water and brine, and the organic layer was dried over sodium sulfate and evaporated to give a crude solid in 97% yield: $^1$H NMR (CD$_3$OD, 400 MHz) δ 7.93 (br s, 1H), 7.84 (d, J=7.4 Hz, 1H), 7.46-7.43 (m, 2H), 7.40 (br s, 1H), 4.65 (s, 2H), 3.70 (s, 3H), 2.66 (d, J=7.4 Hz, 2H), 2.27-2.17 (septet, 1H), 1.01 (d, J=6.6 Hz, 6H) ppm.

Step 6: The alcohol from step 5 was added to a round bottom flask and dissolved in DCM. To this was added TBDMS-Cl (2 equiv) and imidazole (2 equiv) and the mixture was allowed to stir for 12 h. After confirming the completion of the reaction by LCMS (m/z—426), the solvents were evaporated and the crude oil was purified by flash chromatography (1:1 Hexanes:EtOAc) to give TBDMS protected alcohol as a pure white solid in 96% yield: $^1$H NMR (CDCl$_3$, 400 MHz) δ 9.44 (s, 1H), 7.87 (d, J=7.4 Hz, 1H), 7.81 (br s, 1H), 7.44-7.40 (obscured t, 1H), 7.350 (br d, 1H), 7.14 (d, J=2.8 hZ, 1H), 4.80 (s, 2H), 3.74 (s, 3H), 2.61 (d, J=7.4 Hz, 2H), 2.24-2.14 (septet, 1H), 1.01 (d, J=6.6 Hz, 6H), 0.95 (s, 9H), 0.12 (s, 6H) ppm.

Step 7: To a dry 100 mL flask with stir bar under argon was added anhydrous degassed DMF, NaH (1.2 equiv) and TBDMS protected alcohol from step 6 (1 equiv). The mixture was allowed to stir for 2 h. Bromomethyl-2-chloroquinoline (1.1 equiv) was dissolved in minimal anhydrous DMF was then added dropwise to the reaction mixture, which was stirred overnight. At this time LCMS (m/z—602) and TLC analysis indicated full conversion. Addition of NH$_4$Cl solution, extraction with ethyl acetate, washing with water and brine, drying over Na$_2$SO$_4$, filtration, and concentration gave a crude solid that was purified by flash chromatography to give alkylated product as a buff solid in 82% yield based on recovered starting material: $^1$H NMR (CDCl$_3$, 400 MHz) δ 8.08 (d, J=8.3 Hz, 1H), 7.78 (obscured t, 2H), 7.69 (br d, 2H), 7.57 (obscured t, 2H), 7.38-7.35 (m, 5H), 7.06 (s, 1H), 6.67 (s, 1H), 5.68 (s, 2H), 4.67 (s, 2H), 3.72 (s, 3H), 2.60 (d, J=7.4 Hz, 2H), 2.19-2.12 (m, 1H), 0.99 (d, J=6.6H, 6H), 0.85 (s, 12H), 0.0006 (s, 6H).

Step 8: The alkylated product obtained in step 7 (1 equiv) was dissolved in THF and to it was added TBAF (1.0 M in THF, 2.0 equiv). After stirring for 2 h and confirming the deprotection of the TBDMS group, the solvents were evaporated and the residue was purified using preparative HPLC. The fractions corresponding to desired product were collected, concentrated, and freeze-dried to give the final product of this Example as a white solid in 65% yield. $^1$H NMR (CDCl$_3$, 400 MHz) δ 8.08 (d, J=7.9 Hz, 1H), 7.78 (t, J=8.3 Hz, 1H), 7.69 (br d, 1H), 7.57 (t, J=8.3 Hz, 2H), 7.49 (br s, 1H), 7.37-7.33 (m, 2H), 7.08 (s, 1H), 6.67 (s, 1H), 5.68 (s, 2H), 4.67 (s, 2H), 3.71 (s, 3H), 2.60 (d, J=7.4 Hz, 2H), 2.20-2.10 (m, 1H), 0.99 (d, J=6.6H, 6H).

Example 47. 6-((1-chloroisoquinolin-4-yl)methyl)-7-(3-(hydroxymethyl)phenyl)-4-isobutyl-2-methyl-2,6-dihydro-1H-pyrrolo[3,4-d]pyridazin-1-one Steps 1-6: see Example 46.

Step 7: To a dry 100 mL flask with stir bar under argon was added anhydrous DMF, NaH (1.2 equiv) and the product from step 6 (1 equiv). The mixture was allowed to stir for 2 h. Bromomethyl 1-chloroisoquinoline (1.1 equiv) dissolved in minimal anhydrous DMF was then added dropwise to the reaction mixture, which was stirred overnight with warming to room temperature. At this time LCMS (m/z—602) and TLC analysis indicated full conversion. Addition of NH$_4$Cl solution, extraction with ethyl acetate, washing with water and brine, drying over Na$_2$SO$_4$, filtration, and concentration gave a crude solid that was purified using flash chromatography to give a buff solid in 71% yield: $^1$H NMR (CDCl$_3$, 400 MHz) δ 8.41 (obscured d, 1H), 7.98 (s, 1H), 7.70 (br d, 2H), 7.48-7.46 (m, 4H), 6.87 (s, 1H), 5.56 (s, 2H), 4.76 (s, 2H), 3.67 (s, 3H), 2.46 (d, J=7.4 Hz, 2H), 2.09-1.99 (septet, 1H), 0.91 (s, 3H), 0.89 (s, 12H), 0.06 (s, 6H).

Step 8 followed the procedure of Step 8 in Example 46, giving the titled product as a white solid: $^1$H NMR (CDCl$_3$, 400 MHz) δ 8.41 (obscured d, 1H), 7.98 (s, 1H), 7.70 (br d, 2H), 7.48-7.46 (m, 5H), 6.87 (s, 1H), 5.56 (s, 2H), 4.76 (s, 2H), 3.67 (s, 3H), 2.46 (d, =7.4 Hz, 2H), 2.09-1.99 (septet, 1H), 0.89 (d, J=6.6 Hz, 6H)

Example 48. 6-(2-(2-chlorophenoxy)ethyl)-7-(3-(hydroxymethyl)phenyl)-4-isobutyl-2-methyl-2,6-dihydro-1H-pyrrolo[3,4-d]pyridazin-1-one Steps 1-6: see Example 46.

Step 7-8: To a dry 50 mL flask with stir bar under argon and cooled to 0° C. was added anhydrous DMF, NaH (1.2 equiv), the product from step 6 of example 46 (1 equiv) and the mixture was allowed to stir for 2 h, 1-(2-bromoethoxy)-2-chlorobenzene (Fort et. al. Synthesis 2004, 15, 2527) (1.5 equiv) was dissolved in minimal DMF was then added dropwise to the reaction mixture, which was stirred overnight with warming to room temperature. At this time LCMS (m/z—581) and TLC analysis indicated full conversion. Addition of NH$_4$Cl solution, extraction with ethyl acetate, washing with water and brine, drying over Na$_2$SO$_4$, filtration, and concentration gave a crude solid (~25 mg) that was re-dissolved in TBAF solution (1.0 M in THF, 2.0 equiv). After stirring for 2 h and confirming the deprotection of the TBDMS group, the solvents were evaporated and the residue was purified using preparative HPLC. The fractions corresponding to desired product were collected, concentrated, and freeze-dried to give the final product of this Example as a white solid in 40% yield over two steps: $^1$H NMR (CD$_3$OD, 400 MHz) δ 7.55 (s, 1H), 7.27-7.22 (br, 4H), 7.14 (br d, 1H), 6.99 (br t, 1H), 6.71 (obscured t, 2H), 4.46 (s, 1H), 4.33 (br t, 2H), 4.06 (br t, 2H), 3.41 (s, 3H), 2.43 (d, J=7.4 Hz, 2H), 2.04-2.00 (m, 1H), 0.78 (d, J=6.6 Hz, 6H).

Synthesis Scheme for Examples 49-52

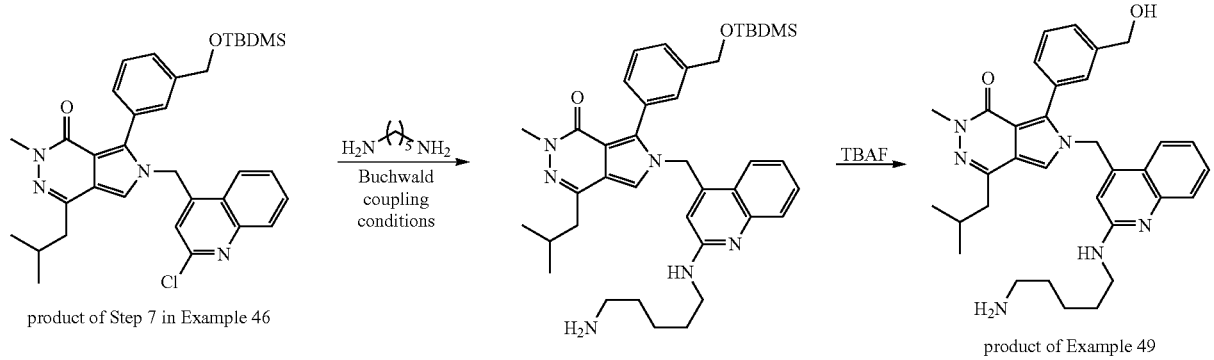

product of Step 7 in Example 46 product of Example 49

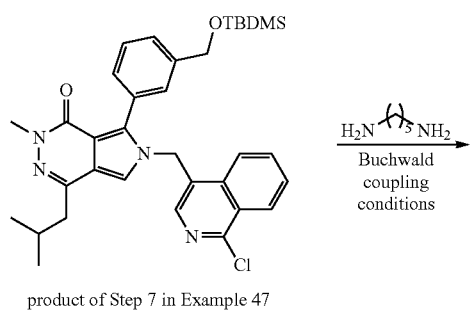

product of Step 7 in Example 47

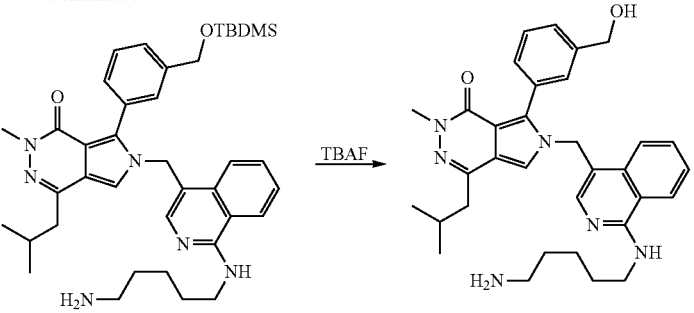

product of Example 50

1) acylation
2) disilyation amino acid coupling and full deprotection

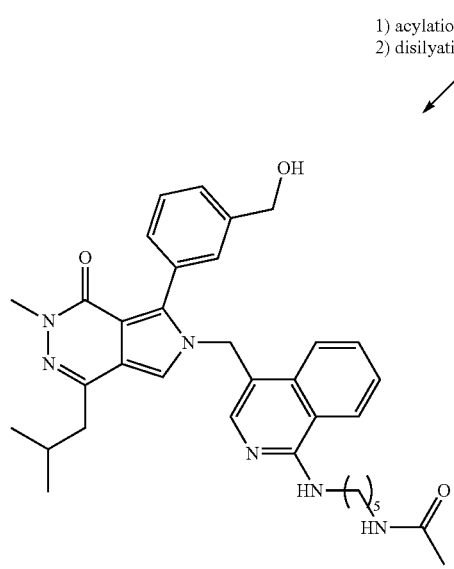

product of Example 51

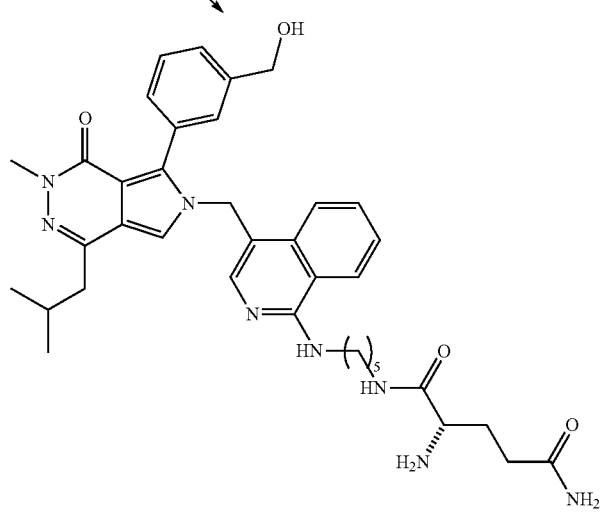

product of Example 52

Example 49. 6-((2-((5-aminopentyl)amino)quinolin-4-yl)methyl)-7-(3-(hydroxymethyl)phenyl)-4-isobutyl-2-methyl-2,6-dihydro-1H-pyrrolo[3,4-d]pyridazin-1-one Step 1: To a microwave vial containing product from step 7 from example 46 (1 equiv) added NaOtBu (1.5 equiv), Pd(OAc)$_2$ (0.001 equiv), BINAP (0.002 equiv), 1,5-diamino pentane (3 equiv) and toluene (5 mL). The contents were mixed well and then degassed by bubbling with argon for 5 min. The reaction mixture was then subjected to microwave heating for 3 h at 100° C. After confirming the completion of the reaction by LCMS (m/z 667), the reaction mixture was filtered to remove insoluble solids and the evaporation of solvents give the coupling product as a crude oil that was taken to the next step.

Step 2: The crude from step 1 was dissolved in THF and to it was added TBAF (1.0 M in THF, 2.0 equiv). After stirring for 2 h and confirming the deprotection of TBDMS group by LCMS, the solvents were evaporated and the residue was purified using preparative HPLC. The fractions corresponding to desired product were collected, concentrated, and freeze-dried to give the final product of this Example as a white solid in 45% yield: $^1$H NMR (CD$_3$OD, 400 MHz) δ 7.91 (s, 1H), 7.79 (br d, 1H), 7.56 (br s, 2H), 7.50-7.46 (m, 1H), 7.47-7.43 (m, 3H), 7.15 (s, 1H), 6.85 (s, 1H), 5.48 (br t, 1H), 5.34 (s, 2H), 4.82 (s, 2H) 4.76 (s, 2H), 3.67 (s, 3H), 3.65-3.62 (obscured t, 2H), 2.75 (br t, 2H), 2.41 (d, J=7.4 Hz, 2H), 2.02-1.97 (m, 1H), 1.56 (br m, 6H), 0.93 (s, 9H), 0.86 (d, J=6.6 Hz, 6H), 0.10 (s, 6H).

Example 50. 6-((1-((5-aminopentyl)amino)isoquinolin-4-yl)methyl)-7-(3-(hydroxymethyl)phenyl)-4-isobutyl-2-methyl-2,6-dihydro-1H-pyrrolo[3,4-d]pyridazin-1-one Step 1: Followed Step 1 of Example 49 using the product from step 7 from example 47.
Step 2: Followed Step 2 of Example 49: $^1$H NMR (CDCl$_3$, 400 MHz) δ 7.91 (s, 1H), 7.79 (br d, 1H), 7.56 (br s, 2H), 7.50-7.46 (m, 1H), 7.47-7.43 (m, 3H), 7.15 (s, 1H), 6.85 (s, 1H), 5.48 (br t, 1H), 5.34 (s, 2H), 4.82 (s, 2H) 4.76 (s, 2H), 3.67 (s, 3H), 3.65-3.62 (obscured t, 2H), 2.75 (br t, 2H), 2.41 (d, J=7.4 Hz, 2H), 2.02-1.97 (m, 1H), 1.56 (br m, 6H), 0.93 (s, 9H), 0.86 (d, J=6.6 Hz, 6H), 0.10 (s, 6H).

Example 51. N-(5-((4-((7-(3-(hydroxymethyl)phenyl)-4-isobutyl-2-methyl-1-oxo-1H-pyrrolo[3,4-d]pyridazin-6(2H)-yl)methyl)quinolin-2-yl)amino)pentyl)acetamide The product of Step 1 of example 50 was dissolved in dichloromethane. Hunig's base (2 equiv) and acetyl chloride (1.5 equiv) were added and the reaction mixture was allowed to stir overnight at room temperature. The solvents were evaporated to give a crude oil which was dissolved in THF and to this was added (n-Bu)$_4$NF (1.0 M in THF, 2.0 equiv). After stirring for 2 h the solvents were evaporated and the residue was purified using preparative HPLC. The fractions corresponding to desired product were collected, concentrated, and freeze-dried to give the final product of this Example as a white solid in 30% yield: $^1$H NMR (CD$_3$OD, 400 MHz) δ 8.45 (d, J=8.4 Hz, 1H), 7.89-7.85 (obscured t, 1H), 7.77-7.76 (obscured t, 1H), 7.65 (d, J=8.2 Hz, 1H), 7.63 (s, 1H), 7.42-7.38 (br m, 3H), 7.33-7.30 (m, 1H), 6.90 (s, 1H), 5.64 (s, 2H), 4.60 (s, 2H), 3.61 (s, 3H), 3.56 (t, J=7.3 Hz, 2H), 3.26 (s, 1H), 3.24-3.20 (br t, 2H), 3.11 (s, 1H), 2.60 (d, J=7.4 Hz, 2H), 2.19-2.13 (m, 2H), 1.86-1.82 (m, 2H), 1.76-1.68 (m, 2H), 1.56-1.50 (m, 2H), 1.36 (s, 1H), 0.95 (d, J=6.6 Hz, 6H).

Example 52. (S)-4-amino-6-((5-((4-((7-(3-(hydroxymethyl)phenyl)-4-isobutyl-2-methyl-1-oxo-1H-pyrrolo[3,4-d]pyridazin-6(2H)-yl)methyl)isoquinolin-1-yl)amino)pentyl)amino)-5-oxohexanamide The product from step 1 from example 50 (1 equiv) was dissolved in DMF and to it was added Boc-OH-glutamine (1.5 equiv), diisopropylethyl amine (2 equiv), and HATU (1.5 equiv). This mixture was allowed to stir overnight. After confirming the completion of the reaction by LCMS (m/z 895) the reaction was quenched by the addition of saturated NH$_4$Cl and then extracted with ethyl acetate. After washing the organic layer with water and brine it was dried over Na$_2$SO$_4$, filtered and the solvent was evaporated to give a crude oil. The crude material was re-dissolved in minimal THF and to it was added excess Ha (4.0 M in 1,4-dioxane). This reaction mixture was allowed to stir for 2 h and constantly monitored for completion using LCMS (m/z 681). Once the disappearance of starting material was confirmed, the reaction mixture was quenched with NaHCO$_3$, the organic layer was concentrated and the crude material was purified using preparative HPLC. The fractions corresponding to desired product were collected, concentrated, and freeze-dried to give the final product of this Example as a white solid in 45% yield: $^1$H NMR (CD$_3$OD, 400 MHz) δ 8.45 (d, J=8.4 Hz, 1H), 7.89-7.85 (br t, 1H), 7.78-7.74 (br t, 1H), 7.64 (obscured d, 1H), 7.63 (s, 1H), 7.41-7.39 (br m, 2H), 7.33-7.31 (m, 1H), 6.89 (s, 1H), 5.64 (s, 2H), 4.61 (s, 2H), 3.88 (t, 1H), 3.61 (s, 3H), 3.56 (t, J=7.3 Hz, 2H), 2.60 (d, J=7.4 Hz, 2H), 2.43-2.38 (m, 2H), 2.19-2.03 (m, 4H), 1.86-1.79 (m, 3H), 1.68-1.63 (m, 3H), 1.55-1.49 (m, 2H), 1.28 (s, 2H), 0.95 (d, J=6.6 Hz, 6H).

Biological Activity

Example 53. Biological Activity of Selected Compounds of the Invention

Specific Examples 1-52 of compounds of the invention, with estimated EC$_{50}$ values determined using an MTT assay for 4-day viability of Raji (Burkitt's) lymphoma cells, a cell line known to highly express MCT1 and to be sensitive to small molecule MCT inhibitors,[4] are shown in Table 2. Assay protocols follow those described in the literature.[4] Other assays that are not described here but that are standard in the field, such as an assay for competitive inhibition of transport of radiolabeled lactic acid, an MCT substrate, may also be useful in establishing mechanism of action of these compounds.

TABLE 2

| Example | approximate potency (EC$_{50}$) |
|---|---|
| 1 | ≤20 nM |
| 2 | 100 nM |
| 3 | 1-10 μM |
| 4 | 200 nM |
| 5 | 160 nM |
| 6 | ≤20 nM |
| 7 | ≤20 nM |
| 8 | 34 nM |
| 9 | ≤20 nM |
| 10 | 90 nM |
| 11 | 25 nM |
| 12 | 75 nM |
| 13 | 50 nM |
| 14 | <20 nM |
| 15 | <20 nM |
| 16 | 220 nM |
| 17 | 100 nM |
| 18 | 900 nM |
| 19 | 70 nM |
| 20 | ≤20 nM |
| 21 | ≤20 nM |
| 22 | ≤20 nM |
| 23 | ≤20 nM |
| 24 | 1 μM |
| 25 | 300 nM |
| 26 | 90 nM |
| 27 | 80 nM |
| 28 | 40 nM |
| 29 | 80 nM |
| 30 | 600 nM |
| 31 | 100 nM |
| 32 | 900 nM |
| 33 | 70 nM |
| 34 | 1 μM |
| 35 | 80 nM |
| 36 | 100 nM |
| 37 | 100 nM |
| 38 | ≤20 nM |
| 39 | 90 nM |
| 40 | 50 nM |
| 41 | 800 nM |
| 42 | 1-10 μM |
| 43 | 500 nM |
| 44 | 200 nM |
| 45 | ≤20 nM |
| 46 | 1-10 μM |
| 47 | 1-10 μM |
| 48 | 1-10 μM |
| 49 | 1-10 μM |
| 50 | ≤20 nM |
| 51 | ≤20 nM |
| 52 | ≤20 nM |

Example 53, Mouse Xenograft Studies

The in vivo effects of a few selected agents have been evaluated in mouse xenograft models and many potent compounds from Example 53 were found to be effective in arresting tumor growth or in provoking tumor regression.

Protocols follow those described in the literature.[4] Mice were transplanted with cultured tumor cells and, after an incubation period (typically 10 days), mice were left untreated or were treated daily with a 30 mg/kg dose of the test compound. Tumor volumes were measured with calipers over ~20 days of treatment. Tumors were excised and weighed at the end of treatment.

Figure 3:
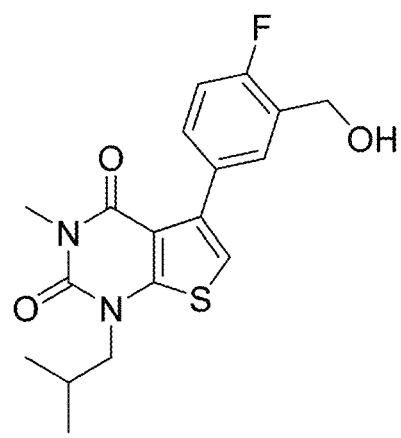
FIG. 3 shows the chemical structure of the compound of Example 9 (SR-11105).
Figure 4:
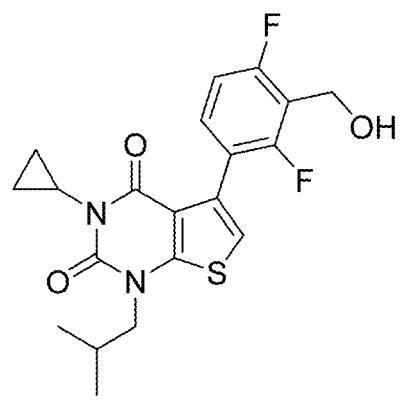
FIG. 4 shows the chemical structure of the compound of Example 21 (SR-13779).

In two experiments using Raji Burkitt's lymphoma cells[4], the compounds studied were the product of example 9 (FIG. 3), code named SR-11105, and the product of example 21 (FIG. 4), code named SR-13779.

Figure 5:
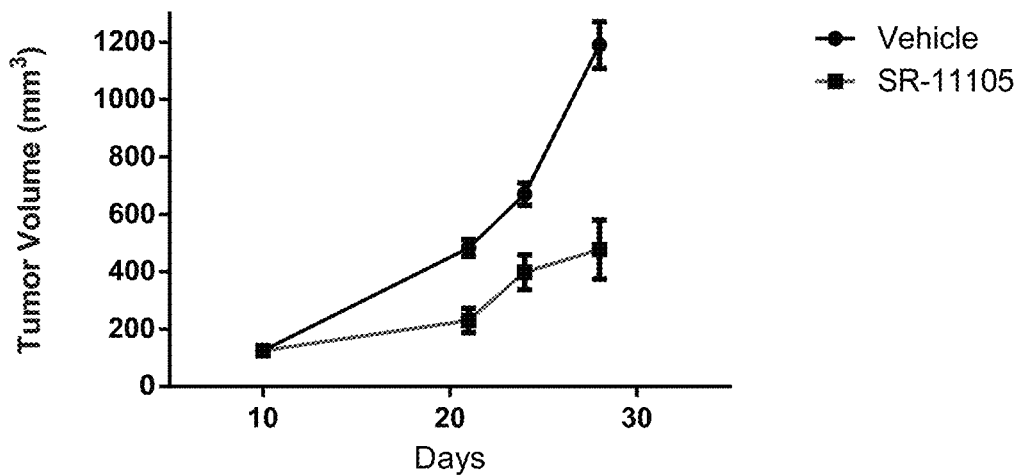
FIG. 5 shows a graph indicating the time course of tumor volume reduction caused by administration of the compound of Example 9 (SR-11105) relative to vehicle.

Treatment with SR-11105 led to a significant reduction of tumor growth rate over time (FIG. 5).

Figure 6:
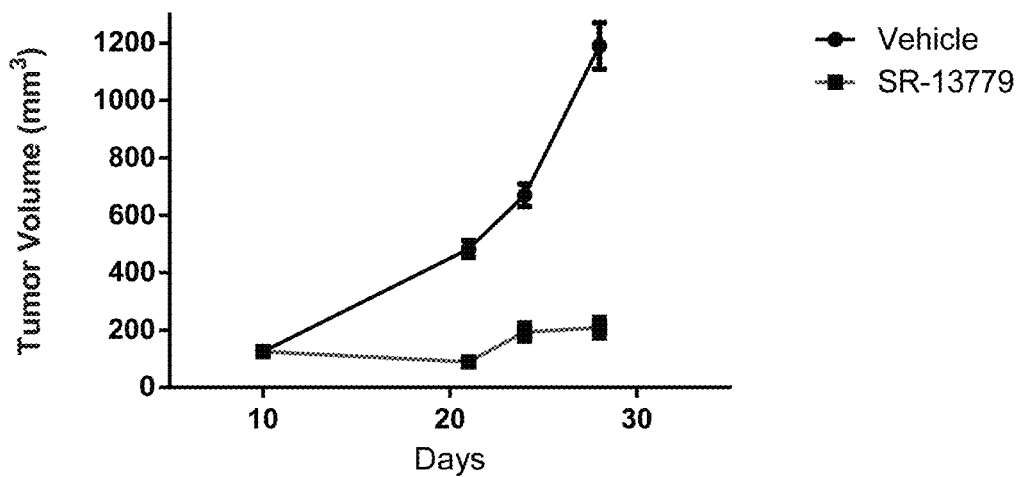
FIG. 6 shows a graph indicating the time course of tumor volume reduction caused by administration of the compound of Example 21 (SR-13779) relative to vehicle.

Treatment with SR-13779 effectively blocked tumor growth over time (FIG. 6).

Figure 7:
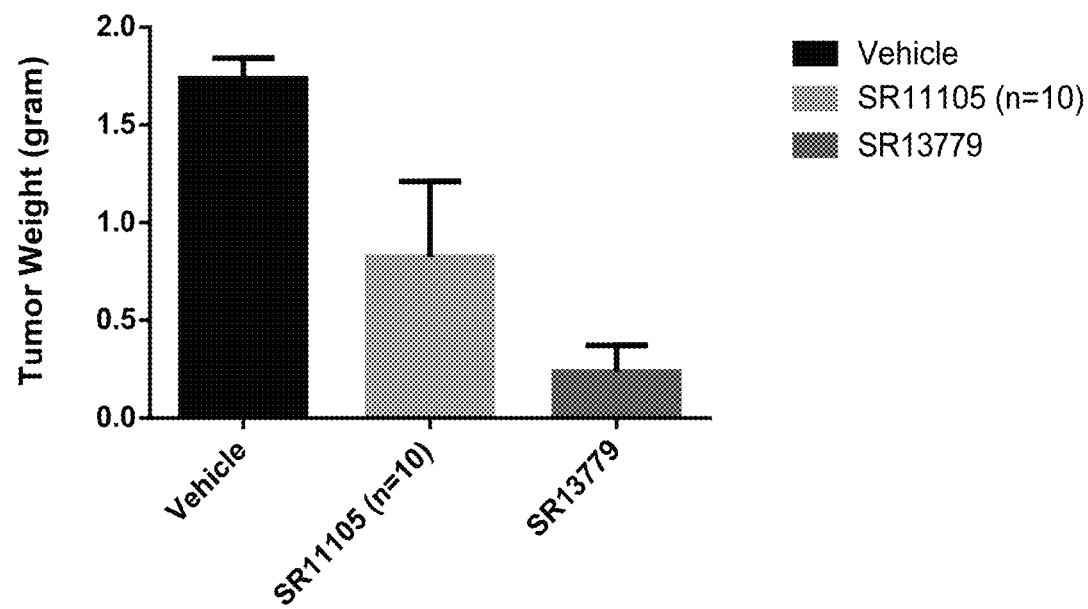
FIG. 7 shows a comparison of tumor weight following administration of the compounds of Examples 9 (SR-11105) and 21 (SR-13779) relative to vehicle.

A significant reduction in final tumor mass was observed, both when using SR-11105 and SR-13779, with tumor mass measured at day 29 in each case (FIG. 7). SR-13779 had the more pronounced effect.

Figure 8:
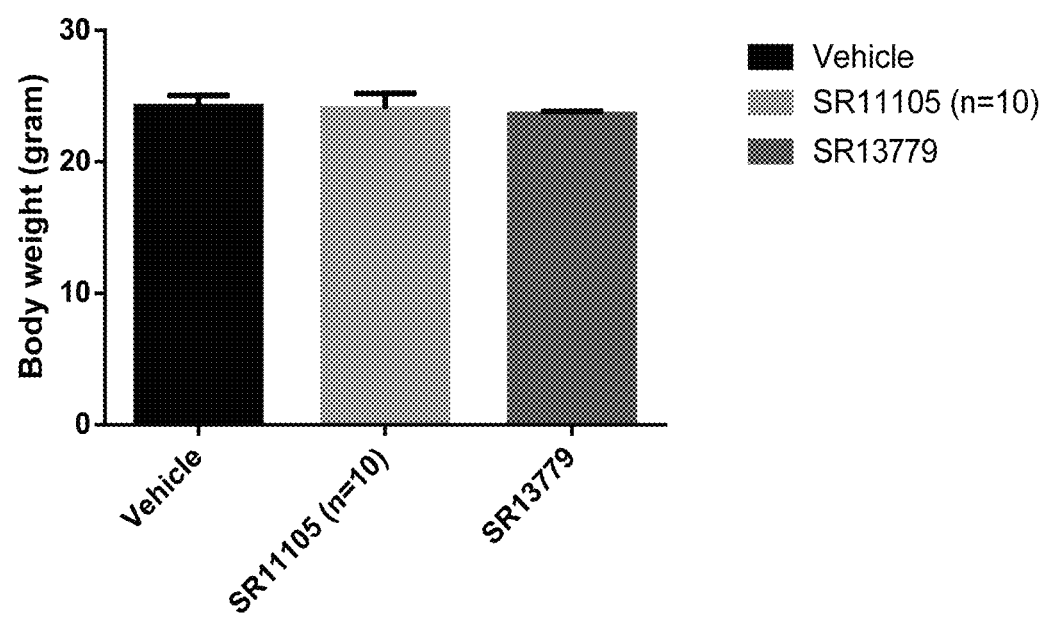
FIG. 8 shows a comparison of animal body weight following administration of the compounds of Examples 9 (SR-11105) and 21 (SR-13779) relative to vehicle.

Mice that had been treated with either SR-11105 or SR-13779 maintained their body weight over the course of the study (FIG. 8), indicating these compounds are safe in treated mice.

Variations

It is understood that certain claimed molecules may stably exist in with isotopic variants among specific substituents, such as deuterium or tritium in the place of hydrogen. Such isotopic variants also fall within the scope of the invention.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

It is also understood that certain groups such as amines bear a net charge. When such a group or groups are present in a "claimed compound", pharmaceutically acceptable salt forms of the structure are implicitly encompassed in the claims as well, For example, a claim for a compound with one or more amino groups present in the structure also implicitly claims all pharmaceutically acceptable salt forms, such as hydrochloride, methanesulfonyl, formate, oxalate, tartrate salts, and the like.

It is understood that certain "claimed compounds" may stably exist as hydrates or solvates. Such differing forms are also implicitly encompassed in the claims, Hydrates refer to molecules of water present in the crystal lattice. Solvates refer to molecules of a relatively benign solvent, such as ethanol, present in the crystal lattice.

It is understood that certain "claimed compounds" in any form, including as a salt, hydrate, or solvate, may stably exist in multiple solid crystalline and/or amorphous forms. Such forms may confer different physical properties (e.g., rate of dissolution, stability, hydroscopicity).

Such differing solid forms are also implicitly encompassed in the claims.

CITED DOCUMENTS

1. Warburg, O. On the origin of cancer cells. *Science* 1956, 123, 309-314.
2. Koppenol, W. H.; Bounds, P. L.; Dang, C. V. Otto Warburg's contributions to current concepts of cancer metabolism. *Nature Rev. Cancer* 2011, 11, 325-327.
3. Halestrap, A. P. The SLC16 gene family—structure, role and regulation in health and disease. *Mol. Asp. Med.* 2013, 34, 337-349.
4. Doherty, J. R.; Yang, C.; Scott, K.; Cameron M. D.; Fallahi, M.; Li, W; Hall, M. A.; Amelio, A. L.; Mishra, J. K.; Li, F; Tortosa, M.; Genau, H. M.; Rounbehler, R. J.; Yungi, L.; Dang, C. V.; Kumar, K. G.; Butler, A. A.; Bannister, T. D.; Hooper A. T.; Unsal-Kacmaz, K.; Roush, W. R.; and Cleveland, J. L. Blocking lactate export by inhibiting the myc target MCT1 disables glycolysis and glutathione synthesis. *Cancer Res.* 2014, 74, 908-920.
5. Ullah, M. S.; Davies, A. J.; Halestrap, A. P. The plasma membrane lactate transporter MCT4, but not MCT1, is up-regulated by hypoxia through a HIF-1α-dependent mechanism. *J. Biol. Chem.* 2006, 281, 9030-9037.
6. Dang, C. V. The interplay between MYC and HIF in the Warburg effect. *Ernst Schering Found Symp. Proc.* 2007, 35-53.
7. Vaupel, P.; Mayer, A. Hypoxia in cancer; significance and impact on clinical outcome. *Cancer Metastasis Rev.* 2007, 26. 225-239.
8. Kizaka-Kondoh, S.; Inoue, M.; Harada, H.; Hiraoka, M. Tumor hypoxia: a target for selective cancer therapy. *Cancer Sci.* 2003, 94, 1021-1028.
9. Le Floch, R.; Chiche, J.; Marchiq, I.; Naiken, T.; Ilk, K.; Murray, C. M.; Critchlow, S. E.; Roux, D.; Simon, M. P.; Pouyssegur, J. CD147 subunit of lactate/$H^+$ symporters MCT1 and hypoxia-inducible MCT4 is critical for energetics and growth of glycolytic tumors. *Proc. Natl. Acad. Sci. USA* 2011, 108, 16663-16668.
10. Sonveaux, P.; Vegran, F.; Schroeder, T.; Wergin, M. C.; Verrax, J.; Rabbani, Z. N.; De Saedeleer, C.; J.; Kennedy, K. M.; Diepart, C.; Jordan, B. F.; Kelley, M. J.; Gallez, B.; Wahl, M. L.; Feron, O.; Dewhirst, M. W. Targeting lactate-fueled respiration selectively kills hypoxic tumor cells in mice. *J. Clin Invest.* 2008, 118, 3930-3942.
11. Broer, S.; Schneider, H.; Broer, A.; Rahman, B.; Hamprecht, B.; Deitmer, J. W. Characterization of the monocarboxylate transporter 1 expressed in Xenopuslaevis oocytes by changes in cytosolic pH. *Biochem. J.* 1998, 333, 167-174.
12. Jackson, V, N.; Halestrap, A. P. The kinetics, substrate, and inhibitor specificity of the monocarboxylate (lactate) transporter of rat liver cells determined using the fluorescent intracellular pH indicator, 2',7'-bis(carboxyethyl)-5 (6)-carboxyfluorescein. *J. Biological Chem.* 1996, 271, 861-868.
13. Kobayashi, M.; Itagaki, S.; Hirano, T.; Iseki, K. mechanism of L-lactic acid transport in L6 skeletal muscle cells. *Drug Metab. Pharmacokin.* 2004, 19, 363-368.
14. Wang, Q.; Morris, M. E. Flavonoids modulate monocarboxylate transporter-1-mediated transport of γ-hydroxybutyrate in vitro and in vivo. *Drug Metabolism and Disposition* 2007, 35, 201-208.
15, Draoui, N.; Schicke, O.; Fernandes A.; Drozak, X.; Fady, N.; Dumont, A.; Douxfils, J.; Hermans, E.; Dope, J-M.; Corbau, R.; Marchand, A.; Chaffin, P.; Sonveaux, P.; Feron, O.; Riant O. Synthesis and pharmacological evaluation of carboxycoumarins as a new antitumor treatment targeting lactate transport in cancer cells. *Bioorg. Med. Chem.* 2013, 21, 7107-7117.
16. Mereddy, V. R.; Drewes, L. R.; Alam, M. A., Jonnalagadda, S. K.; Gurrapu, S. Preparation of benzopyran derivatives and related compounds as MCT1 inhibitors. PCT Int. Appl, 2013, WO2013109972 A2 20130725.
17. Wang, H, and Bannister, T. D.; Synthesis and Structure-Activity Relationships of Pteridine Dione and Trione Monocarboxylate Transporter 1 Inhibitors, *J. Med. Chem.*, 2014, 57 (17), 7317-7324
18. Murray, C. M.; Hutchinson, R.; Bantick, J. R.; Belfield, G. P.; Benjamin, A. D.; Brazrna, D.; Bundick, R. V.; Cook, I. D.; Craggs, R. I.; Edwards, S.; Evans, L. R.; Harrison, R.; Holness, E.; Jackson, A. P.; Jackson, C. G.; Kingston, L. P.; Perry, M. W. D.; Ross, A. R. J.; Rugman, P. A.; Sidhu, S. S.; Sullivan, M.; Taylor-Fishwick, D. A.; Walker, P. C.; Whitehead, Y. M.; Wilkinson, D. J.; Wright, A.; Donald, D, Monocarboxylate transporter MCT1 is a target for immunosuppression. *Nat. Chem. Biol.* 2005, 1, 371-376.

19. Guile, S. D.; Bantick, J. R.; Cheshire, D. R.; Cooper, M. E.; Davis, A. M.; Donald, D. K.; Evans, R.; Eyssade, C.; Ferguson, D. D.; Hill, S.; Hutchinson, R.; Ingall, A. H.; Kingston, L. P.; Marin, I.; Martin, B. P.; Mohammed, R. T.; Murry, C.; Perry, M. W. D; Reynolds, R. H.; Thorne, P, V.; Wilkinson, D. J.; Withnall, J. Potent blockers of the monocarboxylate transporter MCT1: novel immuno-modulatory compounds. *Bioorg. Med. Chem. Lett.* 2006, 16, 2260-2265.

20. Guile, S. D.; Bantick, J. R.; Cooper, M. E.; Donald, D. K.; Eyssade, C.; Ingall, A. H.; Lewis, R. J.; Martin, B. P.; Mohammed, R. T.; Potter, T. J.; Reynolds, R. H.; St-Gallay, S. A.; Wright, A. D. Optimization of monocarboxylate transporter 1 blockers through analysis and modulation of atropisomer interconversion properties. *J. Med. Chem.* 2007, 50, 254-263.

21. Bueno, V.; Binet, I.; Steger, U.; Bundick, R.; Ferguson, D.; Murray, C.; Donald, D.; Wood, K. The specific monocarboxylate transporter (MCT1) inhibitor, AR-C117977, a novel immunosuppressant, prolongs allograft survival in the mouse. *Transplantation* 2007, 84, 1204-1207.

22. Ovens, M. J.; Davies, A. J.; Wilson, M. C.; Murray, C. M.; Halestrap, A. P. AR-C155858 is a potent inhibitor of monocarboxylate transporters MCT1 and MCT2 that binds to an intracellular site involving transmembrane helices 7-10, *Biochem. J.* 2010, 425, 523-530.

23. Critchlow, S. E.; Tate, L. Use of a MCT1 inhibitor in the treatment of cancers expressing MCT1 over MCT4. PCT Int. Appl. 2010, WO2010089580 A1 20100812.

24. http.//clinicaltrials.gov/show/NCT01791595.

25. Polanski, R.; Hodgkinson, C. L.; Fusi, A.; Nonaka, D.; Priest, L.; Kelly, P.; Trapani, F.; Bishop, P. W.; White, A.; Critchlow; S. E.; Smith, P. D.; Blackhall F.; Dive, C.; Morrow, C. J. Activity of the monocarboxylate transporter 1 inhibitor AZD3965 in small cell lung cancer. *Clin. Cancer Res.* 2014, 20, 926-937.

26. Michne, W. F.; Schroeder, J. D.; Guiles, J. W.; Treasurywala, A. M.; Weigelt, C. A.; Stansberry, M. F.; McAvoy, E.; Shah, C. R.; Bump, E.; Schlegel, D. Novel Inhibitors of the Nuclear Factor of Activated T Cells (NFAT)-Mediated Transcription of .beta.-Galactosidase: Potential Immunosuppressive and Antiinflammatory Agents. *J. Med. Chem.,* 1995, 38 (14), 2557-2569.

27. Otonkoski, T; Jiao, H; Kaminen-Ahola, N; et al. Physical exercise induced hypoglycemia caused by failed silencing of monocarboxylate transporter 1 in pancreatic beta cells. *Am J Hum Genet* 2007; 81, 467-474.

28. Zhao, C.; Wilson, M. C.; Schuit, F.; Halestrap, A. P.; Rutter, G. A. Expression and distribution of lactate/monocarboxylate transporter isoforms in pancreatic islets and the exocrine pancreas. *Diabetes* 2001; 50, 361-366.

29. Sekine, N.; Cirulli, Regazzi, R.; et al. Low lactate dehydrogenase and high mitochondrial glycerol phosphate dehydrogenase in pancreatic beta-cells. Potential role in nutrient sensing. *J Biol Chem* 1994, 269, 4895-4902.

30. Otonkoski, T.; Kaminen, N.; Ustinov, J.; et al. Physical exercise-induced hyperinsulinemic hypoglycemia is an autosomal-dominant trait characterized by abnormal pyruvate-induced insulin release. *Diabetes* 2003; 52, 199-204.

31. Pullen T. J.; Sylow, L.; Sun, G.; Halestrap, A. P.; Richter, E. A.; Rutter, G. A. Overexpression of Monocarboxylate Transporter-1 (Slc16a1) in Mouse Pancreatic beta-Cells Leads to Relative Hyperinsulinism During Exercise, *Diabetes* 2012, 61, 1719-1725.

32. Best, L.; Yates, A. P.; Meats, J. E.; Tomlinson, S. Effects of lactate on pancreatic islets: Lactate efflux as a possible determinant of islet-cell depolarization by glucose. *Biochem. J.* 1989; 259, 507-511.

While the invention has been described and exemplified in sufficient detail for those skilled in this art to make and use it, various alternatives, modifications, and improvements will be apparent to those skilled in the art without departing from the spirit and scope of the claims.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed, Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A compound of formula A

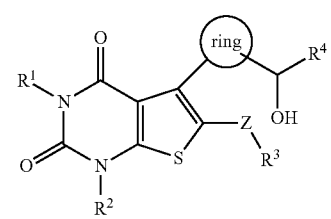

wherein:
$R^1$ is selected from the group consisting of, $(C_1-C_6)$alkyl, $(C_3-C_6)$branched alkyl, and $(C_3-C_7)$cycloalkyl;
$R^2$ is selected from the group consisting of, $(C_1-C_6)$alkyl, and $(C_3-C_6)$branched alkyl;
$R^3$ is a monocyclic aryl or a monocyclic or bicyclic heteroaryl group, wherein the aryl or heteroaryl can be substituted or unsubstituted;
$R^4$ is hydrogen, $CF_3$, $(C_1-C_6)$alkyl, or $(C_3-C_6)$branched alkyl;
Z is $CH_2$;
the cyclic group indicated as "ring" is an aryl or heteroaryl group of any one of the following:

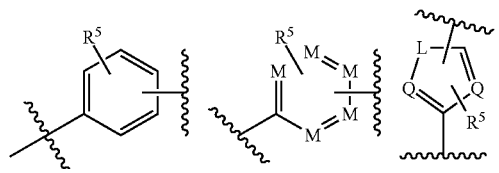

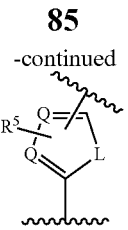

wherein wavy lines indicate points of bonding, and wherein M is independently selected CH or N, provided that M group can be a nitrogen atom in 0, 1, or 2 instances;

L is S, O, NH, N($C_1$-$C_6$)alkyl, or NCF$_3$, each Q is independently CH or N;

wherein $R^5$ is optionally present, and when present, $R^5$ is one to four instances of independently selected F, Cl, Br, CF$_3$, ($C_1$-$C_6$)alkyl, OCF$_3$O($C_1$-$C_6$)alkyl, or CO—($C_1$-$C_6$)alkyl;

or a pharmaceutically acceptable salt thereof.

2. The compound of claim 1, wherein the $R^3$ group is monocyclic, and is of one of the following formulas

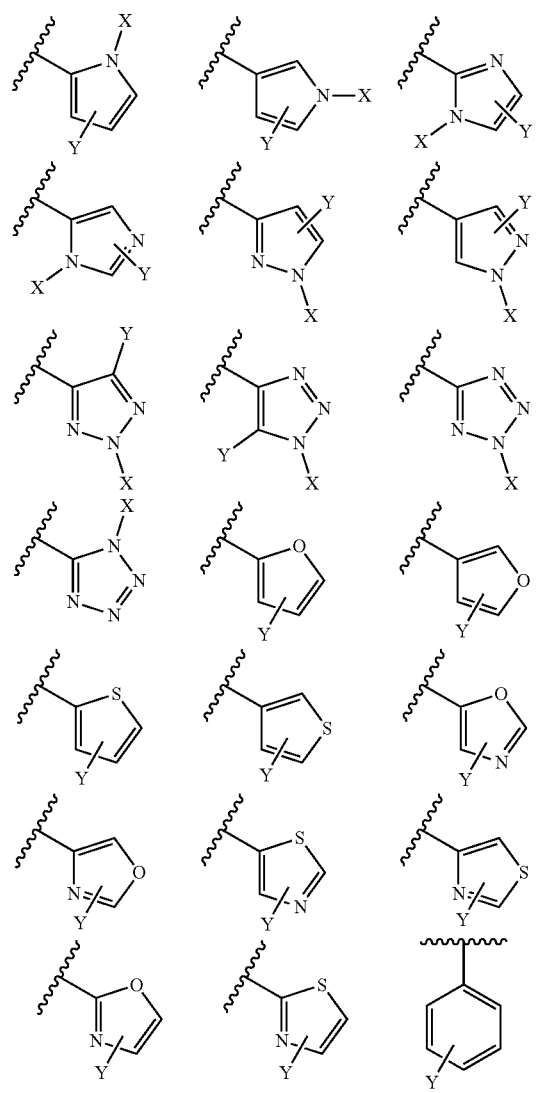

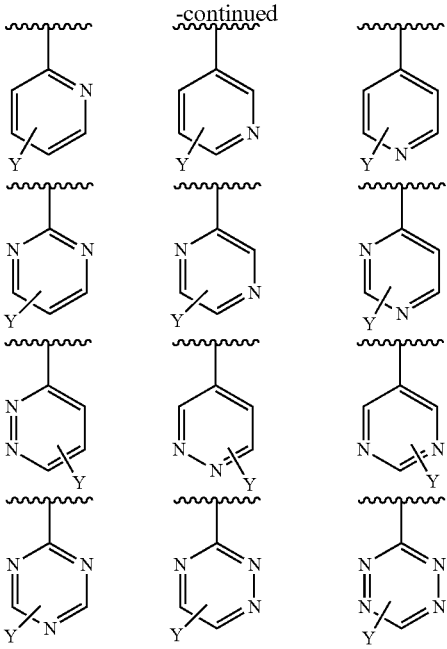

wherein
X is H, ($C_1$-$C_6$)alkyl, or CF$_3$; and
Y is optionally present and, when Y is present, Y is 1-3 instances of a substituent selected from the group consisting of F, Cl, Br, CF$_3$, ($C_1$-$C_6$)alkyl, O($C_1$-$C_6$)alkyl, NH$_2$, NH($C_1$-$C_6$)alkyl, N(($C_1$-$C_6$)alkyl)$_2$, NH—(CH$_2$)$_j$—CH$_2$-Q, and

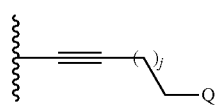

wherein j=2-6 and Q is one of the following groups

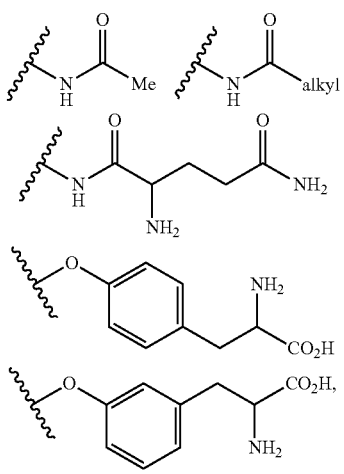

wherein a wavy line indicates a point of bonding.

3. The compound of claim 1, wherein $R^1$ is Me or cycloalkyl, $R^2$ is alkyl or branched alkyl, Z is CH$_2$ or CH(Me), $R^4$ is H, Me, or CF$_3$, the cyclic group indicated as "ring" is aryl or heteroaryl, and all other groups are as specified in claim 1.

4. The compound of claim 1, wherein the compound is any one of the following including all stereoisomeric forms, all isotopic forms, all crystalline and amorphous forms, and all pharmaceutically acceptable salt forms thereof:
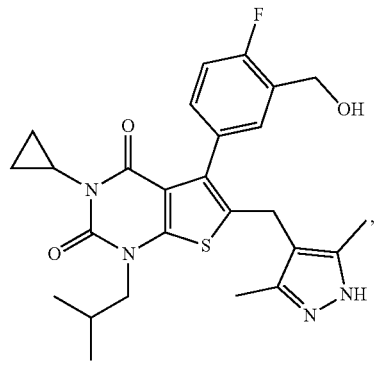
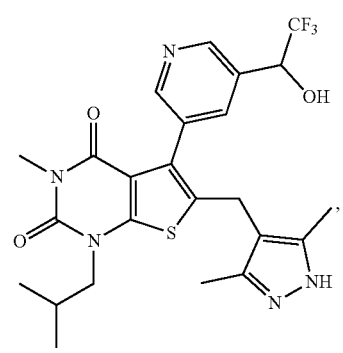
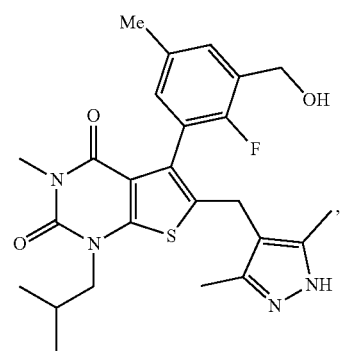
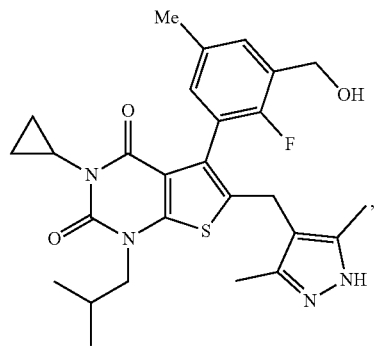
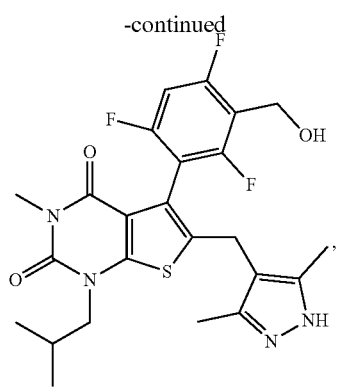
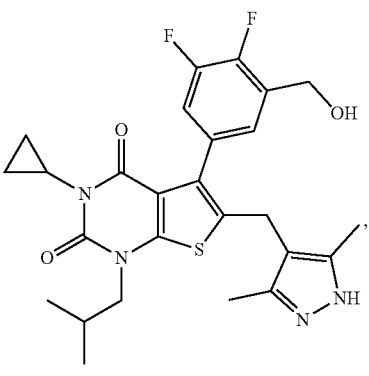
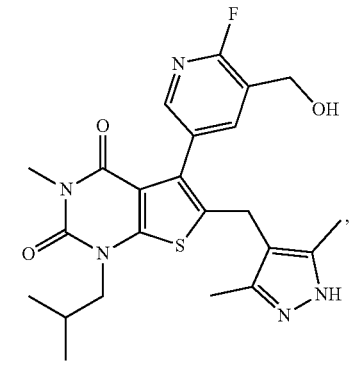
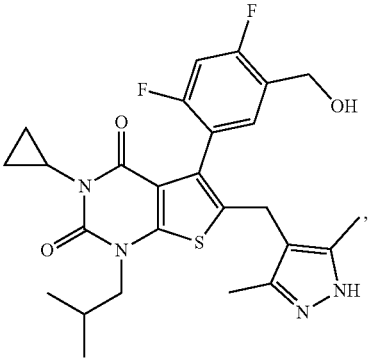

89
-continued
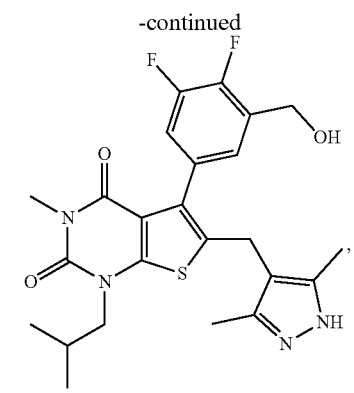
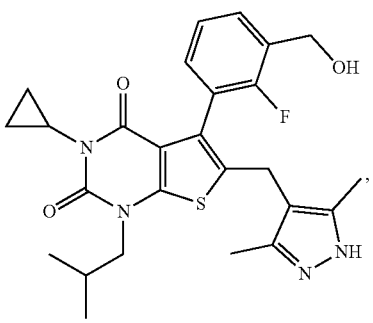
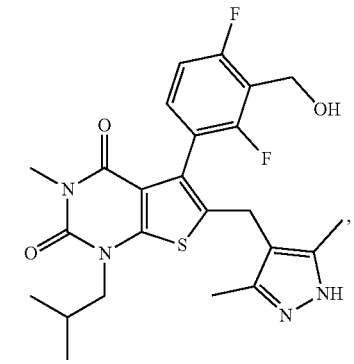
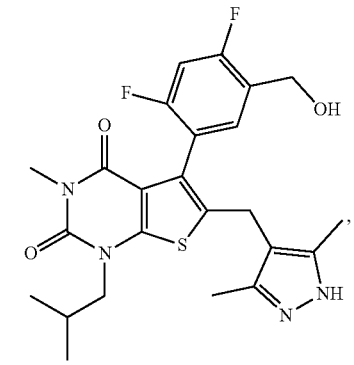
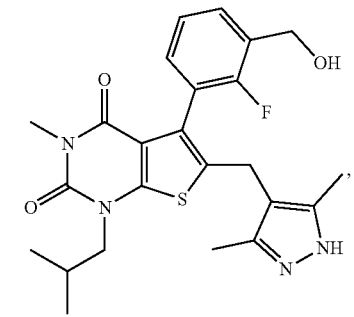
90
-continued
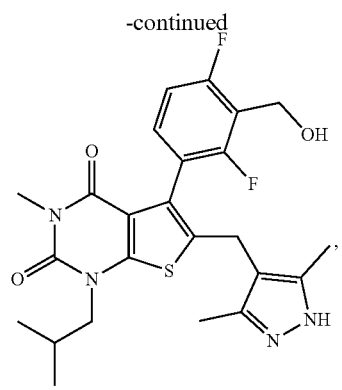
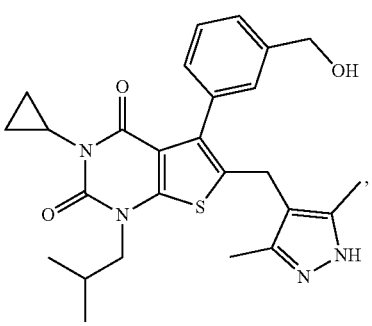
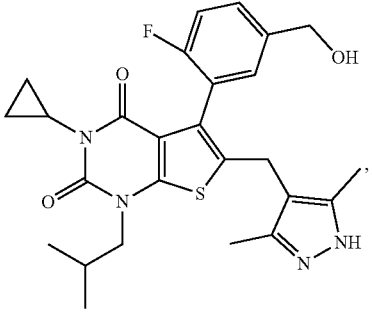
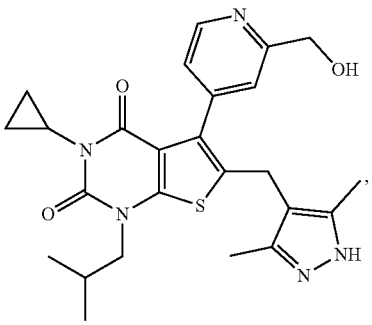
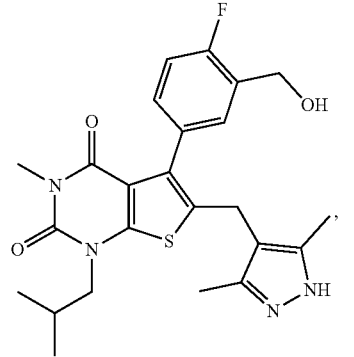

-continued
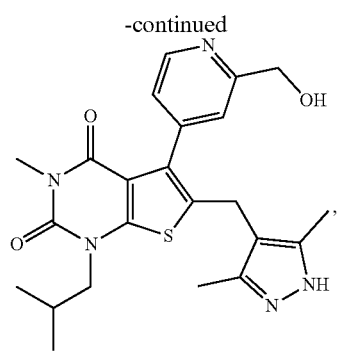
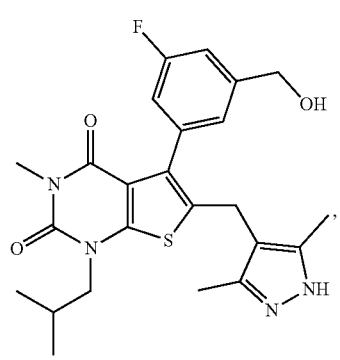
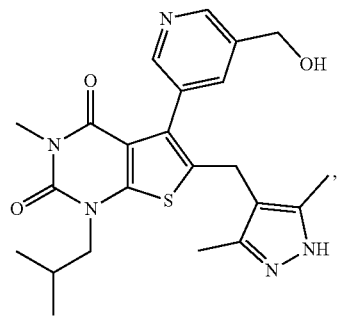
-continued
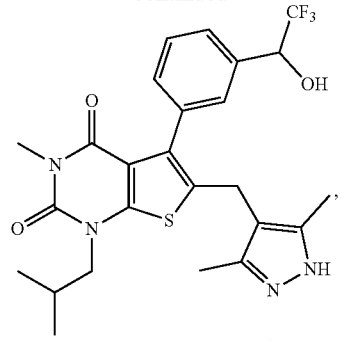
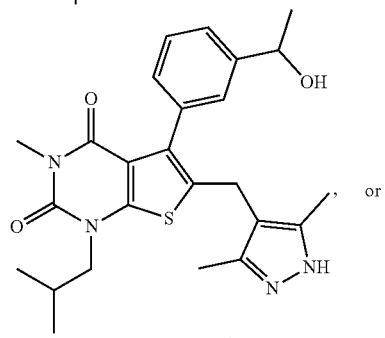, or
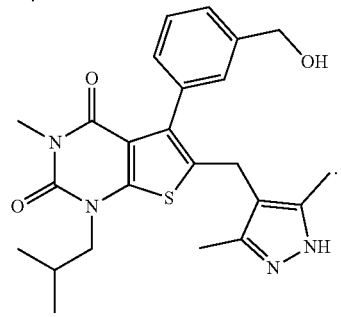
5. A pharmaceutical composition comprising a compound of claim 1 and a pharmaceutically acceptable excipient.
* * * * *